(12) United States Patent
Kolterman et al.

(10) Patent No.: US 7,906,146 B2
(45) Date of Patent: *Mar. 15, 2011

(54) LYOPHILIZED FORMULATIONS OF EXENDINS AND EXENDIN AGONIST ANALOGS

(75) Inventors: Orville G. Kolterman, San Diego, CA (US); Andrew A. Young, Rancho Santa Fe, CA (US); James J. L'Italien, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/389,509

(22) Filed: Feb. 20, 2009

(65) Prior Publication Data

US 2009/0215694 A1    Aug. 27, 2009

Related U.S. Application Data

(63) Continuation of application No. 12/100,880, filed on Apr. 10, 2008, now abandoned, which is a continuation of application No. 11/272,488, filed on Nov. 10, 2005, now Pat. No. 7,399,489, which is a continuation-in-part of application No. 11/083,730, filed on Mar. 18, 2005, now Pat. No. 7,153,825, which is a continuation of application No. 09/889,331, filed as application No. PCT/US00/00942 on Jan. 14, 2000, now Pat. No. 6,872,700.

(60) Provisional application No. 60/175,365, filed on Jan. 10, 2000, provisional application No. 60/132,017, filed on Apr. 30, 1999, provisional application No. 60/116,380, filed on Jan. 14, 1999.

(51) Int. Cl.
*A61K 9/14* (2006.01)
*A61K 38/00* (2006.01)

(52) U.S. Cl. ............ 424/489; 424/278.1; 514/3; 514/12; 530/300; 530/308

(58) Field of Classification Search .................. None
See application file for complete search history.

(56) References Cited

U.S. PATENT DOCUMENTS

| | | | |
|---|---|---|---|
| 4,179,337 | A | 12/1979 | Davis et al. |
| 5,264,372 | A | 11/1993 | Beaumont et al. |
| 5,424,286 | A | 6/1995 | Eng |
| 5,686,511 | A | 11/1997 | Bobo |
| 5,839,443 | A | 11/1998 | Rose et al. |
| 6,051,557 | A | 4/2000 | Drucker |
| 6,268,343 | B1 | 7/2001 | Knudsen et al. |
| 6,376,549 | B1 | 4/2002 | Fine et al. |
| 6,451,974 | B1 | 9/2002 | Hansen |
| 6,902,744 | B1 | 6/2005 | Kolterman et al. |
| 7,902,744 | | 6/2005 | Kolterman et al. |
| 6,924,264 | B1 | 8/2005 | Prickett et al. |
| 7,427,663 | B2 * | 9/2008 | Chen et al. ............... 530/385 |
| 2001/0006876 | A1 * | 7/2001 | Kondo et al. .............. 451/44 |
| 2005/0026834 | A1 | 2/2005 | Cox et al. |

FOREIGN PATENT DOCUMENTS

| | | |
|---|---|---|
| AU | 199731732 | 1/1998 |
| WO | WO 95/07098 | 3/1995 |
| WO | WO 97/46584 | 12/1997 |
| WO | WO 98/05351 | 2/1998 |
| WO | WO 98/30231 | 7/1998 |
| WO | WO 99/07404 | 2/1999 |
| WO | WO 99/25727 | 5/1999 |
| WO | WO 99/25728 | 5/1999 |
| WO | WO 99/40788 | 8/1999 |
| WO | WO 00/41546 | 7/2000 |
| WO | WO 00/41548 | 7/2000 |

OTHER PUBLICATIONS

Polyols (2010, updated) Mannitol, www.polyol.org/fap/fap_mannitol.html, p. 1-2.*

Wikipedia (2010, updated) Sugar alcohol, en.wikipedia.org/wiki/Sugar_alcohol, pp. 1-2.*

Bloom, S.R., "Glucagonoma Syndome"; American J. Medical 82(5B):25-36, Review. (1987).

Byrne, M.M., et al ., "Lessons from Human Studies with Glucagon-like Peptide-1: Potential of the Gut Hormone for Clinical Use," Front. Diabetes, 13:219-33(1997).

Carlsson, A. et al., Insulin and Glucagon Secretion in Patients with Slowly Progressing Autoimmune Diabetes (LADA). J. Clin. Endocrinol. Metab.; 85:76-80(2000).

Chen, Y.E., et al., "Tissue-specific Expression of Unique mRNAs That Encode Proglucagon-derived Peptides or Exendin 4 in the Lizard," Journal of Biological Chemistry, 272 (7):4108-4115 (1997).

Creutzfeldt, W.O.C., et al., "Glucagonostatic Actions and Reduction of Fasting Hyperglycemia by Exogenous Glucagonlike Peptide 1(7-36) Amide in Type I Diabetic Patients," Diabetes Care 19 (6):580-6 (1996).

D'Alessio, et al ., "Elimination of the Action of Glucagonlike Peptide 1 Causes an Impairment of Glucose Tolerance after Nutrient Ingestion by Healthy Baboons," J. Clin. Invest., 97:133-38 (1996).

Daniel, O. et al.,"Use of Glucagon in the Treatment of Acute Diverticultis," British Medical Journal, 3:720-2, (1974).

Delgado, et al. (1979) The uses and properties of PEG-linked proteins. Crit. Rev. Ther. Drug Carrier Syst. vol. 9, issues 3-4, pp. 249-304.

Drucker, D. J., "Glucagon-like Peptides" Diabetes, 47:159-169 (1998).

Egan, J.M., et al ., "Glucagon-like Peptide-1 Restores Acute Phase Insulin Release to Aged Rats," Diabetologia, 40(Supp 1);A130 abstract 505 (1997).

Eissele, et al ., "Rat Gastric Somatostatin and Gastrin Release: Interactions of Exendin-4 and Truncated Glucagon-like Peptide-1 (GLP-1) Amide," Life Sci., 55(8):629-34.

Eng, J., et al., "Purification and Structure of Exendin-3, A New Pancreatic Secretagogue Isolated from *Heloderma horridum* Venom," J. Biol. Chem., 265 (33):20259-62 (1990).

(Continued)

*Primary Examiner* — Anand U Desai
*Assistant Examiner* — Samuel Liu

(57) ABSTRACT

Novel formulations containing exendins, exendin agonists and/or exendin analogs are provided.

20 Claims, 24 Drawing Sheets

OTHER PUBLICATIONS

Eng, J., et al.. "Isolation and Characterization of Exendin-4, an Exendin-3 Analogue, from *Heloderma suspectum* Venom," J. Biol. Chem., 267 (11):7402-05 (1992).

Eng, J., et al., "Prolonged Effect of Exendin-4 on Hyperglycemia of db/db mice," Diabetes. 45(Supp 2):152A (abstract 554) (1996).

Francis, et al., "PEGylation of Cytokines and Other Therapeutic Proteins and Peptides: the Importance of Biological Optimisation of Coupling Techniques," International Journal of Hematology, 68 (1):1-18 (1998).

Glauser, et al., "Intravenous Glucagon in the Management of Esophageal Food Obstruction," JACEP, 8:228-231(1979).

Goke, et al. "Exendin-4 Is a High Potency Agonist and Truncated Exendin-(9-39)-amide an Antagonist at the Glucagon-like Peptide 1-(7-36)-amide Receptor of Insulinsecreting /3-Cells," J. Biol. Chem., 268 (26):19650-55 (1993).

Holst, J. J. Treatment of type 2 diabetes mellitus with agonists of the Emerg Drugs. vol. 9, No. 1, pp. 155-166. Review.(2004).

Lefebvre, et al, (1979) Glucagon and diabetes: a reappraisal. Diabetologia, vol. 18, No. 6, pp. 347-354.

Malhotra, et al., "Exendin-4, a New Peptide from *Heloderma sospectum* Venom, Potentiates Cholecystokinin-Induced Amylase Release from Rat Pancreatic Acini," Regulatory Peptides, 41:149-56 (1982).

Markletter, Aug. 24, 1998 (page n/a).

O'Halloran, et al, "Glucagon-like Peptide-1 (7-36)-NH2: A Physiologic Inhibitor of Gastric Acid Secretion in Man," J. Endocrinol. 126 (1) : 169-73 (1990).

Ørskov, et al., "Biological Effects and Metabolic Rates of Glucagon-like Peptide-1 7-36 Amide and Glucagonlike Peptide-1 7-37 in Healthy Subjects Are Indistinguishable," Diabetes, 42:658-61 (1993).

Parhes, D.G. et al, (2001) "Insulinotropic actions of exendin-4 and glucagon-like peptide-1 in vivo and in vitro" Metabolic, vol. 50, pp. 583-589.

Passa, P., et al , "Mechanisms Suppressing Glucagon Secretion in Glucagonomas," Diabetologia, 19(3):305 [abstract 298] (1980).

Raufman, et al., "Truncated Glucagon-like Peptide-1 Interacts with Exendin Receptors in Dispersed Acini from Guinea Pig Pancreas," J. Biol. Chem., 267 (30) :21432-37 (1992).

Schepp, et al., "Exendin-4 and Exendin-(9-3 9)NH2: Agonist and Antagonist, Respectively, at the Rat Parietal Cell Receptor for Glucagon-like Peptide-1-(7-36)NH2," Eur. J. Pharm., 269:183-91 (1994).

Schjoldager, et al., "GLP-1 (Glucagon-like Peptide 1) and Truncated GLP-1, Fragments of Human Proglucagon, Inhibit Gastric Acid Secretion in Humans," Dig. Dis. Sci., 34(5):703-8 (1989).

Singh, et al., "Use of 125I-[Y39] exendin-4 to Characterize Exendin Receptors on Dispersed Pancreatic Acini and Gastric Chief Cells from Guinea Pig," Regul. Pep., 53:47-59 (1994).

Stower, et al., "A Trial of Glucagon in the Treatment of Painful Biliary Tract Disease," Br. J. Surg., 69:591-2(1982).

Takeda M, Tojo A, Sekine T, Hosoyamada M, Kanai Y, Endou H. "Role of Organic Anion Transporter 1 (OAT1) in Cephaloridine (CER)-Induced Nephrotoxicity." Kidney Int.;56:2128-2136 (1999).

Thorens, "Expression Cloning of the Pancreatic β Cell Receptor for the Gluco-Incretin Hormone Glucagon-like Peptide 1," Proc. Natl. Acad. Sci. USA, 89:8641-45 (1992).

Turton, M.D., et al., "A Role for Glucagon-like Peptide-1 in the Central Regulation of Feeding," Nature, 379:69-72 (1996).

Varshavsky A. "The Ubiquitin System." Trends Biochem Sci. 1997; 22:383-7.

Wettergren, et al. , "Truncated GLP-1 (Proglucagon 78-107-Amide) Inhibits Gastric and Pancreatic Functions in Man" Dig. Dis. Sci. , 38(4):665-73 (1993).

Willms, et al., "Gastric Emptying, Glucose Responses, and Insulin Secretion after a Liquid Test Mai: Effects of Exogenous Glucagon-Like Peptide-1 (GLP-1)-(7-36) Amide in Type 2 (Noninsulin-Dependent) Diabetic Patients," J. Clin. Endocrinol. Metab., 81(I):327-32 (1996).

\* cited by examiner

His Ser Asp Gly Thr Phe Thr Ser Asp Leu Ser Lys Gln Met Glu Glu
1                   5                   10                  15
Glu Ala Val Arg Leu Phe Ile Glu Trp Leu Lys Asn Gly Gly Pro Ser
                20                  25                  30
Ser Gly Ala Pro Pro Pro Ser-NH₂
                35

Fig. 1

His Gly Glu Gly Thr Phe Thr Ser Asp Leu Ser Lys Gln Met Glu Glu
1                   5                   10                  15
Glu Ala Val Arg Leu Phe Ile Glu Trp Leu Lys Asn Gly Gly Pro Ser
                20                  25                  30
Ser Gly Ala Pro Pro Pro Ser-NH₂
                35

Fig. 2

Xaa1 Xaa2 Xaa3 Gly Thr Xaa4 Xaa5 Xaa6 Xaa7 Xaa8 Ser Lys Gln Xaa9 Glu Glu Ala Val Arg Leu
Xaa10 Xaa11 Xaa12 Xaa13 Leu Lys Asn Gly Gly Xaa14 Ser Ser Gly Xaa15 Ala Xaa16 Xaa17 Xaa18-Z

| Compound | SEQ ID NO | Xaa1 | Xaa2 | Xaa3 | Xaa4 | Xaa5 | Xaa6 | Xaa7 | Xaa8 | Xaa9 | Xaa10 | Xaa11 | Xaa12 | Xaa13 | Xaa14 | Xaa15 | Xaa16 | Xaa17 | Xaa18 | Z |
|---|---|---|---|---|---|---|---|---|---|---|---|---|---|---|---|---|---|---|---|---|
| 1 | [10] | His | Gly | Glu | Phe | Thr | Ser | Asp | Leu | Phe | Ile | Glu | Phe | Pro | Pro | Pro | Pro | Ser | NH2 |
| 2 | [11] | His | Gly | Glu | Phe | Thr | Ser | Asp | Leu | Leu | Phe | Glu | Trp | Pro | Pro | Pro | Pro | Ser | NH2 |
| 3 | [12] | His | Gly | Glu | Phe | Thr | Ser | Asp | Leu | Met | Phe | Glu | Pro | Pro | Pro | Pro | Pro | Ser | NH2 |
| 4 | [13] | Tyr | Gly | Glu | Phe | Thr | Ser | Asp | Leu | Met | Phe | Glu | Trp | Pro | Pro | Pro | Pro | Ser | NH2 |
| 5 | [14] | His | Gly | Glu | Phe | Thr | Ser | Asp | Leu | Met | Phe | Glu | Pro | Pro | Pro | Pro | Pro | Tyr | NH2 |
| 6 | [15] | His | Gly | Asp | Phe | Thr | Ser | Asp | Leu | Met | Phe | Glu | Trp | Pro | Pro | Pro | Pro | Ser | NH2 |
| 7 | [16] | His | Gly | Glu | naph | Thr | Ser | Asp | Leu | Met | Phe | Glu | Trp | Pro | Pro | Pro | Pro | Ser | NH2 |
| 8 | [17] | His | Gly | Glu | Phe | Ser | Ser | Asp | Leu | Met | Phe | Glu | Trp | Pro | Pro | Pro | Pro | Ser | NH2 |
| 9 | [18] | His | Gly | Glu | Phe | Thr | Thr | Asp | Leu | Met | Phe | Glu | Trp | Pro | Pro | Pro | Pro | Ser | NH2 |
| 10 | [19] | His | Gly | Glu | Phe | Thr | Ser | Glu | Leu | Met | Phe | Glu | Trp | Pro | Pro | Pro | Pro | Ser | NH2 |
| 11 | [20] | His | Gly | Glu | Phe | Thr | Ser | Asp | Met | Met | Phe | Glu | Trp | Pro | Pro | Pro | Pro | Ser | NH2 |
| 12 | [21] | His | Gly | Glu | Phe | Thr | Ser | Asp | pGly | Met | Phe | Glu | Trp | Pro | Pro | Pro | Pro | Ser | NH2 |
| 13 | [22] | His | Gly | Glu | Phe | Thr | Ser | Asp | pGly | Leu | Phe | Glu | Trp | Pro | Pro | Pro | Pro | Ser | NH2 |
| 14 | [23] | His | Gly | Glu | Phe | Thr | Ser | Asp | Leu | pGly | Phe | Glu | Phe | Pro | Pro | Pro | Pro | Ser | NH2 |
| 15 | [24] | His | Gly | Glu | Phe | Thr | Ser | Asp | Leu | Met | naph | Glu | Phe | Pro | Pro | Pro | Pro | Ser | NH2 |
| 16 | [25] | His | Gly | Glu | Phe | Thr | Ser | Asp | Leu | Met | Phe | Val | Trp | Pro | Pro | Pro | Pro | Ser | NH2 |
| 17 | [26] | His | Gly | Glu | Phe | Thr | Ser | Asp | Leu | Met | Phe | Glu | Trp | Pro | Pro | Pro | Pro | Ser | NH2 |

Fig. 3A

| Compound | SEQ ID NO | Xaa₁ | Xaa₂ | Xaa₃ | Xaa₄ | Xaa₅ | Xaa₆ | Xaa₇ | Xaa₈ | Xaa₉ | Xaa₁₀ | Xaa₁₁ | Xaa₁₂ | Xaa₁₃ | Xaa₁₄ | Xaa₁₅ | Xaa₁₆ | Xaa₁₇ | Xaa₁₈ | Z |
|---|---|---|---|---|---|---|---|---|---|---|---|---|---|---|---|---|---|---|---|---|
| 18 | [27] | His | Gly | Glu | Phe | Thr | Ser | Asp | Leu | Leu | Phe | Val | Glu | Phe | Pro | Pro | Pro | Pro | Ser | NH₂ |
| 19 | [28] | His | Gly | Glu | Phe | Thr | Ser | Asp | Leu | Leu | Phe | tBuG | Glu | Trp | Pro | Pro | Pro | Pro | Ser | NH₂ |
| 20 | [29] | His | Gly | Glu | Phe | Thr | Ser | Asp | Leu | Leu | Phe | tBuG | Glu | Phe | Pro | Pro | Pro | Pro | Ser | NH₂ |
| 21 | [30] | His | Gly | Glu | Phe | Thr | Ser | Asp | Leu | Met | Phe | Ile | Asp | Trp | Pro | Pro | Pro | Pro | Ser | NH₂ |
| 22 | [31] | His | Ala | Glu | Phe | Thr | Ser | Asp | Leu | Leu | Phe | Ile | Glu | Phe | Pro | Pro | Pro | Pro | Ser | NH₂ |
| 23 | [32] | His | Gly | Glu | Phe | Thr | Ser | Asp | Leu | Met | Phe | Ile | Glu | Trp | Pro | Pro | Pro | Pro | Ser | NH₂ |
| 24 | [33] | His | Gly | Glu | Phe | Thr | Ser | Asp | Leu | Leu | Phe | Ile | Glu | Trp | tPro | Pro | Pro | Pro | Ser | NH₂ |
| 25 | [34] | His | Gly | Glu | Phe | Thr | Ser | Asp | Leu | Met | Phe | Ile | Glu | Trp | Pro | tPro | Pro | tPro | Ser | NH₂ |
| 26 | [35] | His | Gly | Glu | Phe | Thr | Ser | Asp | Leu | Leu | Phe | Ile | Glu | Trp | hPro | hPro | hPro | hPro | Ser | NH₂ |
| 27 | [36] | His | Gly | Glu | Phe | Thr | Ser | Asp | Leu | Met | Phe | Ile | Glu | Phe | Pro | tPro | tPro | tPro | Ser | NH₂ |
| 28 | [37] | His | Gly | Glu | Phe | Thr | Ser | Asp | Leu | Leu | Phe | Ile | Glu | Phe | hPro | hPro | Pro | Pro | Ser | NH₂ |
| 29 | [38] | His | Gly | Glu | Phe | Thr | Ser | Asp | Leu | Met | Phe | Ile | Glu | Trp | MeAla | MeAla | MeAla | MeAla | Ser | NH₂ |
| 30 | [39] | His | Gly | Glu | Phe | Thr | Ser | Asp | Leu | Met | Phe | Ile | Glu | Trp | Pro | MeAla | MeAla | MeAla | Ser | NH₂ |
| 31 | [40] | His | Gly | Glu | Phe | Thr | Ser | Asp | Leu | Leu | Phe | Ile | Glu | Phe | MeAla | MeAla | MeAla | MeAla | Ser | NH₂ |

His Xaa$_2$ Glu Gly Xaa$_5$ Xaa$_6$ Thr Xaa$_8$ Asp Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Val Arg Xaa$_{21}$ Phe Ile Xaa$_{24}$ Xaa$_{25}$ Leu Lys Asn Xaa$_{29}$ Xaa$_{30}$ –NH$_2$

| Compound and SEQ ID No. | 2 | 5 | 6 | 8 | 10 | 11 | 12 | 13 | 14 | 15 | 16 | 17 | 21 | 24 | 25 | 29 | 30 |
|---|---|---|---|---|---|---|---|---|---|---|---|---|---|---|---|---|---|
| 1-049 | Gly | Thr | Phe | Ser | Leu | Ser | Lys | Gln | Met | Glu | Glu | Glu | Leu | Glu | Trp | Gly | Gly |
| 2-050 | Gly | Thr | Phe | Ser | Leu | Ser | Lys | Gln | Met | Glu | Glu | Glu | Leu | Glu | Trp | | |
| 3-051 | Gly | Thr | Phe | Ser | Leu | Ser | Lys | Gln | Leu | Glu | Glu | Glu | Leu | Glu | Phe | | |
| 4-052 | Ala | Thr | Phe | Ser | Leu | Ser | Lys | Gln | Leu | Glu | Glu | Glu | Leu | Glu | Phe | | |
| 5-053 | Gly | Ala | Phe | Ser | Leu | Ser | Lys | Gln | Leu | Glu | Glu | Glu | Leu | Glu | Phe | | |
| 6-054 | Gly | Thr | Ala | Ser | Leu | Ser | Lys | Gln | Leu | Glu | Glu | Glu | Leu | Glu | Phe | | |
| 7-055 | Gly | Thr | Phe | Ala | Leu | Ser | Lys | Gln | Leu | Glu | Glu | Glu | Leu | Glu | Phe | | |
| 8-056 | Gly | Thr | Phe | Ser | Ala | Ser | Lys | Gln | Leu | Glu | Glu | Glu | Leu | Glu | Phe | | |
| 9-057 | Gly | Thr | Phe | Ser | Leu | Ala | Lys | Gln | Leu | Glu | Glu | Glu | Leu | Glu | Phe | | |
| 10-058 | Gly | Thr | Phe | Ser | Leu | Ser | Ala | Gln | Leu | Glu | Glu | Glu | Leu | Glu | Phe | | |
| 11-059 | Gly | Thr | Phe | Ser | Leu | Ser | Lys | Ala | Leu | Glu | Glu | Glu | Leu | Glu | Phe | | |
| 12-060 | Gly | Thr | Phe | Ser | Leu | Ser | Lys | Gln | Ala | Glu | Glu | Glu | Leu | Glu | Phe | | |
| 13-061 | Gly | Thr | Phe | Ser | Leu | Ser | Lys | Gln | Leu | Ala | Glu | Glu | Leu | Glu | Phe | | |
| 14-062 | Gly | Thr | Phe | Ser | Leu | Ser | Lys | Gln | Leu | Glu | Ala | Glu | Leu | Glu | Phe | | |
| 15-063 | Gly | Thr | Phe | Ser | Leu | Ser | Lys | Gln | Leu | Glu | Glu | Ala | Leu | Glu | Phe | | |
| 16-064 | Gly | Thr | Phe | Ser | Leu | Ser | Lys | Gln | Leu | Glu | Glu | Glu | Ala | Glu | Phe | | |
| 17-065 | Gly | Thr | Phe | Ser | Leu | Ser | Lys | Gln | Leu | Glu | Glu | Glu | Leu | Glu | Phe | | |
| 18-066 | Gly | Thr | Phe | Ser | Leu | Ser | Lys | Gln | Leu | Glu | Glu | Glu | Ala | Glu | Phe | | |
| 19-067 | Gly | Thr | Phe | Ser | Leu | Ser | Lys | Gln | Leu | Glu | Glu | Glu | Leu | Ala | Phe | | |
| 20-068 | Gly | Thr | Phe | Ser | Leu | Ser | Lys | Gln | Leu | Glu | Glu | Glu | Leu | Glu | Ala | | |

Figure 4B

His Gly Glu Gly Thr Phe Thr Ser Asp Leu Ser Lys Gln Xaa$_{14}$ Glu Glu Glu Ala Val Arg Leu Phe Ile Glu Xaa$_{25}$ Xaa$_{26}$ Xaa$_{27}$ Xaa$_{28}$ Xaa$_{29}$ Xaa$_{30}$ Xaa$_{31}$ Xaa$_{32}$ Xaa$_{33}$ Xaa$_{34}$ Xaa$_{35}$ Xaa$_{36}$ Xaa$_{37}$ Xaa$_{38}$ –NH$_2$

| Compound and SEQ ID NO. | 14 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|
| 21-069 | Leu | Phe | Ala | Lys | Asn | | | | | | | | | | |
| 22-070 | Leu | Phe | Leu | Ala | Asn | | | | | | | | | | |
| 23-071 | Leu | Phe | Leu | Lys | Ala | | | | | | | | | | |
| 24-072 | Met | Trp | Leu | Lys | Asn | Gly | | | | | | | | | |
| 25-073 | Leu | Phe | Leu | Lys | Asn | Gly | | | | | | | | | |
| 26-074 | Met | Trp | Leu | Lys | Asn | Gly | Gly | | | | | | | | |
| 27-075 | Leu | Phe | Leu | Lys | Asn | Gly | Gly | | | | | | | | |
| 28-076 | Met | Trp | Leu | Lys | Asn | Gly | Gly | Pro | | | | | | | |
| 29-077 | Leu | Phe | Leu | Lys | Asn | Gly | Gly | Pro | | | | | | | |
| 30-078 | Met | Trp | Leu | Lys | Asn | Gly | Gly | Pro | Ser | | | | | | |
| 31-079 | Leu | Phe | Leu | Lys | Asn | Gly | Gly | Pro | Ser | | | | | | |
| 32-080 | Met | Trp | Leu | Lys | Asn | Gly | Gly | Pro | Ser | Ser | | | | | |
| 33-081 | Leu | Phe | Leu | Lys | Asn | Gly | Gly | Pro | Ser | Ser | | | | | |
| 34-082 | Met | Trp | Leu | Lys | Asn | Gly | Gly | Pro | Ser | Ser | Gly | | | | |
| 35-083 | Leu | Phe | Leu | Lys | Asn | Gly | Gly | Pro | Ser | Ser | Gly | | | | |
| 36-084 | Met | Trp | Leu | Lys | Asn | Gly | Gly | Pro | Ser | Ser | Gly | Ala | | | |
| 37-085 | Leu | Phe | Leu | Lys | Asn | Gly | Gly | Pro | Ser | Ser | Gly | Ala | Pro | | |
| 38-086 | Met | Trp | Leu | Lys | Asn | Gly | Gly | Pro | Ser | Ser | Gly | Ala | Pro | | |
| 39-087 | Leu | Phe | Leu | Lys | Asn | Gly | Gly | Pro | Ser | Ser | Gly | Ala | Pro | Pro | |
| 40-088 | Leu | Phe | Leu | Lys | Asn | Gly | Gly | Pro | | | | | Pro | Pro | |
| 41-089 | Met | Trp | Leu | Lys | Asn | Gly | | | | | | | | Pro | Pro |

Figure 4C

Xaa$_1$ Gly Xaa$_3$ Gly Thr Xaa$_6$ Xaa$_7$ Xaa$_8$ Xaa$_9$ Xaa$_{10}$ Ser Lys Gln Xaa$_{14}$ Xaa$_{15}$ Gly Glu Ala Val Arg Leu Xaa$_{22}$ Xaa$_{23}$ Xaa$_{24}$ Xaa$_{25}$ Leu Lys Asn Xaa$_{29}$ Xaa$_{30}$ Xaa$_{31}$ Xaa$_{32}$ Xaa$_{33}$ Xaa$_{34}$ Xaa$_{35}$ Xaa$_{36}$ Xaa$_{37}$ Xaa$_{38}$-NH$_2$

| Compound and SEQ ID. | Amino Acid Xaa in Position in Above Sequence | | | | | | | | | | | | | | | | | | | | | | |
|---|---|---|---|---|---|---|---|---|---|---|---|---|---|---|---|---|---|---|---|---|---|---|---|
| | 1 | 3 | 6 | 7 | 8 | 9 | 10 | 14 | 15 | 22 | 23 | 24 | 25 | 29 | 30 | 31 | 32 | 33 | 34 | 35 | 36 | 37 | 38 |
| 42-090 | His | Glu | Phe | Thr | Ser | Asp | Leu | Leu | Glu | Phe | Ile | Glu | Phe | Gly | | | | | | | | | |
| 43-091 | His | Glu | Phe | Thr | Ser | Asp | Leu | Met | Glu | Phe | Ile | Glu | Trp | Gly | Gly | tPro | Ser | Ser | Gly | Ala | tPro | tPro | tPro |
| 44-092 | His | Glu | Phe | Thr | Ser | Asp | Leu | Met | Glu | Phe | Ile | Glu | Trp | Gly | Gly | Pro | Ser | Ser | Gly | Ala | tPro | tPro | tPro |
| 45-093 | His | Glu | Phe | Thr | Ser | Asp | Leu | Met | Glu | Phe | Ile | Glu | Trp | Gly | Gly | Nme | Ser | Ser | Gly | Ala | Pro | Pro | |
| 46-094 | His | Glu | Phe | Thr | Ser | Asp | Leu | Met | Glu | Phe | Ile | Glu | Trp | Gly | Gly | Nme | Ser | Ser | Gly | Ala | Nme | Nme | |
| 47-095 | His | Glu | Phe | Thr | Ser | Asp | Leu | Met | Glu | Phe | Ile | Glu | Trp | Gly | Gly | hPro | Ser | Ser | Gly | Ala | hPro | hPro | |
| 48-096 | His | Glu | Phe | Thr | Ser | Asp | Leu | Met | Glu | Phe | Ile | Glu | Trp | Gly | Gly | hPro | Ser | Ser | Gly | Ala | hPro | | |
| 49-097 | Arg | Glu | Phe | Thr | Ser | Asp | Leu | Met | Glu | Phe | Ile | Glu | Trp | Gly | Gly | Pro | Ser | Ser | Gly | Ala | | | |
| 50-098 | His | Asp | Phe | Thr | Ser | Asp | Leu | Met | Glu | Phe | Ile | Glu | Trp | Gly | Gly | | | | | | | | |
| 51-099 | His | Glu | naph | Thr | Ser | Asp | Leu | Leu | Glu | Phe | Ile | Glu | Phe | | | | | | | | | | |
| 52-100 | His | Glu | Phe | Ser | Ser | Asp | Leu | Met | Glu | Phe | Ile | Glu | Trp | | | | | | | | | | |
| 53-101 | His | Glu | Phe | Ser | Thr | Asp | Leu | Met | Glu | Phe | Ile | Glu | Trp | | | | | | | | | | |
| 54-102 | His | Glu | Phe | Thr | Ser | Glu | Leu | Met | Ala | Phe | Ile | Glu | Trp | | | | | | | | | | |
| 55-103 | His | Glu | Phe | Thr | Ser | Asp | pGly | Leu | Glu | Phe | Ile | Glu | Trp | | | | | | | | | | |
| 56-104 | His | Glu | Phe | Thr | Ser | Asp | Leu | Leu | Glu | naph | Ile | Glu | Phe | | | | | | | | | | |
| 57-105 | His | Glu | Phe | Thr | Ser | Asp | Leu | Met | Glu | Phe | Ile | Glu | Trp | | | | | | | | | | |
| 58-106 | His | Glu | Phe | Thr | Ser | Asp | Leu | Leu | Glu | Phe | tBug | Asp | Trp | | | | | | | | | | |
| 59-107 | His | Glu | Phe | Thr | Ser | Asp | Leu | Leu | Glu | Phe | Ile | Glu | Phe | Gly | Gly | Pro | Ser | Ser | | | | | |
| 60-108 | His | Glu | Phe | Thr | Ser | Asp | Ala | Met | Glu | Phe | Ile | Glu | Trp | Gly | Gly | | | | | | | | |
| 61-109 | His | Glu | Phe | Thr | Ser | Asp | Ala | Met | Glu | Phe | Ile | Glu | Trp | Gly | Gly | hPro | Ser | Ser | Gly | Ala | hPro | hPro | |

Figure 4D

Xaa$_1$Xaa$_2$Xaa$_3$Xaa$_4$Xaa$_5$Xaa$_6$Xaa$_7$Xaa$_8$Xaa$_9$Xaa$_{10}$Xaa$_{11}$Xaa$_{12}$ Xaa$_{13}$Xaa$_{14}$ Glu Glu Ala Val Arg Leu Phe Ile Glu Xaa$_{25}$ Leu Lys Asn-NH$_2$

| Cmpd and SEQ ID. | Xaa$_1$ | Xaa$_2$ | Xaa$_3$ | Xaa$_4$ | Xaa$_5$ | Xaa$_6$ | Xaa$_7$ | Xaa$_8$ | Xaa$_9$ | Xaa$_{10}$ | Xaa$_{11}$ | Xaa$_{12}$ | Xaa$_{13}$ | Xaa$_{14}$ | Xaa$_{25}$ |
|---|---|---|---|---|---|---|---|---|---|---|---|---|---|---|---|
| 70 - 118 | Ala | Gly | Glu | Gly | Thr | Phe | Thr | Ser | Asp | Leu | Ser | Lys | Gln | Leu | Phe |
| 71 - 119 | His | Gly | Ala | Gly | Thr | Phe | Thr | Ser | Asp | Leu | Ser | Lys | Gln | Leu | Phe |
| 72 - 120 | His | Gly | Glu | Ala | Thr | Phe | Thr | Ser | Asp | Leu | Ser | Lys | Gln | Leu | Phe |
| 73 - 121 | His | Gly | Glu | Gly | Thr | Phe | Thr | Ser | Ala | Leu | Ser | Lys | Gln | Leu | Phe |
| 74 - 122 | Ala | Gly | Glu | Gly | Thr | Phe | Thr | Ser | Asp | Leu | Ser | Lys | Gln | Met | Trp |
| 75 - 123 | His | Gly | Ala | Gly | Thr | Phe | Thr | Ser | Asp | Leu | Ser | Lys | Gln | Met | Trp |
| 76 - 124 | His | Gly | Glu | Ala | Thr | Phe | Thr | Ser | Ala | Leu | Ser | Lys | Gln | Met | Trp |
| 77 - 125 | His | Gly | Glu | Gly | Thr | Phe | Thr | Ser | Asp | Ala | Ser | Lys | Gln | Met | Trp |
| 78 - 126 | His | Gly | Glu | Gly | Thr | Phe | Thr | Ser | Asp | Leu | Ser | Lys | Gln | Met | Trp |
| 79 - 127 | Ala | Ala | Glu | Gly | Thr | Phe | Thr | Ser | Asp | Leu | Ser | Lys | Gln | Leu | Phe |
| 80 - 128 | Ala | Ala | Glu | Gly | Thr | Phe | Thr | Ser | Asp | Leu | Ser | Lys | Gln | Met | Trp |
| 81 - 129 | Ala | Gly | Asp | Gly | Thr | Phe | Thr | Ser | Asp | Leu | Ser | Lys | Gln | Leu | Phe |
| 82 - 130 | Ala | Gly | Asp | Gly | Thr | Phe | Ser | Ser | Asp | Leu | Ser | Lys | Gln | Met | Phe |
| 83 - 131 | Ala | Gly | Asp | Gly | Ala | Phe | Ser | Ser | Asp | Leu | Ser | Lys | Gln | Leu | Trp |
| 84 - 132 | Ala | Gly | Asp | Gly | Ala | Phe | Thr | Ser | Asp | Leu | Ser | Lys | Gln | Met | Phe |
| 85 - 133 | Ala | Gly | Asp | Gly | Thr | Nala | Thr | Ser | Asp | Leu | Ser | Lys | Gln | Leu | Trp |
| 86 - 134 | Ala | Gly | Asp | Gly | Thr | Nala | Thr | Ser | Asp | Leu | Ser | Lys | Gln | Met | Phe |
| 87 - 135 | Ala | Gly | Asp | Gly | Thr | Phe | Ser | Ser | Asp | Leu | Ser | Lys | Gln | Leu | Trp |
| 88 - 136 | Ala | Gly | Asp | Gly | Thr | Phe | Ser | Ala | Asp | Leu | Ser | Lys | Gln | Leu | Phe |
| 89 - 137 | Ala | Gly | Asp | Gly | Thr | Phe | Thr | Ala | Asp | Leu | Ser | Lys | Gln | Met | Trp |
| 90 - 138 | Ala | Gly | Asp | Gly | Thr | Phe | Thr | Ser | Asp | Leu | Ser | Lys | Gln | Leu | Phe |
| 91 - 139 | Ala | Gly | Asp | Gly | Thr | Phe | Thr | Ser | Ala | Leu | Ser | Lys | Gln | Met | Trp |

Figure 4E

Ala Gly Asp Gly Thr Phe Thr Ser $Xaa_9$ $Xaa_{10}$ $Xaa_{11}$ $Xaa_{12}$ $Xaa_{13}$ $Xaa_{14}$ Glu Glu Glu Ala Val Arg Leu Phe Ile Glu $Xaa_{25}$ Leu Lys Asn-$NH_2$

| Cmpd. and SEQ ID | Amino Acid Position in Above Sequence | | | | | | |
|---|---|---|---|---|---|---|---|
| | $Xaa_9$ | $Xaa_{10}$ | $Xaa_{11}$ | $Xaa_{12}$ | $Xaa_{13}$ | $Xaa_{14}$ | $Xaa_{25}$ |
| 92 - 140 | Ala | Leu | Ser | Lys | Gln | Leu | Phe |
| 93 - 141 | Glu | Leu | Ser | Lys | Gln | Met | Trp |
| 94 - 142 | Glu | Leu | Ser | Lys | Gln | Leu | Phe |
| 95 - 143 | Asp | Ala | Ser | Lys | Gln | Met | Trp |
| 96 - 144 | Asp | Ala | Ser | Lys | Gln | Leu | Phe |
| 97 - 145 | Asp | Pgly | Ser | Lys | Gln | Met | Trp |
| 98 - 146 | Asp | Pgly | Ser | Lys | Gln | Leu | Phe |
| 99 - 147 | Asp | Leu | Ala | Lys | Gln | Met | Trp |
| 100 - 148 | Asp | Leu | Ala | Lys | Gln | Leu | Phe |
| 101 - 150 | Asp | Leu | Ser | Ala | Gln | Met | Trp |
| 102 - 151 | Asp | Leu | Ser | Ala | Gln | Leu | Phe |
| 103 - 152 | Asp | Leu | Ser | Lys | Ala | Met | Trp |
| 104 - 153 | Asp | Leu | Ser | Lys | Ala | Leu | Phe |

Figure 4F

Ala Gly Asp Gly Thr Phe Thr Ser Asp Leu Ser Lys Gln Xaa$_{14}$ Xaa$_{15}$ Xaa$_{16}$ Xaa$_{17}$ Ala Xaa$_{19}$ Xaa$_{20}$ Xaa$_{21}$ Xaa$_{22}$ Xaa$_{23}$ Glu Xaa$_{25}$ Leu Lys Asn-NH$_2$

| Cmpd and SEQ ID | Xaa$_{14}$ | Xaa$_{15}$ | Xaa$_{16}$ | Xaa$_{17}$ | Xaa$_{18}$ | Xaa$_{19}$ | Xaa$_{20}$ | Xaa$_{21}$ | Xaa$_{22}$ | Xaa$_{23}$ | Xaa$_{24}$ | Xaa$_{25}$ |
|---|---|---|---|---|---|---|---|---|---|---|---|---|
| 105 - 154 | Ala | Glu | Glu | Glu | Ala | Val | Arg | Leu | Phe | Ile | Glu | Trp |
| 106 - 155 | Ala | Glu | Glu | Glu | Ala | Val | Arg | Leu | Phe | Ile | Glu | Phe |
| 107 - 156 | pGly | Glu | Glu | Glu | Ala | Val | Arg | Leu | Phe | Ile | Glu | Trp |
| 108 - 157 | pGly | Glu | Glu | Glu | Ala | Val | Arg | Leu | Phe | Ile | Glu | Phe |
| 109 - 158 | Met | Ala | Glu | Glu | Ala | Val | Arg | Leu | Phe | Ile | Glu | Trp |
| 110 - 159 | Leu | Ala | Glu | Glu | Ala | Val | Arg | Leu | Phe | Ile | Glu | Phe |
| 111 - 160 | Met | Glu | Ala | Glu | Ala | Val | Arg | Leu | Phe | Ile | Glu | Trp |
| 112 - 161 | Leu | Glu | Ala | Glu | Ala | Val | Arg | Leu | Phe | Ile | Glu | Phe |
| 113 - 162 | Met | Glu | Glu | Ala | Ala | Val | Arg | Leu | Phe | Ile | Glu | Trp |
| 114 - 163 | Leu | Glu | Glu | Ala | Ala | Val | Arg | Leu | Phe | Ile | Glu | Phe |
| 115 - 164 | Met | Glu | Glu | Glu | Ala | Ala | Arg | Leu | Phe | Ile | Glu | Trp |
| 116 - 165 | Leu | Glu | Glu | Glu | Ala | Ala | Arg | Leu | Phe | Ile | Glu | Phe |
| 117 - 166 | Met | Glu | Glu | Glu | Ala | Val | Ala | Leu | Phe | Ile | Glu | Trp |
| 118 - 167 | Leu | Glu | Glu | Glu | Ala | Val | Ala | Leu | Phe | Ile | Glu | Phe |
| 119 - 168 | Met | Glu | Glu | Glu | Ala | Val | Arg | Ala | Phe | Ile | Glu | Trp |
| 120 - 169 | Leu | Glu | Glu | Glu | Ala | Val | Arg | Ala | Phe | Ile | Glu | Phe |
| 121 - 170 | Met | Glu | Glu | Glu | Ala | Val | Arg | Leu | Nala | Ile | Glu | Trp |
| 122 - 171 | Leu | Glu | Glu | Glu | Ala | Val | Arg | Leu | Nala | Ile | Glu | Phe |
| 123 - 172 | Met | Glu | Glu | Glu | Ala | Val | Arg | Leu | Phe | Val | Glu | Trp |
| 124 - 173 | Leu | Glu | Glu | Glu | Ala | Val | Arg | Leu | Phe | Val | Glu | Phe |

Figure 4G

Ala Gly Asp Gly Thr Phe Thr Ser Asp Leu Ser Lys Gln Xaa$_{14}$ Glu Glu Ala Val Arg Leu Phe Xaa$_{23}$ Xaa$_{24}$ Xaa$_{25}$ Xaa$_{26}$ Xaa$_{27}$ Xaa$_{28}$-NH$_2$

| Cmpd and SEQ ID | Amino Acid Position in Above Sequence | | | | | | |
|---|---|---|---|---|---|---|---|
| | Xaa$_{14}$ | Xaa$_{23}$ | Xaa$_{24}$ | Xaa$_{25}$ | Xaa$_{26}$ | Xaa$_{27}$ | Xaa$_{28}$ |
| 125 - 174 | Met | tGly | Glu | Trp | Leu | Lys | Asn |
| 126 - 175 | Leu | tGly | Glu | Phe | Leu | Lys | Asn |
| 127 - 176 | Met | Ile | Asp | Trp | Leu | Lys | Asn |
| 128 - 177 | Leu | Ile | Asp | Phe | Leu | Lys | Asn |
| 129 - 178 | Met | Ile | Glu | Ala | Leu | Lys | Asn |
| 130 - 179 | Leu | Ile | Glu | Ala | Leu | Lys | Asn |
| 131 - 180 | Met | Ile | Glu | Trp | Ala | Lys | Asn |
| 132 - 181 | Leu | Ile | Glu | Phe | Ala | Lys | Asn |
| 133 - 182 | Met | Ile | Glu | Trp | Leu | Ala | Asn |
| 134 - 183 | Leu | Ile | Glu | Phe | Leu | Ala | Asn |
| 135 - 184 | Met | Ile | Glu | Trp | Leu | Lys | Ala |
| 136 - 185 | Leu | Ile | Glu | Phe | Leu | Lys | Ala |

Figure 4H

Xaa$_1$ Gly Xaa$_3$Xaa$_4$ Thr Phe Thr Ser Xaa$_9$Xaa$_{10}$ Ser Lys Gln Xaa$_{14}$ Glu Glu Gln Ala Val Arg Leu Phe Ile Glu Xaa$_{25}$ Leu Lys Asn Gly Xaa$_{30}$ Xaa$_{31}$ Xaa$_{32}$ Xaa$_{33}$ Xaa$_{34}$ Xaa$_{35}$ Xaa$_{36}$ Xaa$_{37}$ Xaa$_{38}$ Xaa$_{39}$-NH$_2$

| Cmpd and SEQ ID No. | 1 | 3 | 4 | 9 | 10 | 14 | 25 | 30 | 31 | 32 | 33 | 34 | 35 | 36 | 37 | 38 | 39 |
|---|---|---|---|---|---|---|---|---|---|---|---|---|---|---|---|---|---|
| 137 - 186 | Ala | Glu | Gly | Asp | Leu | Met | Trp | Gly | Pro | Ser | Ser | Gly | Ala | Pro | Pro | Pro | |
| 138 - 187 | His | Ala | Gly | Asp | Leu | Leu | Phe | Gly | Pro | Ser | Ser | Gly | Ala | Pro | Pro | Pro | |
| 139 - 188 | His | Glu | Ala | Asp | Leu | Met | Trp | Gly | Pro | Ser | Ser | Gly | Ala | Pro | Pro | | |
| 140 - 189 | His | Glu | Gly | Ala | Leu | Met | Trp | Gly | Pro | Ser | Ser | Gly | Ala | Pro | | | |
| 141 - 190 | Ala | Glu | Gly | Asp | Ala | Leu | Phe | Gly | Pro | Ser | Ser | Gly | Ala | Pro | | | |
| 142 - 191 | Ala | Glu | Gly | Asp | Leu | Met | Trp | Gly | Pro | Ser | Ser | Gly | Ala | | | | |
| 143 - 192 | His | Ala | Gly | Asp | Leu | Leu | Phe | Gly | Pro | Ser | Ser | Gly | Ala | | | | |
| 144 - 193 | His | Glu | Ala | Asp | Leu | Met | Trp | Gly | Pro | Ser | Ser | Gly | | | | | |
| 145 - 194 | His | Glu | Gly | Ala | Leu | Met | Trp | Gly | Pro | Ser | Ser | | | | | | |
| 146 - 195 | Ala | Glu | Gly | Asp | Leu | Met | Trp | Gly | Pro | Ser | | | | | | | |
| 147 - 196 | His | Ala | Gly | Asp | Leu | Leu | Phe | Gly | Pro | Ser | | | | | | | |
| 148 - 197 | His | Glu | Ala | Asp | Leu | Met | Trp | Gly | Pro | | | | | | | | |
| 149 - 198 | His | Glu | Gly | Ala | Leu | Leu | Phe | Gly | | | | | | | | | |
| 150 - 199 | Ala | Glu | Gly | Asp | Leu | Leu | Phe | | | | | | | | | | |
| 151 - 200 | His | Ala | Gly | Asp | Leu | Met | Trp | Gly | tPro | Ser | Ser | Gly | Ala | tPro | tPro | tPro | |
| 152 - 201 | His | Glu | Ala | Asp | Leu | Met | Trp | Gly | Pro | Ser | Ser | Gly | Ala | tPro | tPro | tPro | |
| 153 - 202 | His | Glu | Gly | Ala | Leu | Met | Trp | Gly | Nme | Ser | Ser | Gly | Ala | Nme | Nme | | |
| 154 - 203 | Ala | Glu | Gly | Asp | Leu | Met | Trp | Gly | hPro | Ser | Ser | Gly | Ala | hPro | | | |
| 155 - 204 | His | Ala | Gly | Asp | Leu | Met | Trp | Gly | Pro | Ser | Ser | Gly | Ala | | | | |
| 156 - 205 | His | Asp | Ala | Asp | Leu | Met | Trp | Gly | | | | | | | | | |
| 157 - 206 | Ala | Glu | Gly | Asp | Leu | Met | Trp | Gly | Pro | Ser | Ser | Gly | Ala | Pro | Pro | Pro | Ser |
| 158 - 207 | Ala | Ala | Gly | Asp | Leu | Leu | Phe | Gly | Pro | Ser | Ser | Gly | Ala | Pro | Pro | Pro | Ser |

Figure 4I

| Compound No. | Sequence |
|---|---|
| 159 | 4-imidazolylpropionyl-GEGTFTSALSKQMEEEAVRLFIEWLK(-NH$^\varepsilon$octanoyl)N-NH$_2$ |
| 160 | 4-imidazolylpropionyl-GEGTFTSALSKQLEEEAVRLFIEFLK(-NH$^\varepsilon$octanoyl)N-NH$_2$ |
| 161 | 4-imidazolylpropionyl-GEGTFTSALSKQMEEEAVRLFIEWLK(-NH$^\varepsilon$octanoyl)NGG-NH$_2$ |
| 162 | 4-imidazolylpropionyl-GEGTFTSALSKQLEEEAVRLFIEFLK(-NH$^\varepsilon$octanoyl)NGG-NH$_2$ |
| 163 | 4-imidazolylpropionyl-GEGTFTSALSKQMEEEAVRLFIEWLNK(-NH$^\varepsilon$octanoyl)-NH$_2$ |
| 164 | 4-imidazolylpropionyl-GEGTFTSALSKQLEEEAVRLFIEFLNK(-NH$^\varepsilon$octanoyl)-NH$_2$ |
| 165 | 4-imidazolylpropionyl-GEFTFTSALSKQMEEEAVRLFIEWLNK(-NH$^\varepsilon$octanoyl)GG-NH$_2$ |
| 166 | 4-imidazolylpropionyl-GEFTFTSALSKQLEEEAVRLFIEFLNK(-NH$^\varepsilon$octanoyl)GG-NH$_2$ |
| 167 | AGEFTFTSDLSKQMEEEAVRLFIEWLK(-NH$^\varepsilon$octanoyl)N-NH$_2$ |
| 168 | AGEGTFTSDLSKQLEEEAVRLFIEFLK(-NH$^\varepsilon$octanoyl)N-NH$_2$ |
| 169 | AGEGTFTSDLSKQMEEEAVRLFIEWLK(-NH$^\varepsilon$octanoyl)NGG-NH$_2$ |
| 170 | AGEGTFTSDLSKQLEEEAVRLFIEFLK(-NH$^\varepsilon$octanoyl)NGG-NH$_2$ |
| 171 | AGEGTFTSDLSKQMEEEAVRLFIEWLNK(-NH$^\varepsilon$octanoyl)-NH$_2$ |
| 172 | AGEGTFTSDLSKQLEEEAVRLFIEFLNK(-NH$^\varepsilon$octanoyl)-NH$_2$ |
| 173 | AGEGTFTSDLSKQMEEEAVRLFIEWLNK(-NH$^\varepsilon$octanoyl)GG-NH$_2$ |
| 174 | AGEGTFTSDLSKQLEEEAVRLFIEFLNK(-NH$^\varepsilon$octanoyl)GG-NH$_2$ |

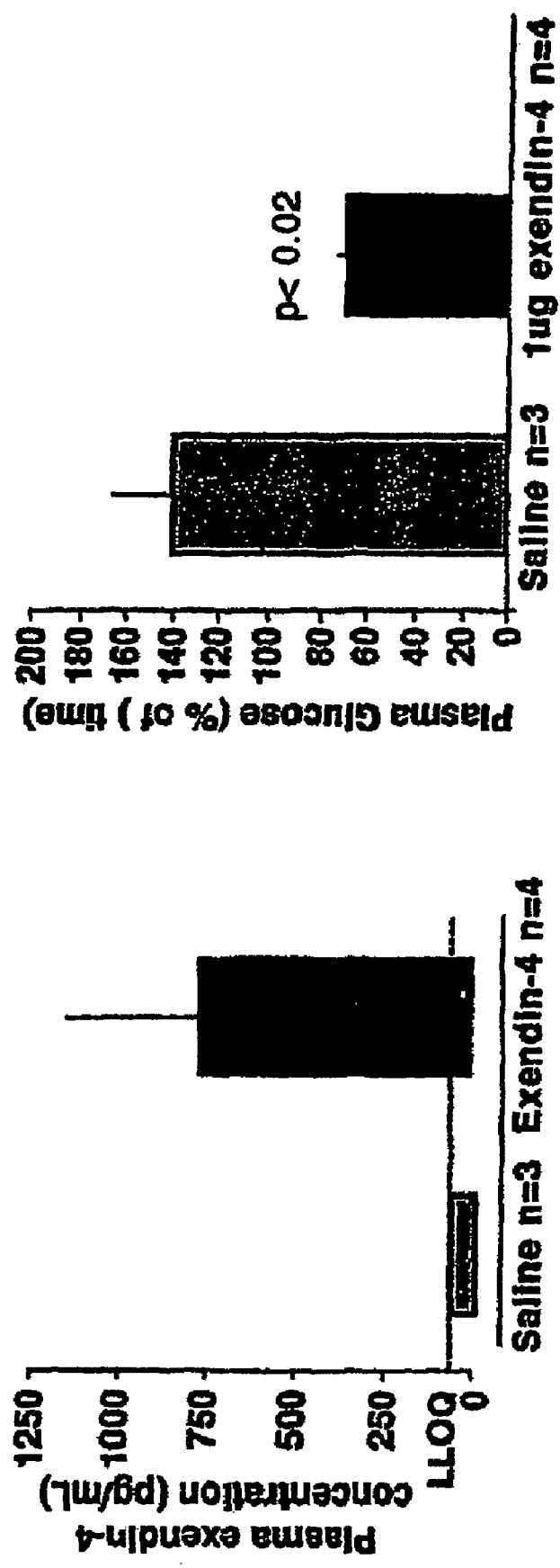

SEQUENCE LISTING

```
<160> NUMBER OF SEQ ID NOS: 239

<210> SEQ ID NO 1
<211> LENGTH: 39
<212> TYPE: PRT
<213> ORGANISM: Heloderma Horridum
<220> FEATURE:
<221> NAME/KEY: AMIDATION
<222> LOCATION: (39)
<223> OTHER INFORMATION: Ser in position 39 is amidated

<400> SEQUENCE: 1

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35
```

```
<210> SEQ ID NO 2
<211> LENGTH: 39
<212> TYPE: PRT
<213> ORGANISM: Heloderma Suspectum
<220> FEATURE:
<221> NAME/KEY: AMIDATION
<222> LOCATION: (39)
<223> OTHER INFORMATION: Ser in position 39 is amidated

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence

<400> SEQUENCE: 3

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

<400> SEQUENCE: 4

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (30)
<223> OTHER INFORMATION: AMIDATION, Position 30 is Gly-NH2

<400> SEQUENCE: 5

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30
```

```
<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (28)
<223> OTHER INFORMATION: AMIDATION, Position 28 is Asn-NH2

<400> SEQUENCE: 6

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (30)
<223> OTHER INFORMATION: AMIDATION, Position 30 is Gly-NH2

<400> SEQUENCE: 7

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (28)
<223> OTHER INFORMATION: AMIDATION, Position 28 is Asn-NH2

<400> SEQUENCE: 8

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (28)
<223> OTHER INFORMATION: AMIDATION, Position 28 is Asn-NH2
```

```
<400> SEQUENCE: 9

His Gly Glu Gly Thr Phe Thr Ser Asp Leu Ser Lys Gln Leu Glu Glu
1               5                   10                  15

Ala Val Arg Leu Ala Ile Glu Phe Leu Lys Asn
            20                  25

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 10

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
            35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 11

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
            35
```

```
<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 13

Tyr Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Tyr-NH2

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Tyr
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 15

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
```

```
<220> FEATURE:
<221> NAME/KEY: VARIANT
<222> LOCATION: (6)
<223> OTHER INFORMATION: Xaa is naphthylalanine
<220> FEATURE:
<221> NAME/KEY: MOD_RES
<222> LOCATION: (39)
<223> OTHER INFORMATION: AMIDATION, Position 39 is Ser-NH2

<400> SEQUENCE: 16

His Gly Glu Gly Thr Xaa Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 17

His Gly Glu Gly Thr Phe Ser Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 18

His Gly Glu Gly Thr Phe Ser Thr Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2
```

-continued

```
<400> SEQUENCE: 19

His Gly Glu Gly Thr Phe Thr Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 20

His Gly Glu Gly Thr Phe Thr Ser Glu Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2
<220> FEATURE:
<221> NAME/KEY: VARIANT
<222> LOCATION: (10)
<223> OTHER INFORMATION: Xaa is pentylglycine

<400> SEQUENCE: 21

His Gly Glu Gly Thr Phe Thr Ser Asp Xaa Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2
<220> FEATURE:
<221> NAME/KEY: VARIANT
<222> LOCATION: (10)
<223> OTHER INFORMATION: Xaa is pentylglycine
```

-continued

```
<400> SEQUENCE: 22

His Gly Glu Gly Thr Phe Thr Ser Asp Xaa Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2
<220> FEATURE:
<221> NAME/KEY: VARIANT
<222> LOCATION: (14)
<223> OTHER INFORMATION: Xaa is pentylglycine

<400> SEQUENCE: 23

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (14)
<223> OTHER INFORMATION: Xaa is pentylglycine

<400> SEQUENCE: 24

His Gly Glu Gly Thr Phe Thr Ser Asp Leu Ser Lys Gln Xaa Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Postion 39 is Ser-NH2
<220> FEATURE:
<221> NAME/KEY: VARIANT
<222> LOCATION: (22)
<223> OTHER INFORMATION: Xaa is napthylalanine
```

-continued

```
<400> SEQUENCE: 25

His Gly Glu Gly Thr Phe Thr Ser Asp Leu Ser Lys Gln Met Glu Glu
1               5                   10                  15

Glu Ala Val Arg Leu Xaa Ile Glu Trp Leu Lys Asn Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 26

His Gly Glu Gly Thr Phe Thr Ser Asp Leu Ser Lys Gln Met Glu Glu
1               5                   10                  15

Glu Ala Val Arg Leu Phe Val Glu Trp Leu Lys Asn Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 27

His Gly Glu Gly Thr Phe Thr Ser Asp Leu Ser Lys Gln Leu Glu Glu
1               5                   10                  15

Glu Ala Val Arg Leu Phe Val Glu Phe Leu Lys Asn Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 28

His Gly Glu Gly Thr Phe Thr Ser Asp Leu Ser Lys Gln Leu Glu Glu
1               5                   10                  15
```

```
Glu Ala Val Arg Leu Phe Val Glu Phe Leu Lys Asn Gly Gly Pro Ser
            20                  25                  30

Ser Gly Ala Pro Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (23)
<223> OTHER INFORMATION: Xaa at position 23 is tertiary-butylglycine
<220> FEATURE:
<221> NAME/KEY: MOD_RES
<222> LOCATION: (39)
<223> OTHER INFORMATION: AMIDATION, Position 39 is Ser-NH2

<400> SEQUENCE: 29

His Gly Glu Gly Thr Phe Thr Ser Asp Leu Ser Lys Gln Leu Glu Glu
1               5                   10                  15

Glu Ala Val Arg Leu Phe Xaa Glu Phe Leu Lys Asn Gly Gly Pro Ser
            20                  25                  30

Ser Gly Ala Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 30

His Gly Glu Gly Thr Phe Thr Ser Asp Leu Ser Lys Gln Met Glu Glu
1               5                   10                  15

Glu Ala Val Arg Leu Phe Ile Asp Trp Leu Lys Asn Gly Gly Pro Ser
            20                  25                  30

Ser Gly Ala Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: MOD_RES
<222> LOCATION: (39)
<223> OTHER INFORMATION: AMIDATION, Position 39 is Ser-NH2

<400> SEQUENCE: 31

His Ala Glu Gly Thr Phe Thr Ser Asp Leu Ser Lys Gln Leu Glu Glu
1               5                   10                  15
```

```
Glu Ala Val Arg Leu Phe Ile Glu Phe Leu Lys Asn Gly Gly Pro Ser
             20                  25                  30

Ser Gly Ala Pro Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is thioproline
<220> FEATURE:
<221> NAME/KEY: VARIANT
<222> LOCATION: (36)..(38)
<223> OTHER INFORMATION: Xaa at positions 36,37 and 38 is thioproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 32

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
             20                  25                  30

Ser Gly Ala Xaa Xaa Xaa Ser
        35

<210> SEQ ID NO 33
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (36)..(38)
<223> OTHER INFORMATION: Xaa at positions 36, 37, and 38 is thioproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 33

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Xaa Xaa Xaa Ser
        35

<210> SEQ ID NO 34
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is homoproline
```

```
<220> FEATURE:
<221> NAME/KEY: VARIANT
<222> LOCATION: (36)..(38)
<223> OTHER INFORMATION: Xaa at positions 36, 37, and 38 is homoproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 34

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa Ser
         35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (36)..(38)
<223> OTHER INFORMATION: Xaa at positions 36, 37, and 38 is homoproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 35

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa Ser
         35

<210> SEQ ID NO 36
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is thioproline
<220> FEATURE:
<221> NAME/KEY: VARIANT
<222> LOCATION: (36)..(38)
<223> OTHER INFORMATION: Xaa at positions 36,37, and 38 is thioproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 36

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Xaa Ser
            20                  25                  30

Ser Gly Ala Xaa Xaa Xaa Ser
         35
```

```
<210> SEQ ID NO 37
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is homoproline
<220> FEATURE:
<221> NAME/KEY: VARIANT
<222> LOCATION: (36)..(38)
<223> OTHER INFORMATION: Xaa at positions 36,37, and 38 is homoproline
<220> FEATURE:
<221> NAME/KEY: MOD_RES
<222> LOCATION: (39)
<223> OTHER INFORMATION: AMIDATION, Position 39 is Ser-NH2

<400> SEQUENCE: 37

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 38
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is N-methylalanine
<220> FEATURE:
<221> NAME/KEY: VARIANT
<222> LOCATION: (36)..(38)
<223> OTHER INFORMATION: Xaa at positions 36, 37 and 38 is
      N-methylalanine
<220> FEATURE:
<221> NAME/KEY: MOD_RES
<222> LOCATION: (39)
<223> OTHER INFORMATION: AMIDATION, Position 39 is Ser-NH2

<400> SEQUENCE: 38

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35

<210> SEQ ID NO 39
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (36)..(38)
<223> OTHER INFORMATION: Xaa at positions 36, 37, and 38 is
      N-methylalanine
```

```
<220> FEATURE:
<221> NAME/KEY: MOD_RES
<222> LOCATION: (39)
<223> OTHER INFORMATION: AMIDATION, Position 39 is Ser-NH2

<400> SEQUENCE: 39

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa Ser
        35

<210> SEQ ID NO 40
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (31)
<223> OTHER INFORMATION: Xaa at position 31 is N-methylalanine
<220> FEATURE:
<221> NAME/KEY: VARIANT
<222> LOCATION: (36)..(38)
<223> OTHER INFORMATION: Xaa at positions 36, 37, and 38 is
      N-methylalanine
<220> FEATURE:
<221> NAME/KEY: MOD_RES
<222> LOCATION: (39)
<223> OTHER INFORMATION: AMIDATION, Position 39 is Ser-NH2

<400> SEQUENCE: 40

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa at position 1 is His, Arg or Tyr
<220> FEATURE:
<221> NAME/KEY: VARIANT
<222> LOCATION: (2)
<223> OTHER INFORMATION: Xaa at position 2 is Ser, Gly Ala, or Thr
<220> FEATURE:
<221> NAME/KEY: VARIANT
<222> LOCATION: (3)
<223> OTHER INFORMATION: Xaa at position 3 is Ala, Asp or Glu
<220> FEATURE:
<221> NAME/KEY: VARIANT
<222> LOCATION: (5)
<223> OTHER INFORMATION: Xaa at position 5 is Ala or Thr
<220> FEATURE:
<221> NAME/KEY: VARIANT
<222> LOCATION: (6)
<223> OTHER INFORMATION: Xaa at position 6 is Ala, Phe, Tyr or
      napthylalanine
```

```
<220> FEATURE:
<221> NAME/KEY: VARIANT
<222> LOCATION: (7)
<223> OTHER INFORMATION: Xaa at position 7 is Thr or Ser
<220> FEATURE:
<221> NAME/KEY: VARIANT
<222> LOCATION: (8)
<223> OTHER INFORMATION: Xaa at position 8 is Ala, Ser or Thr
<220> FEATURE:
<221> NAME/KEY: VARIANT
<222> LOCATION: (9)
<223> OTHER INFORMATION: Xaa at position 9 is Asp or Glu
<220> FEATURE:
<221> NAME/KEY: VARIANT
<222> LOCATION: (10)
<223> OTHER INFORMATION: Xaa at position 10 is Ala, Leu, Ile, Val,
      pentylglycine, or Met
<220> FEATURE:
<221> NAME/KEY: VARIANT
<222> LOCATION: (11)
<223> OTHER INFORMATION: Xaa at position 11 is Ala or Ser
<220> FEATURE:
<221> NAME/KEY: VARIANT
<222> LOCATION: (12)
<223> OTHER INFORMATION: Xaa at position 12 is Ala or Lys
<220> FEATURE:
<221> NAME/KEY: VARIANT
<222> LOCATION: (13)
<223> OTHER INFORMATION: Xaa at position 13 is Ala or Gln
<220> FEATURE:
<221> NAME/KEY: VARIANT
<222> LOCATION: (14)
<223> OTHER INFORMATION: Xaa at position 14 is Ala, Leu, Ile,
      pentylglycine, Val or Met
<220> FEATURE:
<221> NAME/KEY: VARIANT
<222> LOCATION: (15)
<223> OTHER INFORMATION: Xaa at position 15 is Ala or Glu
<220> FEATURE:
<221> NAME/KEY: VARIANT
<222> LOCATION: (16)..(17)
<223> OTHER INFORMATION: Xaa at position 16 and 17 is Ala or Glu
<220> FEATURE:
<221> NAME/KEY: VARIANT
<222> LOCATION: (19)
<223> OTHER INFORMATION: Xaa at position 19 is Ala or Val
<220> FEATURE:
<221> NAME/KEY: VARIANT
<222> LOCATION: (20)
<223> OTHER INFORMATION: Xaa at position 20 is Ala or Arg
<220> FEATURE:
<221> NAME/KEY: VARIANT
<222> LOCATION: (21)
<223> OTHER INFORMATION: Xaa at position 21 is Ala or Leu
<220> FEATURE:
<221> NAME/KEY: VARIANT
<222> LOCATION: (22)
<223> OTHER INFORMATION: Xaa at position 22 is Ala, Phe, Tyr, or
      naphthylalanine
<220> FEATURE:
<221> NAME/KEY: VARIANT
<222> LOCATION: (23)
<223> OTHER INFORMATION: Xaa at position 23 is Ile, Val, Leu,
      pentylglycine, tert-butylglycine, or Met
<220> FEATURE:
<221> NAME/KEY: VARIANT
<222> LOCATION: (24)
<223> OTHER INFORMATION: Xaa at position 24 is Ala, Glu, or Asp
<220> FEATURE:
<221> NAME/KEY: VARIANT
<222> LOCATION: (25)
<223> OTHER INFORMATION: Xaa at position 25 is Ala, Trp, Phe, Tyr or
      napthylalanine
<220> FEATURE:
<221> NAME/KEY: VARIANT
<222> LOCATION: (26)
<223> OTHER INFORMATION: Xaa at position 26 is Ala or Leu
```

```
<220> FEATURE:
<221> NAME/KEY: VARIANT
<222> LOCATION: (27)
<223> OTHER INFORMATION: Xaa at position 27 is Ala or Lys
<220> FEATURE:
<221> NAME/KEY: VARIANT
<222> LOCATION: (28)
<223> OTHER INFORMATION: Xaa at position 28 is Ala or Asn and is
      optionally amidated
<220> FEATURE:
<221> NAME/KEY: VARIANT
<222> LOCATION: (29)
<223> OTHER INFORMATION: may be absent and if present is optionally
      amidated
<220> FEATURE:
<221> NAME/KEY: VARIANT
<222> LOCATION: (30)
<223> OTHER INFORMATION: may be absent and if present is optionally
      amidated
<220> FEATURE:
<221> NAME/KEY: VARIANT
<222> LOCATION: (31)
<223> OTHER INFORMATION: Xaa at position 31 is Pro, homoproline, 3Hyp,
      4Hyp, thioproline, N-alkylglycine, N-alykylpentylglycine,
      N-alkylalanine or absent and is optionally amidated
<220> FEATURE:
<221> NAME/KEY: VARIANT
<222> LOCATION: (32)
<223> OTHER INFORMATION: may be absent and if present is optionally
      amidated
<220> FEATURE:
<221> NAME/KEY: VARIANT
<222> LOCATION: (33)
<223> OTHER INFORMATION: may be absent and if present is optionally
      amidated
<220> FEATURE:
<221> NAME/KEY: VARIANT
<222> LOCATION: (34)
<223> OTHER INFORMATION: may be absent and if present is optionally
      amidated
<220> FEATURE:
<221> NAME/KEY: VARIANT
<222> LOCATION: (35)
<223> OTHER INFORMATION: may be absent and if present is optionally
      amidated
<220> FEATURE:
<221> NAME/KEY: VARIANT
<222> LOCATION: (36)
<223> OTHER INFORMATION: Xaa at position 36 is Pro, homoproline, 3Hyp,
      4Hyp, thioproline, N-alkylglycine, N-alykylpentylglycine,
      N-alkylalanine or absent and is optionally amidated
<220> FEATURE:
<221> NAME/KEY: VARIANT
<222> LOCATION: (37)
<223> OTHER INFORMATION: Xaa at position 37 is Pro, homoproline, 3Hyp,
      4Hyp, thioproline, N-alkylglycine, N-alykylpentylglycine,
      N-alkylalanine or absent and is optionally amidated
<220> FEATURE:
<221> NAME/KEY: VARIANT
<222> LOCATION: (38)
<223> OTHER INFORMATION: Xaa at position 38 is Pro, homoproline, 3Hyp,
      4Hyp, thioproline, N-alkylglycine, N-alykylpentylglycine,
      N-alkylalanine or absent and is optionally amidated

<400> SEQUENCE: 41

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa
            35

<210> SEQ ID NO 42
<211> LENGTH: 39
<212> TYPE: PRT
<213> ORGANISM: Artificial Sequence
```

-continued

```
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa at position 1 is His, Arg, Tyr, Ala,
      norvaline, Val, or norleucine
<220> FEATURE:
<221> NAME/KEY: VARIANT
<222> LOCATION: (2)
<223> OTHER INFORMATION: Xaa at position 2 is Ser, Gly, Ala, or Thr
<220> FEATURE:
<221> NAME/KEY: VARIANT
<222> LOCATION: (3)
<223> OTHER INFORMATION: Xaa at position 3 is Ala, Asp, or Glu
<220> FEATURE:
<221> NAME/KEY: VARIANT
<222> LOCATION: (4)
<223> OTHER INFORMATION: Xaa at position 4 is Ala, norvaline, Val,
      norleucine or Gly
<220> FEATURE:
<221> NAME/KEY: VARIANT
<222> LOCATION: (5)
<223> OTHER INFORMATION: Xaa at position 5 is Ala or Thr
<220> FEATURE:
<221> NAME/KEY: VARIANT
<222> LOCATION: (6)
<223> OTHER INFORMATION: Xaa at position 6 is Ala, Phe, Tyr, or
      napthylalanine
<220> FEATURE:
<221> NAME/KEY: VARIANT
<222> LOCATION: (7)
<223> OTHER INFORMATION: Xaa at position 7 is Thr or Ser
<220> FEATURE:
<221> NAME/KEY: VARIANT
<222> LOCATION: (8)
<223> OTHER INFORMATION: Xaa at position 8 is Ala, Ser, or Thr
<220> FEATURE:
<221> NAME/KEY: VARIANT
<222> LOCATION: (9)
<223> OTHER INFORMATION: Xaa at position 9 is Ala, norvaline, Val,
      norleucine, Asp or Glu
<220> FEATURE:
<221> NAME/KEY: VARIANT
<222> LOCATION: (10)
<223> OTHER INFORMATION: Xaa at position 10 is Ala, Leu, Ile, Val,
      pentylglycine, or Met
<220> FEATURE:
<221> NAME/KEY: VARIANT
<222> LOCATION: (11)
<223> OTHER INFORMATION: Xaa at position 11 is Ala or Ser
<220> FEATURE:
<221> NAME/KEY: VARIANT
<222> LOCATION: (12)
<223> OTHER INFORMATION: Xaa at position 12 is Ala or Lys
<220> FEATURE:
<221> NAME/KEY: VARIANT
<222> LOCATION: (13)
<223> OTHER INFORMATION: Xaa at position 13 is Ala or Gln
<220> FEATURE:
<221> NAME/KEY: VARIANT
<222> LOCATION: (14)
<223> OTHER INFORMATION: Xaa at position 14 is Ala, Leu, Ile,
      pentylglycine, Val or Met
<220> FEATURE:
<221> NAME/KEY: VARIANT
<222> LOCATION: (15)..(17)
<223> OTHER INFORMATION: Xaa at positions 15, 16, and 17 is Ala or Glu
<220> FEATURE:
<221> NAME/KEY: VARIANT
<222> LOCATION: (19)
<223> OTHER INFORMATION: Xaa at position 19 is Ala or Val
<220> FEATURE:
<221> NAME/KEY: VARIANT
<222> LOCATION: (20)
<223> OTHER INFORMATION: Xaa at position 20 is Ala or Arg
```

```
<220> FEATURE:
<221> NAME/KEY: VARIANT
<222> LOCATION: (21)
<223> OTHER INFORMATION: Xaa at position 21 is Ala or Leu
<220> FEATURE:
<221> NAME/KEY: VARIANT
<222> LOCATION: (22)
<223> OTHER INFORMATION: Xaa at position 22 is Phe, Tyr or
      napthylalanine
<220> FEATURE:
<221> NAME/KEY: VARIANT
<222> LOCATION: (23)
<223> OTHER INFORMATION: Xaa at position 23 is Ile, Val, Leu,
      pentylglycine, tert-butylglycine or Met
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp, Phe, Tyr or
      napthylalanine
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Ala or Lys
<220> FEATURE:
<221> NAME/KEY: VARIANT
<222> LOCATION: (28)
<223> OTHER INFORMATION: Xaa at position 28 is Ala or Asn and is
      optionally amidated
<220> FEATURE:
<221> NAME/KEY: VARIANT
<222> LOCATION: (29)
<223> OTHER INFORMATION: may be absent and is optionally amidated
<220> FEATURE:
<221> NAME/KEY: VARIANT
<222> LOCATION: (30)
<223> OTHER INFORMATION: may be absent and is optionally amidated
<220> FEATURE:
<221> NAME/KEY: VARIANT
<222> LOCATION: (31)
<223> OTHER INFORMATION: Xaa at position 31 is Pro, homoproline, 3Hyp,
      4Hyp, thioproline, N-alkylglycine, N-alkylpentylglycine,
      N-alkylalanine or absent and is optionally amidated
<220> FEATURE:
<221> NAME/KEY: VARIANT
<222> LOCATION: (32)
<223> OTHER INFORMATION: may be absent and is optionally amidated
<220> FEATURE:
<221> NAME/KEY: VARIANT
<222> LOCATION: (33)
<223> OTHER INFORMATION: may be absent and is optionally amidated
<220> FEATURE:
<221> NAME/KEY: VARIANT
<222> LOCATION: (34)
<223> OTHER INFORMATION: may be absent and is optionally amidated
<220> FEATURE:
<221> NAME/KEY: VARIANT
<222> LOCATION: (35)
<223> OTHER INFORMATION: may be absent and is optionally amidated
<220> FEATURE:
<221> NAME/KEY: VARIANT
<222> LOCATION: (36)
<223> OTHER INFORMATION: Xaa at position 36 is Pro, homoproline, 3Hyp,
      4Hyp, thioproline, N-alkylglycine, N-alkylpentylglycine,
      N-alkylalanine or absent and is optionally amidated
<220> FEATURE:
<221> NAME/KEY: VARIANT
<222> LOCATION: (37)
<223> OTHER INFORMATION: Xaa at position 37 is Pro, homoproline, 3Hyp,
      4Hyp, thioproline, N-alkylglycine, N-alkylpentylglycine,
      N-alkylalanine or absent and is optionally amidated
```

```
-continued

<220> FEATURE:
<221> NAME/KEY: VARIANT
<222> LOCATION: (38)
<223> OTHER INFORMATION: Xaa at position 38 is Pro, homoproline, 3Hyp,
      4Hyp, thioproline, N-alkylglycine, N-alkylpentylglycine,
      N-alkylalanine or absent and is optionally amidated
<220> FEATURE:
<221> NAME/KEY: VARIANT
<222> LOCATION: (39)
<223> OTHER INFORMATION: Xaa at position 39 is Ser, Tyr or absent and is
      optionally amidated

<400> SEQUENCE: 42

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Xaa Gly Gly Xaa Ser
            20                  25                  30

Ser Gly Ala Xaa Xaa Xaa Xaa
             35

<210> SEQ ID NO 43
<211> LENGTH: 38
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa at position1 is His or Arg
<220> FEATURE:
<221> NAME/KEY: VARIANT
<222> LOCATION: (2)
<223> OTHER INFORMATION: Xaa at position 2 is Gly or Ala
<220> FEATURE:
<221> NAME/KEY: VARIANT
<222> LOCATION: (3)
<223> OTHER INFORMATION: Xaa at position 3 is Ala, Asp or Glu
<220> FEATURE:
<221> NAME/KEY: VARIANT
<222> LOCATION: (5)
<223> OTHER INFORMATION: Xaa at position 5 is Ala or Thr
<220> FEATURE:
<221> NAME/KEY: VARIANT
<222> LOCATION: (6)
<223> OTHER INFORMATION: Xaa at position 6 is Ala, Phe, or
      napthylalanine
<220> FEATURE:
<221> NAME/KEY: VARIANT
<222> LOCATION: (7)
<223> OTHER INFORMATION: Xaa at position 7 is Ser or Thr
<220> FEATURE:
<221> NAME/KEY: VARIANT
<222> LOCATION: (8)
<223> OTHER INFORMATION: Xaa at position 8 is Ala, Ser, or Thr
<220> FEATURE:
<221> NAME/KEY: VARIANT
<222> LOCATION: (9)
<223> OTHER INFORMATION: Xaa at position 9 is Asp or Glu
<220> FEATURE:
<221> NAME/KEY: VARIANT
<222> LOCATION: (10)
<223> OTHER INFORMATION: Xaa at position 10 is Ala, Leu, or
      pentylglycine
<220> FEATURE:
<221> NAME/KEY: VARIANT
<222> LOCATION: (11)
<223> OTHER INFORMATION: Xaa at position 11 is Ala or Ser
<220> FEATURE:
<221> NAME/KEY: VARIANT
<222> LOCATION: (12)
<223> OTHER INFORMATION: Xaa at position 12 is Ala or Lys
```

```
<220> FEATURE:
<221> NAME/KEY: VARIANT
<222> LOCATION: (13)
<223> OTHER INFORMATION: Xaa at position 13 Ala or Gln
<220> FEATURE:
<221> NAME/KEY: VARIANT
<222> LOCATION: (14)
<223> OTHER INFORMATION: Xaa at position 14 is Ala, Leu or pentylglycine
<220> FEATURE:
<221> NAME/KEY: VARIANT
<222> LOCATION: (15)..(17)
<223> OTHER INFORMATION: Xaa at positions 15, 16, and 17 is Ala or Glu
<220> FEATURE:
<221> NAME/KEY: VARIANT
<222> LOCATION: (19)
<223> OTHER INFORMATION: Xaa at position 19 is Ala or Val
<220> FEATURE:
<221> NAME/KEY: VARIANT
<222> LOCATION: (20)
<223> OTHER INFORMATION: Xaa at position 20 is Ala or Arg
<220> FEATURE:
<221> NAME/KEY: VARIANT
<222> LOCATION: (21)
<223> OTHER INFORMATION: Xaa at position 21 is Ala or Leu
<220> FEATURE:
<221> NAME/KEY: VARIANT
<222> LOCATION: (22)
<223> OTHER INFORMATION: Xaa at position 22 is Phe or napthylalanine
<220> FEATURE:
<221> NAME/KEY: VARIANT
<222> LOCATION: (23)
<223> OTHER INFORMATION: Xaa at position 23 is Ile, Val or
     tert-butylglycine
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp or Phe
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Ala or Lys
<220> FEATURE:
<221> NAME/KEY: VARIANT
<222> LOCATION: (28)
<223> OTHER INFORMATION: Xaa at position 28 is Ala or Asn and is
     optionally amidated
<220> FEATURE:
<221> NAME/KEY: VARIANT
<222> LOCATION: (29)
<223> OTHER INFORMATION: may be absent and is optionally amidated
<220> FEATURE:
<221> NAME/KEY: VARIANT
<222> LOCATION: (30)
<223> OTHER INFORMATION: may be absent and is optionally amidated
<220> FEATURE:
<221> NAME/KEY: VARIANT
<222> LOCATION: (31)
<223> OTHER INFORMATION: Xaa at position 31 is Pro, homoproline,
     thioproline N-methylalanine or absent and is optionally amidated
<220> FEATURE:
<221> NAME/KEY: VARIANT
<222> LOCATION: (32)
<223> OTHER INFORMATION: may be absent and is optionally amidated
<220> FEATURE:
<221> NAME/KEY: VARIANT
<222> LOCATION: (33)
<223> OTHER INFORMATION: may be absent and is optionally amidated
<220> FEATURE:
<221> NAME/KEY: VARIANT
<222> LOCATION: (34)
<223> OTHER INFORMATION: may be absent and is optionally amidated
```

```
<220> FEATURE:
<221> NAME/KEY: VARIANT
<222> LOCATION: (35)
<223> OTHER INFORMATION: may be absent and is optionally amidated
<220> FEATURE:
<221> NAME/KEY: VARIANT
<222> LOCATION: (36)
<223> OTHER INFORMATION: Xaa at position 36 is Pro, homoproline,
      thioproline N-methylalanine or absent and is optionally amidated
<220> FEATURE:
<221> NAME/KEY: VARIANT
<222> LOCATION: (37)
<223> OTHER INFORMATION: Xaa at position 37 is Pro, homoproline,
      thioproline N-methylalanine or absent and is optionally amidated
<220> FEATURE:
<221> NAME/KEY: VARIANT
<222> LOCATION: (38)
<223> OTHER INFORMATION: Xaa at position 38 is Pro, homoproline,
      thioproline N-methylalanine or absent and is optionally amidated

<400> SEQUENCE: 43

Xaa Xaa Xaa Gly Xaa Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa
            35

<210> SEQ ID NO 44
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa in position 1 is His or Ala
<220> FEATURE:
<221> NAME/KEY: VARIANT
<222> LOCATION: (2)
<223> OTHER INFORMATION: Xaa in position 2 is Gly or Ala
<220> FEATURE:
<221> NAME/KEY: VARIANT
<222> LOCATION: (3)
<223> OTHER INFORMATION: Xaa in position 3 is Ala, Asp or Glu
<220> FEATURE:
<221> NAME/KEY: VARIANT
<222> LOCATION: (4)
<223> OTHER INFORMATION: Xaa in position 4 is Ala or Gly
<220> FEATURE:
<221> NAME/KEY: VARIANT
<222> LOCATION: (5)
<223> OTHER INFORMATION: Xaa in position 5 is Ala or Thr
<220> FEATURE:
<221> NAME/KEY: VARIANT
<222> LOCATION: (6)
<223> OTHER INFORMATION: Xaa in position 6 is Ala, Phe or napthylalanine
<220> FEATURE:
<221> NAME/KEY: VARIANT
<222> LOCATION: (7)
<223> OTHER INFORMATION: Xaa in position 7 is Thr or Ser
<220> FEATURE:
<221> NAME/KEY: VARIANT
<222> LOCATION: (8)
<223> OTHER INFORMATION: Xaa in position 8 is Ala, Ser or Thr
<220> FEATURE:
<221> NAME/KEY: VARIANT
<222> LOCATION: (9)
<223> OTHER INFORMATION: Xaa in position 9 is Ala, Asp or Glu
<220> FEATURE:
<221> NAME/KEY: VARIANT
<222> LOCATION: (10)
<223> OTHER INFORMATION: Xaa in position 10 is Ala, Leu or pentylglycine
```

-continued

```
<220> FEATURE:
<221> NAME/KEY: VARIANT
<222> LOCATION: (11)
<223> OTHER INFORMATION: Xaa in position 11 is Ala or Ser
<220> FEATURE:
<221> NAME/KEY: VARIANT
<222> LOCATION: (12)
<223> OTHER INFORMATION: Xaa in position 12 is Ala or Lys
<220> FEATURE:
<221> NAME/KEY: VARIANT
<222> LOCATION: (13)
<223> OTHER INFORMATION: Xaain position 13 is Ala or Gln
<220> FEATURE:
<221> NAME/KEY: VARIANT
<222> LOCATION: (14)
<223> OTHER INFORMATION: Xaa in position 14 is Ala, Leu, Met or
      pentylglycine
<220> FEATURE:
<221> NAME/KEY: VARIANT
<222> LOCATION: (15)..(17)
<223> OTHER INFORMATION: Xaa in positions 15, 16 & 17 is Ala or Glu
<220> FEATURE:
<221> NAME/KEY: VARIANT
<222> LOCATION: (19)
<223> OTHER INFORMATION: Xaa in position 19 is Ala or Val
<220> FEATURE:
<221> NAME/KEY: VARIANT
<222> LOCATION: (20)
<223> OTHER INFORMATION: Xaa in position 20 is Ala or Arg
<220> FEATURE:
<221> NAME/KEY: VARIANT
<222> LOCATION: (21)
<223> OTHER INFORMATION: Xaa in position 21 is Ala or Leu
<220> FEATURE:
<221> NAME/KEY: VARIANT
<222> LOCATION: (22)
<223> OTHER INFORMATION: Xaa at position 22 is Phe or napthylalanine
<220> FEATURE:
<221> NAME/KEY: VARIANT
<222> LOCATION: (23)
<223> OTHER INFORMATION: Xaa at position 23 is Ile, Val or
      tert-butylglycine
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp or Phe
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Ala or Lys
<220> FEATURE:
<221> NAME/KEY: VARIANT
<222> LOCATION: (28)
<223> OTHER INFORMATION: Xaa at position 28 is Ala or Asn and is
      optionally amidated
<220> FEATURE:
<221> NAME/KEY: VARIANT
<222> LOCATION: (29)
<223> OTHER INFORMATION: may be absent and is optionally amidated
<220> FEATURE:
<221> NAME/KEY: VARIANT
<222> LOCATION: (30)
<223> OTHER INFORMATION: may be absent and is optionally amidated
<220> FEATURE:
<221> NAME/KEY: VARIANT
<222> LOCATION: (31)
<223> OTHER INFORMATION: Xaa at position 31 is Pro, homoproline,
      thioproline N-methylalanine or absent and is optionally amidated
<220> FEATURE:
<221> NAME/KEY: VARIANT
<222> LOCATION: (32)
<223> OTHER INFORMATION: may be absent and is optionally amidated
```

```
<220> FEATURE:
<221> NAME/KEY: VARIANT
<222> LOCATION: (33)
<223> OTHER INFORMATION: may be absent and is optionally amidated
<220> FEATURE:
<221> NAME/KEY: VARIANT
<222> LOCATION: (34)
<223> OTHER INFORMATION: may be absent and is optionally amidated
<220> FEATURE:
<221> NAME/KEY: VARIANT
<222> LOCATION: (35)
<223> OTHER INFORMATION: may be absent and is optionally amidated
<220> FEATURE:
<221> NAME/KEY: VARIANT
<222> LOCATION: (36)
<223> OTHER INFORMATION: Xaa at position 36 is Pro, homoproline,
      thioproline N-methylalanine or absent and is optionally amidated
<220> FEATURE:
<221> NAME/KEY: VARIANT
<222> LOCATION: (37)
<223> OTHER INFORMATION: Xaa at position 37 is Pro, homoproline,
      thioproline N-methylalanine or absent and is optionally amidated
<220> FEATURE:
<221> NAME/KEY: VARIANT
<222> LOCATION: (38)
<223> OTHER INFORMATION: Xaa at position 38 is Pro, homoproline,
      thioproline N-methylalanine or absent and is optionally amidated
<220> FEATURE:
<221> NAME/KEY: VARIANT
<222> LOCATION: (39)
<223> OTHER INFORMATION: may be absent and is optionally amidated

<400> SEQUENCE: 44

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Gly Gly Xaa Ser
             20                  25                  30

Ser Gly Ala Xaa Xaa Xaa Ser
         35

<210> SEQ ID NO 45
<211> LENGTH: 38
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa in position 1 is His, Arg, Tyr or
      4-imidazopropionyl
<220> FEATURE:
<221> NAME/KEY: VARIANT
<222> LOCATION: (2)
<223> OTHER INFORMATION: Xaa in positon 2 is Ser, Gly, Ala or Thr
<220> FEATURE:
<221> NAME/KEY: VARIANT
<222> LOCATION: (3)
<223> OTHER INFORMATION: Xaa in position 3 is Ala, Asp or Glu
<220> FEATURE:
<221> NAME/KEY: VARIANT
<222> LOCATION: (5)
<223> OTHER INFORMATION: Xaa in position 5 is Ala or Thr
<220> FEATURE:
<221> NAME/KEY: VARIANT
<222> LOCATION: (6)
<223> OTHER INFORMATION: Xaa in position 6 is Ala, Phe, Tyr or
      napthylalanine
<220> FEATURE:
<221> NAME/KEY: VARIANT
<222> LOCATION: (7)
<223> OTHER INFORMATION: Xaa in position 8 is Thr or Ser
```

```
<220> FEATURE:
<221> NAME/KEY: VARIANT
<222> LOCATION: (8)
<223> OTHER INFORMATION: Xaa in position 8 is Ala, Ser or Thr
<220> FEATURE:
<221> NAME/KEY: VARIANT
<222> LOCATION: (9)
<223> OTHER INFORMATION: Xaa in position 9 is Ala, Asp or Glu
<220> FEATURE:
<221> NAME/KEY: VARIANT
<222> LOCATION: (10)
<223> OTHER INFORMATION: Xaa in position 10 is Ala, Leu, Ile, Val,
      pentylglycine or Met
<220> FEATURE:
<221> NAME/KEY: VARIANT
<222> LOCATION: (11)
<223> OTHER INFORMATION: Xaa in position 11 is Ala or Ser
<220> FEATURE:
<221> NAME/KEY: VARIANT
<222> LOCATION: (12)
<223> OTHER INFORMATION: Xaa in position 12 is Ala or Lys
<220> FEATURE:
<221> NAME/KEY: VARIANT
<222> LOCATION: (13)
<223> OTHER INFORMATION: Xaa in position 13 is Ala or Gln
<220> FEATURE:
<221> NAME/KEY: VARIANT
<222> LOCATION: (14)
<223> OTHER INFORMATION: Xaa in position 14 is Ala, Leu, Ile,
      pentylglycine, Val or Met
<220> FEATURE:
<221> NAME/KEY: VARIANT
<222> LOCATION: (15)..(17)
<223> OTHER INFORMATION: Xaa in positions 15, 16 & 17 is Ala or Glu
<220> FEATURE:
<221> NAME/KEY: VARIANT
<222> LOCATION: (19)
<223> OTHER INFORMATION: Xaa in position 19 is Ala or Val
<220> FEATURE:
<221> NAME/KEY: VARIANT
<222> LOCATION: (20)
<223> OTHER INFORMATION: Xaa in position 20 is Ala or Arg
<220> FEATURE:
<221> NAME/KEY: VARIANT
<222> LOCATION: (21)
<223> OTHER INFORMATION: Xaa in position 21 is Ala, Leu,
      Lys-NH-epsilon-R where R is Lys, Arg, C1-C10 straight chain or
      branched alkanoyl or cycloalkanoyl
<220> FEATURE:
<221> NAME/KEY: VARIANT
<222> LOCATION: (22)
<223> OTHER INFORMATION: Xaa in position 22 is Phe, Tyr, or
      naphthylalanine
<220> FEATURE:
<221> NAME/KEY: VARIANT
<222> LOCATION: (23)
<223> OTHER INFORMATION: Xaa at position 23 is Ile, Val, Leu,
      pentylglycine, tert-butylglycine or Met
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp, Phe, Tyr or
      naphthylalanine
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Lys, Asn, Ala,
      Lys-NH-epsilon-R where R is Lys, Arg, C1-C10 straight chain or
      branched alkanoyl or cycloalkylalkanoyl
```

```
<220> FEATURE:
<221> NAME/KEY: VARIANT
<222> LOCATION: (28)
<223> OTHER INFORMATION: Xaa at position 28 is Lys, Asn, Ala,
      Lys-NH-epsilon-R where R is Lys, Arg, C1-C10 straight chain or
      branched alkanoyl or cycloalkylalkanoyl and is optionally amidated
<220> FEATURE:
<221> NAME/KEY: VARIANT
<222> LOCATION: (29)
<223> OTHER INFORMATION: may be absent and is optionally amidated
<220> FEATURE:
<221> NAME/KEY: VARIANT
<222> LOCATION: (30)
<223> OTHER INFORMATION: may be absent and is optionally amidated
<220> FEATURE:
<221> NAME/KEY: VARIANT
<222> LOCATION: (31)
<223> OTHER INFORMATION: Xaa at position 31 is Pro, homoproline, 3Hyp,
      4Hyp, thioproline, N-alkylglycine, N-alkylpentylglycine
      N-alkylalanine or absent and is optionally amidated
<220> FEATURE:
<221> NAME/KEY: VARIANT
<222> LOCATION: (32)
<223> OTHER INFORMATION: may be absent and is optionally amidated
<220> FEATURE:
<221> NAME/KEY: VARIANT
<222> LOCATION: (33)
<223> OTHER INFORMATION: may be absent and is optionally amidated
<220> FEATURE:
<221> NAME/KEY: VARIANT
<222> LOCATION: (34)
<223> OTHER INFORMATION: may be absent and is optionally amidated
<220> FEATURE:
<221> NAME/KEY: VARIANT
<222> LOCATION: (35)
<223> OTHER INFORMATION: may be absent and is optionally amidated
<220> FEATURE:
<221> NAME/KEY: VARIANT
<222> LOCATION: (36)
<223> OTHER INFORMATION: Xaa at position 36 is Pro, homoproline, 3Hyp,
      4Hyp, thioproline, N-alkylglycine, N-alkylpentylglycine
      N-alkylalanine or absent and is optionally amidated
<220> FEATURE:
<221> NAME/KEY: VARIANT
<222> LOCATION: (37)
<223> OTHER INFORMATION: Xaa at position 37 is Pro, homoproline, 3Hyp,
      4Hyp, thioproline, N-alkylglycine, N-alkylpentylglycine
      N-alkylalanine or absent and is optionally amidated
<220> FEATURE:
<221> NAME/KEY: VARIANT
<222> LOCATION: (38)
<223> OTHER INFORMATION: Xaa at position 38 is Pro, homoproline, 3Hyp,
      4Hyp, thioproline, N-alkylglycine, N-alkylpentylglycine
      N-alkylalanine or absent and is optionally amidated

<400> SEQUENCE: 45

Xaa Xaa Xaa Gly Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Gly Gly Xaa Ser
             20                  25                  30

Ser Gly Ala Xaa Xaa Xaa
         35

<210> SEQ ID NO 46
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa in position 1 is His, Arg, Tyr, Ala,
      norvaline, Val norleucine, or 4-imidazopropionyl
```

```
<220> FEATURE:
<221> NAME/KEY: VARIANT
<222> LOCATION: (2)
<223> OTHER INFORMATION: Xaa in position 2 is Ser, Gly, Ala, or Thr
<220> FEATURE:
<221> NAME/KEY: VARIANT
<222> LOCATION: (3)
<223> OTHER INFORMATION: Xaa in position 3 is Ala, Asp, or Glu
<220> FEATURE:
<221> NAME/KEY: VARIANT
<222> LOCATION: (4)
<223> OTHER INFORMATION: Xaa in position 4 is Ala, norvaline, Val,
      norleucine or Gly
<220> FEATURE:
<221> NAME/KEY: VARIANT
<222> LOCATION: (5)
<223> OTHER INFORMATION: Xaa in position 5 is Ala or Thr
<220> FEATURE:
<221> NAME/KEY: VARIANT
<222> LOCATION: (6)
<223> OTHER INFORMATION: Xaa in position 6 is Ala, Phe, Tyr or
      napthylalanine
<220> FEATURE:
<221> NAME/KEY: VARIANT
<222> LOCATION: (7)
<223> OTHER INFORMATION: Xaa in position 7 is Thr or Ser
<220> FEATURE:
<221> NAME/KEY: VARIANT
<222> LOCATION: (8)
<223> OTHER INFORMATION: Xaa in position 8 is Ala, Ser or Thr
<220> FEATURE:
<221> NAME/KEY: VARIANT
<222> LOCATION: (9)
<223> OTHER INFORMATION: Xaa in position 9 is Ala, Norvaline, Val,
      Norleucine, Asp or Glu
<220> FEATURE:
<221> NAME/KEY: VARIANT
<222> LOCATION: (10)
<223> OTHER INFORMATION: Xaa in position 10 is Ala, Leu, Ile, Val
      pentylglycine or Met
<220> FEATURE:
<221> NAME/KEY: VARIANT
<222> LOCATION: (11)
<223> OTHER INFORMATION: Xaa in position 11 is Ala or Ser
<220> FEATURE:
<221> NAME/KEY: VARIANT
<222> LOCATION: (12)
<223> OTHER INFORMATION: Xaa in position 12 is Ala or Lys
<220> FEATURE:
<221> NAME/KEY: VARIANT
<222> LOCATION: (13)
<223> OTHER INFORMATION: Xaa in position 13 is Ala or Gln
<220> FEATURE:
<221> NAME/KEY: VARIANT
<222> LOCATION: (14)
<223> OTHER INFORMATION: Xaa in position 14 is Ala, Leu, Ile,
      pentylglycine Val or Met
<220> FEATURE:
<221> NAME/KEY: VARIANT
<222> LOCATION: (15)..(17)
<223> OTHER INFORMATION: Xaa in positions 15, 16 & 17 stands for Ala
      or Glu
<220> FEATURE:
<221> NAME/KEY: VARIANT
<222> LOCATION: (19)
<223> OTHER INFORMATION: Xaa in position 19 is Ala or Val
<220> FEATURE:
<221> NAME/KEY: VARIANT
<222> LOCATION: (20)
<223> OTHER INFORMATION: Xaa in position 20 is Ala or Arg
<220> FEATURE:
<221> NAME/KEY: VARIANT
<222> LOCATION: (21)
<223> OTHER INFORMATION: Xaa in position 21 is Ala, Leu or
      Lys-NH-epsilon-R where R is Lys, Arg, C1-C10 straight chain or
      branched alkanoyl or cycloalkyl-alkanoyl
```

```
<220> FEATURE:
<221> NAME/KEY: VARIANT
<222> LOCATION: (22)
<223> OTHER INFORMATION: Xaa at position 22 is Phe, Tyr or
      naphthylalanine
<220> FEATURE:
<221> NAME/KEY: VARIANT
<222> LOCATION: (23)
<223> OTHER INFORMATION: Xaa at position 23 is Ile, Val, Leu,
      pentylglycine, tert-butylglycine or Met
<220> FEATURE:
<221> NAME/KEY: VARIANT
<222> LOCATION: (24)
<223> OTHER INFORMATION: Xaa at position 24 is Ala, Glu or Asp
<220> FEATURE:
<221> NAME/KEY: VARIANT
<222> LOCATION: (25)
<223> OTHER INFORMATION: Xaa at position 25 is Ala, Trp, Phe, Tyr
      or naphthylalanine
<220> FEATURE:
<221> NAME/KEY: VARIANT
<222> LOCATION: (26)
<223> OTHER INFORMATION: Xaa at position 26 is Ala or Leu
<220> FEATURE:
<221> NAME/KEY: VARIANT
<222> LOCATION: (27)
<223> OTHER INFORMATION: Xaa at position 27 is Lys, Asn, Ala,
      Lys-NH-epsilon-R where R is Lys, Arg, C1-C10 straight chain or
      branched alkanoyl or cycloalkylalkanoyl
<220> FEATURE:
<221> NAME/KEY: VARIANT
<222> LOCATION: (28)
<223> OTHER INFORMATION: Xaa at position 28 is Lys, Asn, Ala,
      Lys-NH-epsilon-R where R is Lys, Arg, C1-C10 straight chain or
      branched alkanoyl or cycloalkylalkanoyl and is
      optionally amidated
<220> FEATURE:
<221> NAME/KEY: VARIANT
<222> LOCATION: (29)
<223> OTHER INFORMATION: may be absent and is optionally amidated
<220> FEATURE:
<221> NAME/KEY: VARIANT
<222> LOCATION: (30)
<223> OTHER INFORMATION: may be absent and is optionally amidated
<220> FEATURE:
<221> NAME/KEY: VARIANT
<222> LOCATION: (31)
<223> OTHER INFORMATION: Xaa at position 31 is Pro, homoproline, 3Hyp,
      4Hyp, thioproline, N-alkylglycine, N-alkylpentylglycine,
      N-alkylalanine or absent and is optionally amidated
<220> FEATURE:
<221> NAME/KEY: VARIANT
<222> LOCATION: (32)
<223> OTHER INFORMATION: may be absent and is optionally amidated
<220> FEATURE:
<221> NAME/KEY: VARIANT
<222> LOCATION: (33)
<223> OTHER INFORMATION: may be absent and is optionally amidated
<220> FEATURE:
<221> NAME/KEY: VARIANT
<222> LOCATION: (34)
<223> OTHER INFORMATION: may be absent and is optionally amidated
<220> FEATURE:
<221> NAME/KEY: VARIANT
<222> LOCATION: (35)
<223> OTHER INFORMATION: may be absent and is optionally amidated
<220> FEATURE:
<221> NAME/KEY: VARIANT
<222> LOCATION: (36)
<223> OTHER INFORMATION: Xaa at position 36 is Pro, homoproline, 3Hyp,
      4Hyp, thioproline, N-alkylglycine, N-alkylpentylglycine,
      N-alkylalanine or absent and is optionally amidated
<220> FEATURE:
<221> NAME/KEY: VARIANT
<222> LOCATION: (37)
<223> OTHER INFORMATION: Xaa at position 37 is Pro, homoproline, 3Hyp,
      4Hyp, thioproline N-alkylglycine, N-alkylpentylglycine,
      N-alkylalanine or absent and is optionally amidated
```

```
<220> FEATURE:
<221> NAME/KEY: VARIANT
<222> LOCATION: (38)
<223> OTHER INFORMATION: Xaa at position 38 is Pro, homoproline, 3Hyp,
      4Hyp, thioproline, N-alkylglycine, N-alkylpentylglycine,
      N-alkylalanine or absent and is optionally amidated
<220> FEATURE:
<221> NAME/KEY: VARIANT
<222> LOCATION: (39)
<223> OTHER INFORMATION: Xaa at position 39 is Ser, Tyr or absent and is
      optionally amidated

<400> SEQUENCE: 46

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa Xaa
            35

<210> SEQ ID NO 47
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa in position 1 is His, Arg or Tyr
<220> FEATURE:
<221> NAME/KEY: VARIANT
<222> LOCATION: (2)
<223> OTHER INFORMATION: Xaa in position 2 is Ser, Gly, Ala, or Thr
<220> FEATURE:
<221> NAME/KEY: VARIANT
<222> LOCATION: (3)
<223> OTHER INFORMATION: Xaa in position 3 is Asp or Glu
<220> FEATURE:
<221> NAME/KEY: VARIANT
<222> LOCATION: (6)
<223> OTHER INFORMATION: Xaa in position 6 is Phe, Tyr or naphthalanine
<220> FEATURE:
<221> NAME/KEY: VARIANT
<222> LOCATION: (7)
<223> OTHER INFORMATION: Xaa in position 7 is Thr or Ser
<220> FEATURE:
<221> NAME/KEY: VARIANT
<222> LOCATION: (8)
<223> OTHER INFORMATION: Xaa in position 8 is Ser or Thr
<220> FEATURE:
<221> NAME/KEY: VARIANT
<222> LOCATION: (9)
<223> OTHER INFORMATION: Xaa in position 9 is Asp or Glu
<220> FEATURE:
<221> NAME/KEY: VARIANT
<222> LOCATION: (10)
<223> OTHER INFORMATION: Xaa in position 10 is Leu, Ile, Val,
      pentylglycine or Met
<220> FEATURE:
<221> NAME/KEY: VARIANT
<222> LOCATION: (14)
<223> OTHER INFORMATION: Xaa at position 14 is Leu, Ile, pentylglycine,
      Val or Met
<220> FEATURE:
<221> NAME/KEY: VARIANT
<222> LOCATION: (22)
<223> OTHER INFORMATION: Xaa in position 22 is Phe, Tyr or
      naphthylalanine
<220> FEATURE:
<221> NAME/KEY: VARIANT
<222> LOCATION: (23)
<223> OTHER INFORMATION: Xaa in position 23 is Ile, Val, Leu,
      pentylglycine, tert-butylglycine or Met
```

```
-continued

<220> FEATURE:
<221> NAME/KEY: VARIANT
<222> LOCATION: (24)
<223> OTHER INFORMATION: Xaa in position 24 is Glu or Asp
<220> FEATURE:
<221> NAME/KEY: VARIANT
<222> LOCATION: (25)
<223> OTHER INFORMATION: Xaa in position 25 is Trp, Phe, Tyr or
      naphthylalanine
<220> FEATURE:
<221> NAME/KEY: VARIANT
<222> LOCATION: (31)
<223> OTHER INFORMATION: Xaa in position 31 is Pro, homoproline,
      3-hydroxyproline, 4-hydroxyproline, thioproline,
      N-alkylglycine, N-alkylpentylglycine or N-alkylalanine
<220> FEATURE:
<221> NAME/KEY: VARIANT
<222> LOCATION: (36)..(38)
<223> OTHER INFORMATION: Xaa in positions 36, 37 & 38 is independently
      Pro, homoproline, 3-hydroxyproline, 4-hydroxproline,
      thioproline, N-alkylglycine, N-alkylpentylglycine
      or N-alkylalanine
<220> FEATURE:
<221> NAME/KEY: VARIANT
<222> LOCATION: (39)
<223> OTHER INFORMATION: Xaa in position 39 is Ser, Thr or Tyr and is
      optionally amidated

<400> SEQUENCE: 47

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
            35

<210> SEQ ID NO 48
<211> LENGTH: 39
<212> TYPE: PRT
<213> ORGANISM: Artificial Sequence
<220> FEATURE:
<223> OTHER INFORMATION: Description of Artificial Sequence: Synthetic
      Construct
<220> FEATURE:
<221> NAME/KEY: VARIANT
<222> LOCATION: (1)
<223> OTHER INFORMATION: Xaa in position 1 is His, Arg, Tyr or
      4-imidazopropionyl
<220> FEATURE:
<221> NAME/KEY: VARIANT
<222> LOCATION: (2)
<223> OTHER INFORMATION: Xaa in position 2 is Ser, Gly, Ala or Thr
<220> FEATURE:
<221> NAME/KEY: VARIANT
<222> LOCATION: (3)
<223> OTHER INFORMATION: Xaa in position 3 is Asp or Glu
<220> FEATURE:
<221> NAME/KEY: VARIANT
<222> LOCATION: (6)
<223> OTHER INFORMATION: Xaa in position 6 is Phe, Tyr or
      naphthylalanine
<220> FEATURE:
<221> NAME/KEY: VARIANT
<222> LOCATION: (7)..(8)
<223> OTHER INFORMATION: Xaa in positions 7 & 8 is Thr or Ser
<220> FEATURE:
<221> NAME/KEY: VARIANT
<222> LOCATION: (9)
<223> OTHER INFORMATION: Xaa in position 9 is Asp or Glu
<220> FEATURE:
<221> NAME/KEY: VARIANT
<222> LOCATION: (10)
<223> OTHER INFORMATION: Xaa in position 10 is Leu, Ile, Val,
      pentylglycine or Met
```

```
<220> FEATURE:
<221> NAME/KEY: VARIANT
<222> LOCATION: (14)
<223> OTHER INFORMATION: Xaa at position 14 is Leu, Ile, pentylglycine,
      Val or Met
<220> FEATURE:
<221> NAME/KEY: VARIANT
<222> LOCATION: (22)
<223> OTHER INFORMATION: Xaa in position 22 is Phe, Tyr or
      naphthylalanine
<220> FEATURE:
<221> NAME/KEY: VARIANT
<222> LOCATION: (23)
<223> OTHER INFORMATION: Xaa in position 23 is Ile, Val, Leu,
      pentylglycine, tert-butylglycine or Met
<220> FEATURE:
<221> NAME/KEY: VARIANT
<222> LOCATION: (24)
<223> OTHER INFORMATION: Xaa in position 24 is Glu or Asp
<220> FEATURE:
<221> NAME/KEY: VARIANT
<222> LOCATION: (25)
<223> OTHER INFORMATION: Xaa in position 25 is Trp, Phe, Tyr, or
      naphthylalanine
<220> FEATURE:
<221> NAME/KEY: VARIANT
<222> LOCATION: (27)
<223> OTHER INFORMATION: Xaa at position 27 is Lys, Asn,
      Lys-NH-epsilon-R where R is Lys, Arg, C1-C10 straight chain or
      branched alkanoyl or cycloalkylalkanoyl
<220> FEATURE:
<221> NAME/KEY: VARIANT
<222> LOCATION: (28)
<223> OTHER INFORMATION: Xaa at position 28 is Lys, Asn,
      Lys-NH-epsilon-R where R is Lys, Arg, C1-C10 straight chain or
      branched alkanoyl or cycloalkylalkanoyl
<220> FEATURE:
<221> NAME/KEY: VARIANT
<222> LOCATION: (31)
<223> OTHER INFORMATION: Xaa in position is Pro, homoproline,
      3-hydroxyproline, 4-hydroxyproline, thioproline, N-alkylglycine,
      N-alkylpentylglycine or N-alkylalanine
<220> FEATURE:
<221> NAME/KEY: VARIANT
<222> LOCATION: (36)..(38)
<223> OTHER INFORMATION: Xaa in positions 36-38 is independently Pro,
      homoproline, 3-hydroxyproline, 4-hydroxyproline,
      thioproline, N-alkylglycine, N-alkylpentylglycine
      or N-alkylalanine
<220> FEATURE:
<221> NAME/KEY: VARIANT
<222> LOCATION: (39)
<223> OTHER INFORMATION: Xaa in position 39 is Ser, Thr or Tyr and is
      optionally amidated

<400> SEQUENCE: 48

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Leu Xaa Xaa Gly Gly Xaa Ser
             20                  25                  30

Ser Gly Ala Xaa Xaa Xaa Xaa
         35

<210> SEQ ID NO 49
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated
```

```
<400> SEQUENCE: 49

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly
             20                  25                  30

<210> SEQ ID NO 50
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 50

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn
             20                  25

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 51

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn
             20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 52

His Ala Glu Gly Thr Phe Thr Ser Asp Leu Ser Lys Gln Leu Glu Glu
  1               5                  10                  15

Glu Ala Val Arg Leu Phe Ile Glu Phe Leu Lys Asn
             20                  25

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 53

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 54

His Gly Glu Gly Thr Ala Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 55

His Gly Glu Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 56

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25
```

```
<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 57

His Gly Glu Gly Thr Phe Thr Ser Asp Leu Ala Lys Gln Leu Glu Glu
 1               5                  10                  15

Glu Ala Val Arg Leu Phe Ile Glu Phe Leu Lys Asn
            20                  25

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 58

His Gly Glu Gly Thr Phe Thr Ser Asp Leu Ser Ala Gln Leu Glu Glu
 1               5                  10                  15

Glu Ala Val Arg Leu Phe Ile Glu Phe Leu Lys Asn
            20                  25

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 59

His Gly Glu Gly Thr Phe Thr Ser Asp Leu Ser Lys Ala Leu Glu Glu
 1               5                  10                  15

Glu Ala Val Arg Leu Phe Ile Glu Phe Leu Lys Asn
            20                  25

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated
```

```
<400> SEQUENCE: 60

His Gly Glu Gly Thr Phe Thr Ser Asp Leu Ser Lys Gln Ala Glu Glu
 1               5                  10                  15

Glu Ala Val Arg Leu Phe Ile Glu Phe Leu Lys Asn
            20                  25

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 61

His Gly Glu Gly Thr Phe Thr Ser Asp Leu Ser Lys Gln Leu Ala Glu
 1               5                  10                  15

Glu Ala Val Arg Leu Phe Ile Glu Phe Leu Lys Asn
            20                  25

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 62

His Gly Glu Gly Thr Phe Thr Ser Asp Leu Ser Lys Gln Leu Glu Ala
 1               5                  10                  15

Glu Ala Val Arg Leu Phe Ile Glu Phe Leu Lys Asn
            20                  25

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 63

His Gly Glu Gly Thr Phe Thr Ser Asp Leu Ser Lys Gln Leu Glu Glu
 1               5                  10                  15

Ala Ala Val Arg Leu Phe Ile Glu Phe Leu Lys Asn
            20                  25

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 64

His Gly Glu Gly Thr Phe Thr Ser Asp Leu Ser Lys Gln Leu Glu Glu
 1               5                  10                  15

Glu Ala Ala Arg Leu Phe Ile Glu Phe Leu Lys Asn
            20                  25

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 65

His Gly Glu Gly Thr Phe Thr Ser Asp Leu Ser Lys Gln Leu Glu Glu
 1               5                  10                  15

Glu Ala Val Ala Leu Phe Ile Glu Phe Leu Lys Asn
            20                  25

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 66

His Gly Glu Gly Thr Phe Thr Ser Asp Leu Ser Lys Gln Leu Glu Glu
 1               5                  10                  15

Glu Ala Val Arg Ala Phe Ile Glu Phe Leu Lys Asn
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 67

His Gly Glu Gly Thr Phe Thr Ser Asp Leu Ser Lys Gln Leu Glu Glu
 1               5                  10                  15

Glu Ala Val Arg Leu Phe Ile Ala Phe Leu Lys Asn
            20                  25
```

```
<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 68

His Gly Glu Gly Thr Phe Thr Ser Asp Leu Ser Lys Gln Leu Glu Glu
 1               5                  10                  15

Glu Ala Val Arg Leu Phe Ile Glu Ala Leu Lys Asn
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 69

His Gly Glu Gly Thr Phe Thr Ser Asp Leu Ser Lys Gln Leu Glu Glu
 1               5                  10                  15

Glu Ala Val Arg Leu Phe Ile Glu Phe Ala Lys Asn
            20                  25

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 70

His Gly Glu Gly Thr Phe Thr Ser Asp Leu Ser Lys Gln Leu Glu Glu
 1               5                  10                  15

Glu Ala Val Arg Leu Phe Ile Glu Phe Leu Ala Asn
            20                  25

<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Ala in position 28 is amidated
```

-continued

```
<400> SEQUENCE: 71

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 72
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (38)
<223> OTHER INFORMATION: Pro in position 38 is amidated

<400> SEQUENCE: 72

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 73
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (38)
<223> OTHER INFORMATION: Pro in position 38 is amidated

<400> SEQUENCE: 73

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 74
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (37)
<223> OTHER INFORMATION: Pro in position 37 is amidated

<400> SEQUENCE: 74

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35
```

```
<210> SEQ ID NO 75
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (37)
<223> OTHER INFORMATION: Pro in position 37 is amidated

<400> SEQUENCE: 75

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro
        35

<210> SEQ ID NO 76
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (36)
<223> OTHER INFORMATION: Pro in position 36 is amidated

<400> SEQUENCE: 76

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 77
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (36)
<223> OTHER INFORMATION: Pro in position 36 is amidated

<400> SEQUENCE: 77

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 78
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (35)
<223> OTHER INFORMATION: Ala in position 35 is amidated

<400> SEQUENCE: 78

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 79
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)
<223> OTHER INFORMATION: Ala in position 35 is amidated

<400> SEQUENCE: 79

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala
        35

<210> SEQ ID NO 80
<211> LENGTH: 34
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (34)
<223> OTHER INFORMATION: Gly in position 34 is amidated

<400> SEQUENCE: 80

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly

<210> SEQ ID NO 81
<211> LENGTH: 34
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (34)
<223> OTHER INFORMATION: Gly in position 34 is amidated
```

```
<400> SEQUENCE: 81

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly

<210> SEQ ID NO 82
<211> LENGTH: 33
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (33)
<223> OTHER INFORMATION: Ser in position 33 is amidated

<400> SEQUENCE: 82

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser

<210> SEQ ID NO 83
<211> LENGTH: 33
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (33)
<223> OTHER INFORMATION: Ser in position 33 is amidated

<400> SEQUENCE: 83

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser

<210> SEQ ID NO 84
<211> LENGTH: 32
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (32)
<223> OTHER INFORMATION: Ser in position 32 is amidated

<400> SEQUENCE: 84

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30
```

```
<210> SEQ ID NO 85
<211> LENGTH: 32
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (32)
<223> OTHER INFORMATION: Ser in position 32 is amidated

<400> SEQUENCE: 85

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro Ser
             20                  25                  30

<210> SEQ ID NO 86
<211> LENGTH: 31
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (31)
<223> OTHER INFORMATION: Pro in position 31 is amidated

<400> SEQUENCE: 86

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro
             20                  25                  30

<210> SEQ ID NO 87
<211> LENGTH: 31
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (31)
<223> OTHER INFORMATION: Pro in position 31 is amidated

<400> SEQUENCE: 87

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Pro
             20                  25                  30

<210> SEQ ID NO 88
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated
```

```
<400> SEQUENCE: 88

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 89
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (29)
<223> OTHER INFORMATION: Gly in position 29 is amidated

<400> SEQUENCE: 89

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly
            20                  25

<210> SEQ ID NO 90
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (29)
<223> OTHER INFORMATION: Gly in position 29 is amidated

<400> SEQUENCE: 90

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly
            20                  25

<210> SEQ ID NO 91
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 is tPro
<220> FEATURE:
<221> NAME/KEY: VARIANT
<222> LOCATION: (36)..(38)
<223> OTHER INFORMATION: Xaa in positions 36-38 is tPro
<220> FEATURE:
<221> NAME/KEY: AMIDATION
<222> LOCATION: (38)
<223> OTHER INFORMATION: tPro in postion 38 is amidated

<400> SEQUENCE: 91

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Xaa Ser
            20                  25                  30

Ser Gly Ala Xaa Xaa Xaa
        35

<210> SEQ ID NO 92
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (36)...(38)
<223> OTHER INFORMATION: Xaa in positions 36-38 is tPro
<220> FEATURE:
<221> NAME/KEY: AMIDATION
<222> LOCATION: (38)
<223> OTHER INFORMATION: tPro in position 38 is amidated

<400> SEQUENCE: 92

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa
        35

<210> SEQ ID NO 93
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for Nme
<220> FEATURE:
<221> NAME/KEY: AMIDATION
<222> LOCATION: (37)
<223> OTHER INFORMATION: Pro in position 37 is amidated

<400> SEQUENCE: 93

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Pro Pro
        35

<210> SEQ ID NO 94
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 is Nme
<220> FEATURE:
<221> NAME/KEY: VARIANT
<222> LOCATION: (36)..(37)
<223> OTHER INFORMATION: Xaa in positions 36-37 is Nme
```

```
<220> FEATURE:
<221> NAME/KEY: AMIDATION
<222> LOCATION: (37)
<223> OTHER INFORMATION: Nme in position 37 is amidated

<400> SEQUENCE: 94

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 95
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for hPro
<220> FEATURE:
<221> NAME/KEY: VARIANT
<222> LOCATION: (36)..(37)
<223> OTHER INFORMATION: Xaa in positions 36-37 stands for hPro
<220> FEATURE:
<221> NAME/KEY: AMIDATION
<222> LOCATION: (37)
<223> OTHER INFORMATION: hPro in position 37 is amidated

<400> SEQUENCE: 95

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 96
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for hPro
<220> FEATURE:
<221> NAME/KEY: VARIANT
<222> LOCATION: (36)
<223> OTHER INFORMATION: Xaa in position 36 stands for hPro
<220> FEATURE:
<221> NAME/KEY: AMIDATION
<222> LOCATION: (36)
<223> OTHER INFORMATION: hPro in position 36 is amidated

<400> SEQUENCE: 96

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa
        35
```

```
<210> SEQ ID NO 97
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)
<223> OTHER INFORMATION: Ala in position 35 is amidated

<400> SEQUENCE: 97

Arg Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 98
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

<400> SEQUENCE: 98

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 99
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (6)
<223> OTHER INFORMATION: Xaa in position 6 stands for naph
<220> FEATURE:
<221> NAME/KEY: AMIDATION
<222> LOCATION: (28)
<223> OTHER INFORMATION: Asn in position 28 is amidated

<400> SEQUENCE: 99

His Gly Glu Gly Thr Xaa Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 100
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 100

His Gly Glu Gly Thr Phe Ser Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 101
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 101

His Gly Glu Gly Thr Phe Ser Thr Asp Leu Ser Lys Gln Met Glu Glu
 1               5                  10                  15

Glu Ala Val Arg Leu Phe Ile Glu Trp Leu Lys Asn
            20                  25

<210> SEQ ID NO 102
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 102

His Gly Glu Gly Thr Phe Thr Ser Glu Leu Ser Lys Gln Met Ala Glu
 1               5                  10                  15

Glu Ala Val Arg Leu Phe Ile Glu Trp Leu Lys Asn
            20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (10)
<223> OTHER INFORMATION: Xaa in position 10 stands for pGly
<220> FEATURE:
<221> NAME/KEY: AMIDATION
<222> LOCATION: (28)
<223> OTHER INFORMATION: Asn in position 28 is amidated

<400> SEQUENCE: 103

His Gly Glu Gly Thr Phe Thr Ser Asp Xaa Ser Lys Gln Leu Glu Glu
 1               5                  10                  15

Glu Ala Val Arg Leu Phe Ile Glu Phe Leu Lys Asn
            20                  25
```

```
<210> SEQ ID NO 104
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (22)
<223> OTHER INFORMATION: Xaa in position 22 stands for naph
<220> FEATURE:
<221> NAME/KEY: AMIDATION
<222> LOCATION: (28)
<223> OTHER INFORMATION: Asn in position 28 is amidated

<400> SEQUENCE: 104

His Gly Glu Gly Thr Phe Thr Ser Asp Leu Ser Lys Gln Leu Glu Glu
 1               5                  10                  15

Glu Ala Val Arg Leu Xaa Ile Glu Phe Leu Lys Asn
            20                  25

<210> SEQ ID NO 105
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (23)
<223> OTHER INFORMATION: Xaa in position 23 stands for tBug
<220> FEATURE:
<221> NAME/KEY: AMIDATION
<222> LOCATION: (28)
<223> OTHER INFORMATION: Asn in position 28 is amidated

<400> SEQUENCE: 105

His Gly Glu Gly Thr Phe Thr Ser Asp Leu Ser Lys Gln Met Glu Glu
 1               5                  10                  15

Glu Ala Val Arg Leu Phe Xaa Glu Trp Leu Lys Asn
            20                  25

<210> SEQ ID NO 106
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 106

His Gly Glu Gly Thr Phe Thr Ser Asp Leu Ser Lys Gln Leu Glu Glu
 1               5                  10                  15

Glu Ala Val Arg Leu Phe Ile Asp Phe Leu Lys Asn
            20                  25

<210> SEQ ID NO 107
<211> LENGTH: 33
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (33)
<223> OTHER INFORMATION: Ser in position 33 is amidated

<400> SEQUENCE: 107

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn Gly Gly Pro Ser
            20                  25                  30

Ser

<210> SEQ ID NO 108
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (29)
<223> OTHER INFORMATION: Gly in position 29 is amidated

<400> SEQUENCE: 108

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn Gly
            20                  25

<210> SEQ ID NO 109
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for hPro
<220> FEATURE:
<221> NAME/KEY: VARIANT
<222> LOCATION: (36)..(37)
<223> OTHER INFORMATION: Xaa in positions 36-37 stands for hPro
<220> FEATURE:
<221> NAME/KEY: AMIDATION
<222> LOCATION: (37)
<223> OTHER INFORMATION: hPro in position 37 is amidated

<400> SEQUENCE: 109

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 110
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (27)
<223> OTHER INFORMATION: Asn in position 27 is amidated

<400> SEQUENCE: 110

Xaa Glu Gly Thr Phe Thr Ser Asp Leu Ser Lys Gln Met Glu Glu Glu
 1               5                  10                  15

Ala Val Arg Leu Phe Ile Glu Trp Leu Xaa Asn
            20                  25

<210> SEQ ID NO 111
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (27)
<223> OTHER INFORMATION: Asn in position 27 is amidated

<400> SEQUENCE: 111

Xaa Glu Gly Thr Phe Thr Ser Asp Leu Ser Lys Gln Leu Glu Glu Glu
 1               5                  10                  15

Ala Val Arg Leu Phe Ile Glu Phe Leu Xaa Asn
            20                  25

<210> SEQ ID NO 112
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated
```

-continued

```
<400> SEQUENCE: 112

Xaa Glu Gly Thr Phe Thr Ser Asp Leu Ser Lys Gln Met Glu Glu
 1               5                  10                  15

Ala Val Arg Leu Phe Ile Glu Trp Leu Xaa Asn Gly Gly
            20                  25

<210> SEQ ID NO 113
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 113

Xaa Glu Gly Thr Phe Thr Ser Asp Leu Ser Lys Gln Leu Glu Glu
 1               5                  10                  15

Ala Val Arg Leu Phe Ile Glu Phe Leu Xaa Asn Gly Gly
            20                  25

<210> SEQ ID NO 114
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (27)
<223> OTHER INFORMATION: Lys-NH(epsilon) octanoyl in position 27 is
      amidated

<400> SEQUENCE: 114

Xaa Glu Gly Thr Phe Thr Ser Asp Leu Ser Lys Gln Met Glu Glu
 1               5                  10                  15

Ala Val Arg Leu Phe Ile Glu Trp Leu Asn Xaa
            20                  25

<210> SEQ ID NO 115
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (27)
<223> OTHER INFORMATION: Lys-NH(epsilon) octanoyl in position 27 is
      amidated

<400> SEQUENCE: 115

Xaa Glu Gly Thr Phe Thr Ser Asp Leu Ser Lys Gln Leu Glu Glu Glu
1               5                   10                  15

Ala Val Arg Leu Phe Ile Glu Phe Leu Asn Xaa
            20                  25

<210> SEQ ID NO 116
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 116

Xaa Glu Gly Thr Phe Thr Ser Asp Leu Ser Lys Gln Met Glu Glu Glu
1               5                   10                  15

Ala Val Arg Leu Phe Ile Glu Trp Leu Asn Xaa Gly Gly
            20                  25

<210> SEQ ID NO 117
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (29)
<223> OTHER INFORMATION: Gly in postion 29 is amidated
```

```
<400> SEQUENCE: 117

Xaa Glu Gly Thr Phe Thr Ser Asp Leu Ser Lys Gln Leu Glu Glu
 1               5                  10                  15

Ala Val Arg Leu Phe Ile Glu Phe Leu Asn Xaa Gly Gly
            20                  25

<210> SEQ ID NO 118
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 118

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 119
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 119

His Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 120
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 120

His Gly Glu Ala Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 121
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 121

His Gly Glu Gly Thr Phe Thr Ser Ala Leu Ser Lys Gln Leu Glu Glu
1               5                   10                  15

Glu Ala Val Arg Leu Phe Ile Glu Phe Leu Lys Asn
            20                  25

<210> SEQ ID NO 122
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 122

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 123
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 123

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 124
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 124

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn
            20                  25
```

```
<210> SEQ ID NO 125
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 125

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn
            20                  25

<210> SEQ ID NO 126
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 126

His Gly Glu Gly Thr Phe Thr Ser Asp Ala Ser Lys Gln Met Glu Glu
 1               5                  10                  15

Glu Ala Val Arg Leu Phe Ile Glu Trp Leu Lys Asn
            20                  25

<210> SEQ ID NO 127
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 127

Ala Ala Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 128
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated
```

```
<400> SEQUENCE: 128

Ala Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 129
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 129

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 130
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 130

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 131

Ala Gly Asp Gly Ala Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 132
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 132

Ala Gly Asp Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 133
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (6)
<223> OTHER INFORMATION: Xaa in position 6 stands for Nala
<220> FEATURE:
<221> NAME/KEY: AMIDATION
<222> LOCATION: (28)
<223> OTHER INFORMATION: Asn in position 28 is amidated

<400> SEQUENCE: 133

Ala Gly Asp Gly Thr Xaa Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 134
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (6)
<223> OTHER INFORMATION: Xaa in position 6 stands for Nala
<220> FEATURE:
<221> NAME/KEY: AMIDATION
<222> LOCATION: (28)
<223> OTHER INFORMATION: Asn in position 28 is amidated

<400> SEQUENCE: 134

Ala Gly Asp Gly Thr Xaa Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 135
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated
```

```
<400> SEQUENCE: 135

Ala Gly Asp Gly Thr Phe Ser Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 136
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 136

Ala Gly Asp Gly Thr Phe Ser Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 137
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 137

Ala Gly Asp Gly Thr Phe Thr Ala Asp Leu Ser Lys Gln Met Glu Glu
1               5                   10                  15

Glu Ala Val Arg Leu Phe Ile Glu Trp Leu Lys Asn
            20                  25

<210> SEQ ID NO 138
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 138

Ala Gly Asp Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 139
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 139

Ala Gly Asp Gly Thr Phe Thr Ser Ala Leu Ser Lys Gln Met Glu Glu
1               5                   10                  15

Glu Ala Val Arg Leu Phe Ile Glu Trp Leu Lys Asn
            20                  25

<210> SEQ ID NO 140
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 140

Ala Gly Asp Gly Thr Phe Thr Ser Ala Leu Ser Lys Gln Leu Glu Glu
1               5                   10                  15

Glu Ala Val Arg Leu Phe Ile Glu Phe Leu Lys Asn
            20                  25

<210> SEQ ID NO 141
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 141

Ala Gly Asp Gly Thr Phe Thr Ser Glu Leu Ser Lys Gln Met Glu Glu
1               5                   10                  15

Glu Ala Val Arg Leu Phe Ile Glu Trp Leu Lys Asn
            20                  25

<210> SEQ ID NO 142
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 142

Ala Gly Asp Gly Thr Phe Thr Ser Glu Leu Ser Lys Gln Leu Glu Glu
1               5                   10                  15

Glu Ala Val Arg Leu Phe Ile Glu Phe Leu Lys Asn
            20                  25
```

```
<210> SEQ ID NO 143
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 143

Ala Gly Asp Gly Thr Phe Thr Ser Asp Ala Ser Lys Gln Met Glu Glu
 1               5                  10                  15

Glu Ala Val Arg Leu Phe Ile Glu Trp Leu Lys Asn
            20                  25

<210> SEQ ID NO 144
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 144

Ala Gly Asp Gly Thr Phe Thr Ser Asp Ala Ser Lys Gln Leu Glu Glu
 1               5                  10                  15

Glu Ala Val Arg Leu Phe Ile Glu Phe Leu Lys Asn
            20                  25

<210> SEQ ID NO 145
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (10)
<223> OTHER INFORMATION: Xaa in position 10 stands for Pgly
<220> FEATURE:
<221> NAME/KEY: AMIDATION
<222> LOCATION: (28)
<223> OTHER INFORMATION: Asn in position 28 is amidated

<400> SEQUENCE: 145

Ala Gly Asp Gly Thr Phe Thr Ser Asp Xaa Ser Lys Gln Met Glu Glu
 1               5                  10                  15

Glu Ala Val Arg Leu Phe Ile Glu Trp Leu Lys Asn
            20                  25

<210> SEQ ID NO 146
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (10)
<223> OTHER INFORMATION: Xaa in position 10 stands for Pgly
```

```
<220> FEATURE:
<221> NAME/KEY: AMIDATION
<222> LOCATION: (28)
<223> OTHER INFORMATION: Asn in position 28 is amidated

<400> SEQUENCE: 146

Ala Gly Asp Gly Thr Phe Thr Ser Asp Xaa Ser Lys Gln Leu Glu Glu
1               5                   10                  15

Glu Ala Val Arg Leu Phe Ile Glu Phe Leu Lys Asn
            20                  25

<210> SEQ ID NO 147
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 147

Ala Gly Asp Gly Thr Phe Thr Ser Asp Leu Ala Lys Gln Met Glu Glu
1               5                   10                  15

Glu Ala Val Arg Leu Phe Ile Glu Trp Leu Lys Asn
            20                  25

<210> SEQ ID NO 148
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 148

Ala Gly Asp Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 149
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 149

Ala Gly Asp Gly Thr Phe Thr Ser Asp Leu Ser Ala Gln Met Glu Glu
1               5                   10                  15

Glu Ala Val Arg Leu Phe Ile Glu Trp Leu Lys Asn
            20                  25
```

```
<210> SEQ ID NO 150
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 150

Ala Gly Asp Gly Thr Phe Thr Ser Asp Leu Ser Ala Gln Leu Glu Glu
 1               5                  10                  15

Glu Ala Val Arg Leu Phe Ile Glu Phe Leu Lys Asn
            20                  25

<210> SEQ ID NO 151
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 151

Ala Gly Asp Gly Thr Phe Thr Ser Asp Leu Ser Lys Ala Met Glu Glu
 1               5                  10                  15

Glu Ala Val Arg Leu Phe Ile Glu Trp Leu Lys Asn
            20                  25

<210> SEQ ID NO 152
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 152

Ala Gly Asp Gly Thr Phe Thr Ser Asp Leu Ser Lys Ala Leu Glu Glu
 1               5                  10                  15

Glu Ala Val Arg Leu Phe Ile Glu Phe Leu Lys Asn
            20                  25

<210> SEQ ID NO 153
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated
```

-continued

```
<400> SEQUENCE: 153

Ala Gly Asp Gly Thr Phe Thr Ser Asp Leu Ser Lys Gln Ala Glu Glu
1               5                   10                  15

Glu Ala Val Arg Leu Phe Ile Glu Trp Leu Lys Asn
            20                  25

<210> SEQ ID NO 154
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 154

Ala Gly Asp Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 155
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (14)
<223> OTHER INFORMATION: Xaa in position 14 stands for pGly
<220> FEATURE:
<221> NAME/KEY: AMIDATION
<222> LOCATION: (28)
<223> OTHER INFORMATION: Asn in position 28 is amidated

<400> SEQUENCE: 155

Ala Gly Asp Gly Thr Phe Thr Ser Asp Leu Ser Lys Gln Xaa Glu Glu
1               5                   10                  15

Glu Ala Val Arg Leu Phe Ile Glu Trp Leu Lys Asn
            20                  25

<210> SEQ ID NO 156
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (14)
<223> OTHER INFORMATION: Xaa in position 14 stands for pGly
<220> FEATURE:
<221> NAME/KEY: AMIDATION
<222> LOCATION: (28)
<223> OTHER INFORMATION: Asn in position 28 is amidated

<400> SEQUENCE: 156

Ala Gly Asp Gly Thr Phe Thr Ser Asp Leu Ser Lys Gln Xaa Glu Glu
1               5                   10                  15

Glu Ala Val Arg Leu Phe Ile Glu Phe Leu Lys Asn
            20                  25
```

```
<210> SEQ ID NO 157
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 157

Ala Gly Asp Gly Thr Phe Thr Ser Asp Leu Ser Lys Gln Met Ala Glu
 1               5                  10                  15

Glu Ala Val Arg Leu Phe Ile Glu Trp Leu Lys Asn
            20                  25

<210> SEQ ID NO 158
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 158

Ala Gly Asp Gly Thr Phe Thr Ser Asp Leu Ser Lys Gln Leu Ala Glu
 1               5                  10                  15

Glu Ala Val Arg Leu Phe Ile Glu Phe Leu Lys Asn
            20                  25

<210> SEQ ID NO 159
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 159

Ala Gly Asp Gly Thr Phe Thr Ser Asp Leu Ser Lys Gln Met Glu Ala
 1               5                  10                  15

Glu Ala Val Arg Leu Phe Ile Glu Trp Leu Lys Asn
            20                  25

<210> SEQ ID NO 160
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated
```

-continued

```
<400> SEQUENCE: 160

Ala Gly Asp Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 161
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 161

Ala Gly Asp Gly Thr Phe Thr Ser Asp Leu Ser Lys Gln Met Glu Glu
1               5                   10                  15

Ala Ala Val Arg Leu Phe Ile Glu Trp Leu Lys Asn
            20                  25

<210> SEQ ID NO 162
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 162

Ala Gly Asp Gly Thr Phe Thr Ser Asp Leu Ser Lys Gln Leu Glu Glu
1               5                   10                  15

Ala Ala Val Arg Leu Phe Ile Glu Phe Leu Lys Asn
            20                  25

<210> SEQ ID NO 163
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 163

Ala Gly Asp Gly Thr Phe Thr Ser Asp Leu Ser Lys Gln Met Glu Glu
1               5                   10                  15

Glu Ala Ala Arg Leu Phe Ile Glu Trp Leu Lys Asn
            20                  25

<210> SEQ ID NO 164
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 164

Ala Gly Asp Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 165
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 165

Ala Gly Asp Gly Thr Phe Thr Ser Asp Leu Ser Lys Gln Met Glu Glu
1               5                   10                  15

Glu Ala Val Ala Leu Phe Ile Glu Trp Leu Lys Asn
            20                  25

<210> SEQ ID NO 166
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 166

Ala Gly Asp Gly Thr Phe Thr Ser Asp Leu Ser Lys Gln Leu Glu Glu
1               5                   10                  15

Glu Ala Val Ala Leu Phe Ile Glu Phe Leu Lys Asn
            20                  25

<210> SEQ ID NO 167
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 167

Ala Gly Asp Gly Thr Phe Thr Ser Asp Leu Ser Lys Gln Met Glu Glu
1               5                   10                  15

Glu Ala Val Arg Ala Phe Ile Glu Trp Leu Lys Asn
            20                  25
```

```
<210> SEQ ID NO 168
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 168

Ala Gly Asp Gly Thr Phe Thr Ser Asp Leu Ser Lys Gln Leu Glu Glu
 1               5                  10                  15

Glu Ala Val Arg Ala Phe Ile Glu Phe Leu Lys Asn
            20                  25

<210> SEQ ID NO 169
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (22)
<223> OTHER INFORMATION: Xaa in position 22 stands for Nala
<220> FEATURE:
<221> NAME/KEY: AMIDATION
<222> LOCATION: (28)
<223> OTHER INFORMATION: Asn in position 28 is amidated

<400> SEQUENCE: 169

Ala Gly Asp Gly Thr Phe Thr Ser Asp Leu Ser Lys Gln Met Glu Glu
 1               5                  10                  15

Glu Ala Val Arg Leu Xaa Ile Glu Trp Leu Lys Asn
            20                  25

<210> SEQ ID NO 170
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (22)
<223> OTHER INFORMATION: Xaa in position 22 stands for Nala
<220> FEATURE:
<221> NAME/KEY: AMIDATION
<222> LOCATION: (28)
<223> OTHER INFORMATION: Asn in position 28 is amidated

<400> SEQUENCE: 170

Ala Gly Asp Gly Thr Phe Thr Ser Asp Leu Ser Lys Gln Leu Glu Glu
 1               5                  10                  15

Glu Ala Val Arg Leu Xaa Ile Glu Phe Leu Lys Asn
            20                  25

<210> SEQ ID NO 171
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 171

Ala Gly Asp Gly Thr Phe Thr Ser Asp Leu Ser Lys Gln Met Glu Glu
1               5                   10                  15

Glu Ala Val Arg Leu Phe Val Glu Trp Leu Lys Asn
            20                  25

<210> SEQ ID NO 172
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 172

Ala Gly Asp Gly Thr Phe Thr Ser Asp Leu Ser Lys Gln Leu Glu Glu
1               5                   10                  15

Glu Ala Val Arg Leu Phe Val Glu Phe Leu Lys Asn
            20                  25

<210> SEQ ID NO 173
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (23)
<223> OTHER INFORMATION: Xaa in position 23 stands for tGly
<220> FEATURE:
<221> NAME/KEY: AMIDATION
<222> LOCATION: (28)
<223> OTHER INFORMATION: Asn in position 28 is amidated

<400> SEQUENCE: 173

Ala Gly Asp Gly Thr Phe Thr Ser Asp Leu Ser Lys Gln Met Glu Glu
1               5                   10                  15

Glu Ala Val Arg Leu Phe Xaa Glu Trp Leu Lys Asn
            20                  25

<210> SEQ ID NO 174
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (23)
<223> OTHER INFORMATION: Xaa in position 23 stands for tGly
<220> FEATURE:
<221> NAME/KEY: AMIDATION
<222> LOCATION: (28)
<223> OTHER INFORMATION: Asn in position 28 is amidated
```

```
<400> SEQUENCE: 174

Ala Gly Asp Gly Thr Phe Thr Ser Asp Leu Ser Lys Gln Leu Glu Glu
1               5                   10                  15

Glu Ala Val Arg Leu Phe Xaa Glu Phe Leu Lys Asn
            20                  25

<210> SEQ ID NO 175
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 175

Ala Gly Asp Gly Thr Phe Thr Ser Asp Leu Ser Lys Gln Met Glu Glu
1               5                   10                  15

Glu Ala Val Arg Leu Phe Ile Asp Trp Leu Lys Asn
            20                  25

<210> SEQ ID NO 176
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 176

Ala Gly Asp Gly Thr Phe Thr Ser Asp Leu Ser Lys Gln Leu Glu Glu
1               5                   10                  15

Glu Ala Val Arg Leu Phe Ile Asp Phe Leu Lys Asn
            20                  25

<210> SEQ ID NO 177
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 177

Ala Gly Asp Gly Thr Phe Thr Ser Asp Leu Ser Lys Gln Met Glu Glu
1               5                   10                  15

Glu Ala Val Arg Leu Phe Ile Glu Ala Leu Lys Asn
            20                  25

<210> SEQ ID NO 178
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: AMIDATION
<222> LOCATION: (28)
<223> OTHER INFORMATION: Asn in position 28 is amidated

<400> SEQUENCE: 178

Ala Gly Asp Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 179
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 179

Ala Gly Asp Gly Thr Phe Thr Ser Asp Leu Ser Lys Gln Met Glu Glu
1               5                   10                  15

Glu Ala Val Arg Leu Phe Ile Glu Trp Ala Lys Asn
            20                  25

<210> SEQ ID NO 180
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 180

Ala Gly Asp Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 181
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 181

Ala Gly Asp Gly Thr Phe Thr Ser Asp Leu Ser Lys Gln Met Glu Glu
1               5                   10                  15

Glu Ala Val Arg Leu Phe Ile Glu Trp Leu Ala Asn
            20                  25
```

```
<210> SEQ ID NO 182
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Asn in position 28 is amidated

<400> SEQUENCE: 182

Ala Gly Asp Gly Thr Phe Thr Ser Asp Leu Ser Lys Gln Leu Glu Glu
 1               5                  10                  15

Glu Ala Val Arg Leu Phe Ile Glu Phe Leu Ala Asn
             20                  25

<210> SEQ ID NO 183
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Ala in position 28 is amidated

<400> SEQUENCE: 183

Ala Gly Asp Gly Thr Phe Thr Ser Asp Leu Ser Lys Gln Met Glu Glu
 1               5                  10                  15

Glu Ala Val Arg Leu Phe Ile Glu Trp Leu Lys Ala
             20                  25

<210> SEQ ID NO 184
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (28)
<223> OTHER INFORMATION: Ala in position 28 is amidated

<400> SEQUENCE: 184

Ala Gly Asp Gly Thr Phe Thr Ser Asp Leu Ser Lys Gln Leu Glu Glu
 1               5                  10                  15

Glu Ala Val Arg Leu Phe Ile Glu Phe Leu Lys Ala
             20                  25

<210> SEQ ID NO 185
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (38)
<223> OTHER INFORMATION: Pro in position 38 is amidated
```

<400> SEQUENCE: 185

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 186
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (38)
<223> OTHER INFORMATION: Pro in position 38 is amidated

<400> SEQUENCE: 186

His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 187
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (37)
<223> OTHER INFORMATION: Pro in position 37 is amidated

<400> SEQUENCE: 187

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 188
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (36)
<223> OTHER INFORMATION: Pro in position 36 is amidated

<400> SEQUENCE: 188

His Gly Glu Gly Thr Phe Thr Ser Ala Leu Ser Lys Gln Met Glu Glu
1               5                   10                  15

```
Glu Ala Val Arg Leu Phe Ile Glu Trp Leu Lys Asn Gly Gly Pro Ser
            20                  25                  30

Ser Gly Ala Pro
        35
```

<210> SEQ ID NO 189
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (36)
<223> OTHER INFORMATION: Pro in position 36 is amidated

<400> SEQUENCE: 189

```
Ala Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro
        35
```

<210> SEQ ID NO 190
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)
<223> OTHER INFORMATION: Ala in position 35 is amidated

<400> SEQUENCE: 190

```
Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35
```

<210> SEQ ID NO 191
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)
<223> OTHER INFORMATION: Ala in position 35 is amidated

<400> SEQUENCE: 191

```
His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala
        35
```

```
<210> SEQ ID NO 192
<211> LENGTH: 34
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (34)
<223> OTHER INFORMATION: Gly in position 34 is amidated

<400> SEQUENCE: 192

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly

<210> SEQ ID NO 193
<211> LENGTH: 33
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (33)
<223> OTHER INFORMATION: Ser in position 33 is amidated

<400> SEQUENCE: 193

His Gly Glu Gly Thr Phe Thr Ser Ala Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser

<210> SEQ ID NO 194
<211> LENGTH: 32
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (32)
<223> OTHER INFORMATION: Ser in position 32 is amidated

<400> SEQUENCE: 194

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (32)
<223> OTHER INFORMATION: Ser in position 32 is amidated
```

```
<400> SEQUENCE: 195

His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

<210> SEQ ID NO 196
<211> LENGTH: 31
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (31)
<223> OTHER INFORMATION: Pro in position 31 is amidated

<400> SEQUENCE: 196

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 197
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

<400> SEQUENCE: 197

His Gly Glu Gly Thr Phe Thr Ser Ala Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 198
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (29)
<223> OTHER INFORMATION: Gly in position 29 is amidated

<400> SEQUENCE: 198

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly
            20                  25

<210> SEQ ID NO 199
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: VARIANT
<222> LOCATION: (31)
<223> OTHER INFORMATION: Xaa in position 31 stands for tPro
<220> FEATURE:
<221> NAME/KEY: VARIANT
<222> LOCATION: (36)..(38)
<223> OTHER INFORMATION: Xaa in positions 36-38 stands for tPro
<220> FEATURE:
<221> NAME/KEY: AMIDATION
<222> LOCATION: (38)
<223> OTHER INFORMATION: tPro in position 38 is amidated

<400> SEQUENCE: 199

His Gly Ala Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa Xaa Xaa
            35

<210> SEQ ID NO 200
<211> LENGTH: 38
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (36)..(38)
<223> OTHER INFORMATION: Xaa in positions 36-38 stands for tPro
<220> FEATURE:
<221> NAME/KEY: AMIDATION
<222> LOCATION: (38)
<223> OTHER INFORMATION: tPro in position 38 is amidated

<400> SEQUENCE: 200

His Gly Glu Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Xaa Xaa Xaa
            35

<210> SEQ ID NO 201
<211> LENGTH: 37
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for Nme
<220> FEATURE:
<221> NAME/KEY: VARIANT
<222> LOCATION: (36)..(37)
<223> OTHER INFORMATION: Xaa in positions 36-37 stands for Nme
<220> FEATURE:
<221> NAME/KEY: AMIDATION
<222> LOCATION: (37)
<223> OTHER INFORMATION: Nme in position 37 is amidated

<400> SEQUENCE: 201

His Gly Glu Gly Thr Phe Thr Ser Ala Leu Ser Lys Gln Met Glu Glu
 1               5                  10                  15
```

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 202
<211> LENGTH: 36
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (31)
<223> OTHER INFORMATION: Xaa in position 31 stands for hPro
<220> FEATURE:
<221> NAME/KEY: VARIANT
<222> LOCATION: (36)
<223> OTHER INFORMATION: Xaa in position 36 stands for hPro
<220> FEATURE:
<221> NAME/KEY: AMIDATION
<222> LOCATION: (36)
<223> OTHER INFORMATION: hPro in position 36 is amidated

<400> SEQUENCE: 202

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Xaa Ser
            20                  25                  30

Ser Gly Ala Xaa
        35

<210> SEQ ID NO 203
<211> LENGTH: 35
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (35)
<223> OTHER INFORMATION: Ala in position 35 is amidated

<400> SEQUENCE: 203

His Gly Ala Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala
        35

<210> SEQ ID NO 204
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (30)
<223> OTHER INFORMATION: Gly in position 30 is amidated

```
<400> SEQUENCE: 204

His Gly Asp Ala Thr Phe Thr Ser Asp Leu Ser Lys Gln Met Glu Glu
 1               5                  10                  15

Glu Ala Val Arg Leu Phe Ile Glu Trp Leu Lys Asn Gly Gly
             20                  25                  30

<210> SEQ ID NO 205
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (39)
<223> OTHER INFORMATION: Ser in position 39 is amidated

<400> SEQUENCE: 205

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Pro Ser
            35

<210> SEQ ID NO 206
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: AMIDATION
<222> LOCATION: (39)
<223> OTHER INFORMATION: Ser in position 39 is amidated

<400> SEQUENCE: 206

Ala Gly Ala Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
             20                  25                  30

Ser Gly Ala Pro Pro Pro Ser
            35

<210> SEQ ID NO 207
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (27)
<223> OTHER INFORMATION: Asn in position 27 is amidated
```

```
<400> SEQUENCE: 207

Xaa Glu Gly Thr Phe Thr Ser Ala Leu Ser Lys Gln Met Glu Glu
 1               5                  10                  15

Ala Val Arg Leu Phe Ile Glu Trp Leu Xaa Asn
            20                  25

<210> SEQ ID NO 208
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (27)
<223> OTHER INFORMATION: Asn in position 27 is amidated

<400> SEQUENCE: 208

Xaa Glu Gly Thr Phe Thr Ser Ala Leu Ser Lys Gln Leu Glu Glu
 1               5                  10                  15

Ala Val Arg Leu Phe Ile Glu Phe Leu Xaa Asn
            20                  25

<210> SEQ ID NO 209
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 209

Xaa Glu Gly Thr Phe Thr Ser Ala Leu Ser Lys Gln Met Glu Glu
 1               5                  10                  15

Ala Val Arg Leu Phe Ile Glu Trp Leu Xaa Asn Gly Gly
            20                  25

<210> SEQ ID NO 210
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (26)
<223> OTHER INFORMATION: Xaa in position 26 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 210

Xaa Glu Gly Thr Phe Thr Ser Ala Leu Ser Lys Gln Leu Glu Glu Glu
 1               5                  10                  15

Ala Val Arg Leu Phe Ile Glu Phe Leu Xaa Asn Gly Gly
                20                  25

<210> SEQ ID NO 211
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (27)
<223> OTHER INFORMATION: Lys-NH(epsilon) octanoyl in position 27 is
      amidated

<400> SEQUENCE: 211

Xaa Glu Gly Thr Phe Thr Ser Ala Leu Ser Lys Gln Met Glu Glu Glu
 1               5                  10                  15

Ala Val Arg Leu Phe Ile Glu Trp Leu Asn Xaa
                20                  25

<210> SEQ ID NO 212
<211> LENGTH: 27
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (27)
<223> OTHER INFORMATION: Lys-NH(epsilon) octanoyl
```

-continued

```
<400> SEQUENCE: 212

Xaa Glu Gly Thr Phe Thr Ser Ala Leu Ser Lys Gln Leu Glu Glu Glu
 1               5                  10                  15

Ala Val Arg Leu Phe Ile Glu Phe Leu Asn Xaa
            20                  25

<210> SEQ ID NO 213
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in positon 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 213

Xaa Glu Gly Thr Phe Thr Ser Ala Leu Ser Lys Gln Met Glu Glu Glu
 1               5                  10                  15

Ala Val Arg Leu Phe Ile Glu Trp Leu Asn Xaa Gly Gly
            20                  25

<210> SEQ ID NO 214
<211> LENGTH: 29
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (1)
<223> OTHER INFORMATION: Xaa in position 1 stands for
      4-Imidazolylpropionyl-Gly
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (29)
<223> OTHER INFORMATION: Gly in position 29 is amidated

<400> SEQUENCE: 214

Xaa Glu Gly Thr Phe Thr Ser Ala Leu Ser Lys Gln Leu Glu Glu Glu
 1               5                  10                  15

Ala Val Arg Leu Phe Ile Glu Phe Leu Asn Xaa Gly Gly
            20                  25

<210> SEQ ID NO 215
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
```

-continued

```
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (28)
<223> OTHER INFORMATION: Asn in position 28 is amidated

<400> SEQUENCE: 215

Ala Gly Glu Gly Thr Phe Thr Ser Asp Leu Ser Lys Gln Met Glu Glu
 1               5                   10                  15

Glu Ala Val Arg Leu Phe Ile Glu Trp Leu Xaa Asn
            20                  25

<210> SEQ ID NO 216
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (28)
<223> OTHER INFORMATION: Asn in position 28 is amidated

<400> SEQUENCE: 216

Ala Gly Glu Gly Thr Phe Thr Ser Asp Leu Ser Lys Gln Leu Glu Glu
 1               5                   10                  15

Glu Ala Val Arg Leu Phe Ile Glu Phe Leu Xaa Asn
            20                  25

<210> SEQ ID NO 217
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (30)
<223> OTHER INFORMATION: Gly in position 30 is amidated

<400> SEQUENCE: 217

Ala Gly Glu Gly Thr Phe Thr Ser Asp Leu Ser Lys Gln Met Glu Glu
 1               5                   10                  15

Glu Ala Val Arg Leu Phe Ile Glu Trp Leu Xaa Asn Gly Gly
            20                  25                  30

<210> SEQ ID NO 218
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: VARIANT
<222> LOCATION: (27)
<223> OTHER INFORMATION: Xaa in position 27 stands for Lys-NH(epsilon)
      octanoyl
<220> FEATURE:
<221> NAME/KEY: AMIDATION
<222> LOCATION: (30)
<223> OTHER INFORMATION: Gly in position 30 is amidated

<400> SEQUENCE: 218

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Xaa Asn Gly Gly
            20                  25                  30

<210> SEQ ID NO 219
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (28)
<223> OTHER INFORMATION: Xaa in position 28 stands for Lys-NH(epsilon)
      octanoyl
<220> FEATURE:
<221> NAME/KEY: AMIDATION
<222> LOCATION: (28)
<223> OTHER INFORMATION: Lys-NH(epsilon) octanoyl in position 28 is
      amidated

<400> SEQUENCE: 219

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Asn Xaa
            20                  25

<210> SEQ ID NO 220
<211> LENGTH: 28
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (28)
<223> OTHER INFORMATION: Xaa in position 28 stands for Lys-NH(epsilon)
      octanoyl
<220> FEATURE:
<221> NAME/KEY: AMIDATION
<222> LOCATION: (28)
<223> OTHER INFORMATION: Lys-NH(epsilon) octanoyl in position 28 is
      amidated

<400> SEQUENCE: 220

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Asn Xaa
            20                  25

<210> SEQ ID NO 221
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: VARIANT
<222> LOCATION: (28)
<223> OTHER INFORMATION: Xaa in position 28 stands for Lys-NH(epsilon)
      octanoyl
<220> FEATURE:
<221> NAME/KEY: AMIDATION
<222> LOCATION: (30)
<223> OTHER INFORMATION: Gly in position 30 is amidated

<400> SEQUENCE: 221

Ala Gly Glu Gly Thr Phe Thr Ser Asp Leu Ser Lys Gln Met Glu Glu
 1               5                  10                  15

Glu Ala Val Arg Leu Phe Ile Glu Trp Leu Asn Xaa Gly Gly
             20                  25                  30

<210> SEQ ID NO 222
<211> LENGTH: 30
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: VARIANT
<222> LOCATION: (28)
<223> OTHER INFORMATION: Xaa in position 28 stands for Lys-NH(epsilon)
      octanoyl
<220> FEATURE:
<221> NAME/KEY: AMIDATION
<222> LOCATION: (30)
<223> OTHER INFORMATION: Gly in position 30 is amidated

<400> SEQUENCE: 222

Ala Gly Glu Gly Thr Phe Thr Ser Asp Leu Ser Lys Gln Leu Glu Glu
 1               5                  10                  15

Glu Ala Val Arg Leu Phe Ile Glu Phe Leu Asn Xaa Gly Gly
             20                  25                  30

<210> SEQ ID NO 223
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (12)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 223

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
             20                  25                  30

Ser Gly Ala Pro Pro Ser
                 35

<210> SEQ ID NO 224
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: MOD_RES
<222> LOCATION: (27)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 224

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 225
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (2)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 225

His Lys Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 226
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (5)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 226

His Gly Glu Gly Lys Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35
```

```
<210> SEQ ID NO 227
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (8)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 227

His Gly Glu Gly Thr Phe Thr Lys Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 228
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (10)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 228

His Gly Glu Gly Thr Phe Thr Ser Asp Lys Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 229
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (11)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 229

His Gly Glu Gly Thr Phe Thr Ser Asp Leu Lys Lys Gln Met Glu Glu
 1               5                  10                  15
```

```
Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 230
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (13)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 230

His Gly Glu Gly Thr Phe Thr Ser Asp Leu Ser Lys Lys Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 231
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (16)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 231

His Gly Glu Gly Thr Phe Thr Ser Asp Leu Ser Lys Gln Met Glu Lys
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 232
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (17)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated
```

```
<400> SEQUENCE: 232

His Gly Glu Gly Thr Phe Thr Ser Asp Leu Ser Lys Gln Met Glu Glu
1               5                   10                  15

Lys Ala Val Arg Leu Phe Ile Glu Trp Leu Lys Asn Gly Gly Pro Ser
            20                  25                  30

Ser Gly Ala Pro Pro Ser
        35

<210> SEQ ID NO 233
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (19)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 233

His Gly Glu Gly Thr Phe Thr Ser Asp Leu Ser Lys Gln Met Glu Glu
1               5                   10                  15

Glu Ala Lys Arg Leu Phe Ile Glu Trp Leu Lys Asn Gly Gly Pro Ser
            20                  25                  30

Ser Gly Ala Pro Pro Ser
        35

<210> SEQ ID NO 234
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (21)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 234

His Gly Glu Gly Thr Phe Thr Ser Asp Leu Ser Lys Gln Met Glu Glu
1               5                   10                  15

Glu Ala Val Arg Lys Phe Ile Glu Trp Leu Lys Asn Gly Gly Pro Ser
            20                  25                  30

Ser Gly Ala Pro Pro Ser
        35

<210> SEQ ID NO 235
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (24)
<223> OTHER INFORMATION: Lys-PEG
```

```
<220> FEATURE:
<221> NAME/KEY: AMIDATION
<222> LOCATION: (39)
<223> OTHER INFORMATION: Ser in position 39 is amidated

<400> SEQUENCE: 235

His Gly Glu Gly Thr Phe Thr Ser Asp Leu Ser Lys Gln Met Glu Glu
 1               5                  10                  15

Glu Ala Val Arg Leu Phe Ile Lys Trp Leu Lys Asn Gly Gly Pro Ser
            20                  25                  30

Ser Gly Ala Pro Pro Pro Ser
        35

<210> SEQ ID NO 236
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (25)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 236

His Gly Glu Gly Thr Phe Thr Ser Asp Leu Ser Lys Gln Met Glu Glu
 1               5                  10                  15

Glu Ala Val Arg Leu Phe Ile Glu Lys Leu Lys Asn Gly Gly Pro Ser
            20                  25                  30

Ser Gly Ala Pro Pro Pro Ser
        35

<210> SEQ ID NO 237
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (28)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 237

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Lys Gly Gly Pro Ser
            20                  25                  30

Ser Gly Ala Pro Pro Pro Ser
        35

<210> SEQ ID NO 238
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
```

```
<220> FEATURE:
<221> NAME/KEY: MOD_RES
<222> LOCATION: (29)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 238

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Lys Gly Pro Ser
            20                  25                  30

Ser Gly Ala Pro Pro Pro Ser
        35

<210> SEQ ID NO 239
<211> LENGTH: 39
<212> TYPE: PRT
<213> ORGANISM: Artificial Sequence
<220> FEATURE:
<223> OTHER INFORMATION: Description of Artificial Sequence: Synthetic
      Amino Acid Sequence
<220> FEATURE:
<221> NAME/KEY: MOD_RES
<222> LOCATION: (30)
<223> OTHER INFORMATION: Lys-PEG
<220> FEATURE:
<221> NAME/KEY: AMIDATION
<222> LOCATION: (39)
<223> OTHER INFORMATION: Ser in position 39 is amidated

<400> SEQUENCE: 239

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Lys Pro Ser
            20                  25                  30

Ser Gly Ala Pro Pro Pro Ser
        35
```

LYOPHILIZED FORMULATIONS OF EXENDINS AND EXENDIN AGONIST ANALOGS

RELATED APPLICATIONS

This application is a continuation of U.S. application Ser. No. 12/100,880 filed Apr. 10, 2008, which is a continuation of U.S. application Ser. No. 11/272,488 filed Nov. 10, 2005, issued as U.S. Pat. No. 7,399,489, which is a continuation-in-part of U.S. application Ser. No. 11/083,730 filed Mar. 18, 2005, issued as U.S. Pat. No. 7,153,825, which is a continuation of U.S. application Ser. No. 09/889,331 filed Dec. 18, 2001, issued as U.S. Pat. No. 6,872,700, which is a §371 of PCT/US00/00942 filed Jan. 14, 2000, claiming priority to U.S. Application No. 60/175,365 filed Jan. 10, 2000, U.S. Application No. 60/132,017 filed Apr. 30, 1999, and U.S. Application No. 60/116,380 filed Jan. 14, 1999, the contents of which are hereby incorporated by reference in their entireties.

FIELD OF THE INVENTION

The present application relates to novel formulations containing exendins, exendin agonists and exendin analogs.

INCORPORATION-BY-REFERENCE OF MATERIAL SUBMITTED BY EFS

The sequence listing in the present application is being submitted to the electronic filing system, the contents of which are hereby incorporated by reference.

BACKGROUND

The following description includes information that may be useful in understanding the present invention. It is not an admission that any of the information provided herein is prior art to the presently claimed invention, or relevant, nor that any of the publications specifically or implicitly referenced are prior art.

The exendins are peptides that are found in the salivary secretions of the Gila monster and the Mexican Beaded Lizard, reptiles that are endogenous to Arizona and Northern Mexico. Exendin-3 [SEQ ID NO: 1, i.e., His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$] is present in the salivary secretions of *Heloderma horridum* (Mexican Beaded Lizard), and exendin-4 [SEQ ID NO: 2, i.e., His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$] is present in the salivary secretions of *Heloderma suspectum* (Gila monster) (Eng, J., et al., *J. Biol. Chem.*, 265:20259-62, 1990; Eng, J., et al., *J. Biol. Chem.*, 267:7402-05, 1992). The amino acid sequence of exendin-3 is shown in FIG. 1. The amino acid sequence of exendin-4 is shown in FIG. 2. Exendin-4 was first thought to be a (potentially toxic) component of the venom. It now appears that exendin-4 is devoid of toxicity, and that it instead is made in salivary glands in the Gila monster.

The exendins have some sequence similarity to several members of the glucagon-like peptide family, with the highest homology, 53%, being to GLP-1 [7-36]NH$_2$ [SEQ ID NO: 3] (Goke, et al., *J. Biol. Chem.*, 268:19650-55, 1993). GLP-1 [7-36]NH$_2$, also sometimes referred to as proglucagon[78-107] or simply "GLP-1" as used most often herein, has an insulinotropic effect, stimulating insulin secretion from pancreatic beta-cells; GLP-1 has also been reported to inhibit glucagon secretion from pancreatic alpha-cells (Ørsov, et al., *Diabetes*, 42:658-61, 1993; D'Alessio, et al., *J. Clin. Invest.*, 97:133-38, 1996). GLP-1 has been reported to inhibit gastric emptying (Willms B, et al., *J Clin Endocrinol Metab* 81 (1): 327-32, 1996; Wettergren A, et al., *Dig Dis Sci* 38 (4): 665-73, 1993), and gastric acid secretion (Schjoldager B T, et al., *Dig Dis Sci* 34 (5): 703-8, 1989; O'Halloran D J, et al., *J Endocrinol* 126 (1): 169-73, 1990; Wettergren A, et al., *Dig Dis Sci* 38 (4): 665-73, 1993)). GLP-1 [7-37], which has an additional glycine residue at its carboxy terminus, is reported to stimulate insulin secretion in humans (Ørskov, et al., *Diabetes*, 42:658-61, 1993). A transmembrane G-protein adenylate-cyclase-coupled receptor said to be responsible at least in part for the insulinotropic effect of GLP-1 has reportedly been cloned from a beta-cell line (Thorens, *Proc. Natl. Acad. Sci. USA* 89:8641-45, 1992). GLP-1 has been the focus of significant investigation in recent years due to its reported action on the amplification of stimulated insulin production (Byrne M M, Goke B. Lessons from human studies with glucagon-like peptide-1: Potential of the gut hormone for clinical use. In: Fehmann H C, Goke B. Insulinotropic Gut Hormone Glucagon-Like Peptide 1. Basel, Switzerland: Karger, 1997:219-33).

Other reports relate to the inhibition of gastric emptying (Wettergren A, et al., Truncated GLP-1 (proglucagon 78-107-amide) inhibits gastric and pancreatic functions in man, *Dig. Dis. Sci.* 1993 April; 38(4):665-73), inhibition of glucagon secretion (Creutzfeldt W O C, et al., Glucagonostatic actions and reduction of fasting hyperglycemia by exogenous glucagon-like peptide I(7-36) amide in type 1 diabetic patients, *Diabetes Care* 1996; 19(6):580-6), and a purported role in appetite control (Turton M D, et al., A role for glucagon-like peptide-1 in the central regulation of feeding, *Nature* 1996 January; 379(6560):69-72).

GLP-1 has also been reported to restore islet glucose sensitivity in aging rats, restoring their glucose tolerance to that of younger rats (Egan J M, et al., Glucagon-like peptide-1 restores acute-phase insulin release to aged rats, Diabetologia 1997 June; 40 (Suppl 1):A130). However, the short duration of biological action of GLP-1 in vivo is one feature of the peptide that has hampered its development as a therapeutic agent. Various methods have been tried to prolong the half-life of GLP-1 or GLP-1 (7-37), including attempts to alter their amino acid sequence and to deliver them using certain formulations (see, e.g., European Patent Application, entitled "Prolonged Delivery of Peptides," by Darley, et al., publication number 0 619 322 A2, regarding the inclusion of polyethylene glycol in formulations containing GLP-1 (7-37)).

Pharmacological studies have led to reports that exendin-4 can act at GLP-1 receptors on certain insulin-secreting cells, at dispersed acinar cells from guinea pig pancreas, and at parietal cells from stomach; the peptide is also reported to stimulate somatostatin release and inhibit gastrin release in isolated stomachs (Goke, et al., *J. Biol. Chem.* 268:19650-55, 1993; Schepp, et al., *Eur. J. Pharmacol.*, 69:183-91, 1994; Eissele, et al., *Life Sci.*, 55:629-34, 1994). Exendin-3 and exendin-4 were reportedly found to stimulate cAMP production in, and amylase release from, pancreatic acinar cells (Malhotra, R., et al., *Regulatory Peptides*, 41:149-56, 1992; Raufman, et al., *J. Biol. Chem.* 267:21432-37, 1992; Singh, et al., *Regul. Pept.* 53:47-59, 1994). Additionally, exendin-4 has a significantly longer duration of action than GLP-1. For example, in one experiment, glucose lowering by exendin-4 in diabetic mice was reported to persist for several hours, and, depending on dose, for up to 24 hours (Eng J. Prolonged effect of exendin-4 on hyperglycemia of db/db mice, Diabetes 1996 May; 45 (Suppl 2):152A (abstract 554)). Based on their insulinotropic activities, the use of exendin-3 and exendin-4 for the treatment of diabetes mellitus and the prevention of hyperglycemia has been proposed (Eng, U.S. Pat. No. 5,424, 286).

The results of an investigation of whether exendins are the species homolog of mammalian GLP-1 was reported by Chen and Drucker who cloned the exendin gene from the Gila monster (J. Biol. Chem. 272(7):4108-15 (1997)). The observation that the Gila monster also has separate genes for proglucagons (from which GLP-1 is processed), that are more similar to mammalian proglucagon than exendin, indicates that exendins are not merely species homologs of GLP-1.

To date, agents that serve to delay gastric emptying have generally found a place in medicine as diagnostic aids in gastrointestinal radiological examinations. For example, glucagon is a polypeptide hormone that is produced by the alpha cells of the pancreatic islets of Langerhans. It is a hyperglycemic agent that mobilizes glucose by activating hepatic glycogenolysis. It can to a lesser extent stimulate the secretion of pancreatic insulin. Glucagon is used in the treatment of insulin-induced hypoglycemia, for example, when administration of glucose intravenously is not possible. However, as glucagon reduces the motility of the gastro-intestinal tract it is also used as a diagnostic aid in gastrointestinal radiological examinations. Glucagon has also been used in several studies to treat various painful gastrointestinal disorders associated with spasm. Daniel, et al. (Br. Med. J., 3:720, 1974) reported quicker symptomatic relief of acute diverticulitis in patients treated with glucagon compared with those who had been treated with analgesics or antispasmodics. A review by Glauser, et al. (J. Am. Coll. Emergency Physns, 8:228, 1979) described relief of acute esophageal food obstruction following glucagon therapy. In another study, glucagon significantly relieved pain and tenderness in 21 patients with biliary tract disease compared with 22 patients treated with placebo (M. J. Stower, et al., Br. J. Sure., 69:591-2, 1982).

Methods for regulating gastrointestinal motility using amylin agonists are described in commonly owned International Application No. PCT/US94/10225, published Mar. 16, 1995, as WO 1995/007098.

Methods for regulating gastrointestinal motility using exendin agonists are described in commonly owned U.S. Pat. No. 6,858,576 (i.e., U.S. patent application Ser. No. 08/908, 867, filed Aug. 8, 1997 entitled "Methods for Regulating Gastrointestinal Motility," which application is a continuation-in-part of U.S. patent application Ser. No. 08/694,954, filed Aug. 8, 1996). Methods for reducing food intake using exendin agonists are described in commonly owned U.S. Pat. No. 5,956,026 (i.e., U.S. patent application Ser. No. 09/003, 869, filed Jan. 7, 1998, entitled "Use of Exendin and Agonists Thereof for the Reduction of Food Intake," which claims the benefit of U.S. Provisional Application Nos. 60/034,905 filed Jan. 7, 1997, 60/055,404 filed Aug. 7, 1997, 60/065,442 filed Nov. 14, 1997 and 60/066,029 filed Nov. 14, 1997).

Novel exendin agonist compounds are described in commonly owned PCT Application Serial No. PCT/US98/16387 filed Aug. 6, 1998, entitled "Novel Exendin Agonist Compounds," published as WO 99/07404, which claims the benefit of U.S. Patent Application Ser. No. 60/055,404, filed Aug. 8, 1997. Other novel exendin agonists are described in commonly owned PCT Application Serial No. PCT/US98/24210, filed Nov. 13, 1998, entitled "Novel Exendin Agonist Compounds," published as WO 99/25727, which claims the benefit of U.S. Provisional Application No. 60/065,442 filed Nov. 14, 1997. Still other novel exendin agonists are described in commonly owned PCT Application Serial No. PCT/US98/ 24273, filed Nov. 13, 1998, entitled "Novel Exendin Agonist Compounds," published as WO 99/25728, which claims the benefit of U.S. Provisional Application No. 60/066,029 filed Nov. 14, 1997.

Other recent advances in exendin related technology are described in WO 99/40788 (i.e., U.S. Provisional Patent Application Ser. No. 60/075,122, filed Feb. 13, 1998, entitled "Inotropic and Diuretic Effects of Exendin and GLP-1") and in WO 00/41546 and WO 00/41548 (i.e., U.S. Provisional Patent Application Ser. No. 60/116,380, filed Jan. 14, 1998, entitled "Novel Exendin Agonist Formulations and Methods of Administration Thereof").

Polyethylene glycol (PEG) modification of therapeutic peptides and proteins may yield both advantages and disadvantages. While PEG modification may lead to improved circulation time, reduced antigenicity and immunogenicity, improved solubility, resistance to proteolysis, improved bioavailability, reduced toxicity, improved stability, and easier formulation of peptides (See, Francis et al., International Journal of Hematology, 68:1-18, 1998) problems with PEGylation in most cases is substantial reduction in bioactivity. Id. In addition, most methods involve use of linkers that have several types of adverse effects including immunogenicity, instability, toxicity, and reactivity. Id.

Glucagonoma (tumor of glucagon-secreting cells) produces, in addition to glucose intolerance, a skin condition, necrolytic migratory erythema. This is a raised scaly red rash, sometimes blistering and eventually crusting, localized to the face, abdomen, extremities and perineum. It can also be associated with inflammation of the tongue and mouth, and diseased nails and thinning of the hair. The condition is reported to respond to octreotide, a glucagonostatic hormone analog. The compounds described herein are also useful as glucagonastatic agents and thus in the treatment of this disease, which was first described in 1966 (Kaplan, L. M. Endocrine Tumors of the Gastrointestinal Tract and Pancreas. Ch 262, p 1392: In Harrison's Principles of Internal Medicine, 12th Edition. McGraw-Hill Inc, New York, 1991). The compounds described herein that are useful for lowering glucagon levels and/or suppressing glucagon secretion include exendin, exendin agonists, and modified exendins and exendin agonists and related formulations, and dosage formulations.

The contents of the above-identified articles, patents, and patent applications, and all other documents mentioned or cited herein, are hereby incorporated by reference in their entirety. Applicants reserve the right to physically incorporate into this application any and all materials and information from any such articles, patents, patent applications, or other documents mentioned or cited herein.

SUMMARY OF THE INVENTION

According to one aspect, the present invention provides novel exendin agonist compound formulations and dosages thereof exhibiting advantageous properties that include effects in slowing gastric emptying and lowering plasma glucose levels. Thus, this aspect of the invention includes formulations of exendins and exendin agonists that comprise an exendin or exendin agonist mixed together with a buffer (preferably an acetate buffer), an iso-osmolality modifier (preferably mannitol), and optionally containing a preservative (preferably m-cresol), said formulation having a pH of between about 3.0 and about 7.0 (preferably between about 4.0 and about 5.0).

Additional formulations within the scope of the invention include a parenteral liquid dosage form, a lyophilized unit-dosage form, a lyophilized multi-use dosage form, and modifications of these dosage forms that are useful in the oral, nasal, buccal, sublingual, intra-tracheal, and pulmonary delivery of exendins and exendin agonists.

Thus, the invention includes parenteral liquid dosage forms that comprise approximately 0.005 to about 0.4%, more specifically from about 0.005 to about 0.02%, or from about 0.005 to about 0.05% (w/v), respectively of the active ingredient in an aqueous system along with approximately 0.02 to 0.5% (w/v) of an acetate, phosphate, citrate or glutamate or similar buffer either alone or in combination to obtain a pH of the final composition of approximately 3.0 to 7.0, more specifically from about pH 4.0 to about 6.0, or from about 4.0 to 5.0, as well as either approximately 1.0 to 10% (w/v) of a carbohydrate or polyhydric alcohol iso-osmolality modifier (preferably mannitol) or up to about 0.9% saline or a combination of both leading to an isotonic or an iso-osmolar solution in an aqueous continuous phase. Approximately 0.005 to 1.0% (w/v) of an anti-microbial preservative selected from the group consisting of m-cresol, benzyl alcohol, methyl, ethyl, propyl and butyl parabens and phenol is also present if the formulation is packaged in a multi-use container. A sufficient amount of water for injection is added to obtain the desired concentration of solution. Sodium chloride, as well as other excipients, may also be present, if desired. Such excipients, however, must maintain the overall stability of the active ingredient. Useful polyhydric alcohols include such compounds as sorbitol, mannitol, glycerol, and polyethylene glycols (PEGs). The polyhydric alcohols and the carbohydrates will also be effective in stabilizing protein against denaturation caused by elevated temperature and by freeze-thaw or freeze-drying processes. Suitable carbohydrates include galactose, arabinose, lactose or any other carbohydrate which does not have an adverse affect on a diabetic patient, if intended for that use, i.e., the carbohydrate is not metabolized to form large concentrations of glucose in the blood. Preferably, the peptides of the present invention are admixed with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Mannitol is the preferred polyhydric alcohol.

The lyophilized unit-dose formulations of the present invention are also stable, but need not be isotonic and/or iso-osmolar. They include active ingredient(s), a bulking agent to facilitate cake formation (which may also act as a tonicifer and/or iso-osmolality modifier upon reconstitution to either facilitate stability of the active ingredient and/or lessen the pain on injection), and may also include a surfactant that benefits the properties of the cake and/or facilitates reconstitution. The lyophilized unit-dose formulations of the present invention include approximately 0.005 to about 0.4%, more specifically from about 0.005 to about 0.02%, or 0.005 to 0.05% (w/v) of the active ingredient. It may not be necessary to include a buffer in the formulation and/or to reconstitute the lyophile with a buffer if the intention is to consume the contents of the container within the stability period established for the reconstituted active ingredient. If a buffer is used, it may be included in the lyophile or in the reconstitution solvent. Therefore, the formulation and/or the reconstitution solvent may contain individually or collectively approximately 0.02 to 0.5% (w/v) of an acetate, phosphate, citrate or glutamate buffer either alone or in combination to obtain a pH of the final composition of approximately 3.0 to 7.0, more specifically from about pH 4.0 to about 6.0, or from about 4.0 to 5.0. The bulking agent may consist of either approximately 1.0 to 10% (w/v) of a carbohydrate or polyhydric alcohol iso-osmolality modifier (as described above) or up to 0.9% saline or a combination of both leading to a isotonic or iso-osmolar solution in the reconstituted aqueous phase. A surfactant, preferably about 0.1 to about 1.0% (w/v) of polysorbate 80 or other non-ionic detergent, may be included. As noted above, sodium chloride, as well as other excipients, may also be present in the lyophilized unit-dosage formulation, if desired. The liquid formulation of the invention prior to lyophilization will be substantially isotonic and/or iso-osmolar either before lyophilization or to enable formation of isotonic and/or iso-osmolar solutions after reconstitution.

The invention also includes lyophilized and liquid multi-dose formulations. As with the parenteral liquid and lyophilized unit-dosage formulations described above, the lyophilized multi-unit-dosage form should contain a bulking agent to facilitate cake formation. A preservative is included to facilitate multiple use by the patient. These dosage forms include approximately 0.005 to about 0.4%, more specifically from about 0.005 to about 0.02%, or from about 0.005 to 0.05% (w/v), respectively of the active ingredient. If a buffer is used, it may be included in the lyophile or in the reconstitution solvent, and the formulation and/or the reconstitution solvent may contain individually or collectively approximately 0.02 to 0.5% (w/v) of an acetate, phosphate, citrate or glutamate buffer either alone or in combination to obtain a pH of the final composition of approximately 3.0 to 7.0, more specifically from about pH 4.0 to about 6.0, or from about 4.0 to 5.0. The bulking agent may consist of either approximately 1.0 to 10% (w/v) of a carbohydrate or a polyhydric alcohol iso-osmolality modifier (preferably mannitol) or up to 0.9% saline, or a combination of both, leading to an isotonic or iso-osmolar solution in the reconstituted aqueous phase. A surfactant, preferably about 0.1 to about 1.0% (w/v) of polysorbate 80 or other non-ionic detergent, may be included. Approximately 0.005 to 1.0% (w/v) of an anti-microbial preservative selected from the group consisting of m-cresol, benzyl alcohol, methyl, ethyl, propyl and butyl parabens and phenol (preferably m-cresol) is also present if the formulation is packaged in a multi-use container. Sodium chloride, as well as other excipients, may also be present, if desired. The liquid formulation of the invention should be substantially isotonic and/or iso-osmolar either before lyophilization or to enable formation of isotonic and/or iso-osmolar solutions after reconstitution.

The invention further includes solid dosage forms useful for oral, buccal, sublingual, intra-tracheal, nasal, and pulmonary delivery. The formulations that best support pulmonary and/or intra-tracheal dosage forms may be either preserved or unpreserved liquid formulations and/or dry powder formulations. The preserved or unpreserved liquid formulations will be essentially identical to the formulations described above under preserved or unpreserved liquid parenteral formulations. The pH of the solution should be about 3.0 to 7.0, more specifically from about 4.0 to 6.0, or from about 4.0 to 5.0, with a pH greater than or equal to about 5.0 being most preferred to reduce the potential for bronchoconstriction. The dry powder formulations may contain a bulking agent and/or salts to facilitate particle size formation and appropriate particle size distribution. A surfactant and/or salts may also benefit the properties of the particle morphology and/or facilitate tissue uptake of the active ingredient. Dry powder dosage forms can range from 1% to 100% (w/w), respectively of the active ingredient. It may not be necessary to include a bulking agent and/or salts to facilitate particle size formation and/or distribution. The bulking agent and/or salts may consist of either approximately 0 to 99% (w/w) of a carbohydrate or polyhydric alcohol or approximately 0 to 99% salt or a combination of both leading to the preferred particle size and distribution. A surfactant, preferably about 0.1 to about 1.0% (w/w) of polysorbate 80 or other non-ionic detergent, may be included. Sodium chloride, as well as other excipients, may also be present, if desired. Such excipients, however, will maintain the overall stability of the active ingredient and facilitate the proper level of hydration.

Also within the scope of the invention is the formulation comprising up to 50 mg/ml of an exendin or an exendin agonist in 30 mM acetate buffer (pH about 4.5) and mannitol, with or without a preservative.

Further within the scope of the invention are preferred dosages for exendins and exendin agonists when given by injection, and when given by other routes. Thus, formulations for exendin and exendin agonists having comparable potency are provided for the administration by injection of from about 0.1 to about 0.5 μg per kilogram, given one to three times per day. Typically, for the patient with diabetes who weighs in the range from about 70 kilograms (average for the type 1 diabetic) to about 90 kilograms (average for the type 2 diabetic), for example, this will result in the total administration of about 10 to about 120 μg per day in single or divided doses. If administered in divided doses, the doses are preferably administered two or three times per day, and more preferably, two times per day.

Oral dosages according to the present invention will include from about 50 to about 100 times the active ingredient, i.e., from about 500 to about 12,000 μg per day in single or divided doses, preferably from about 500 to about 5,000 μg per day. Pulmonary dosages according to the present invention will include from about 10 to about 100 times the active ingredient, i.e., from about 100 to about 12,000 μg per day in single or divided doses, preferably about 500 to 1000 μg per day. Nasal, buccal and sublingual dosages according to the present invention will also include from about 10 to about 100 times the active ingredient, i.e., from about 100 to about 12,000 μg per day in single or divided doses.

Preferred dosages for nasal administration are from about 10-1000 to about 1200-12,000 μg per day, for buccal administration from about 10-1000 to about 1200-12,000 μg per day, and for sublingual administration from about 10-1000 to about 1200-8,000 μg per day. Sublingual dosages are preferably smaller than buccal dosages. Administration dosages for exendin agonists having less than or greater than the potency of exendin-4 are increased or decreased as appropriate from those described above and elsewhere herein.

Also included within the scope of the present invention are methods of administration of said novel exendin agonist compound formulations and dosages by delivery means alternative to subcutaneous injection or intravenous infusion, including, for example, by nasal delivery, pulmonary delivery, oral delivery, intra-tracheal delivery, sublingual delivery, and buccal delivery.

According to another aspect, the present invention provides novel exendin agonist compound formulations and dosages, and methods for the administration thereof, that are useful in treating diabetes (including type 1 and type 2 diabetes), obesity, and other conditions that will benefit from the administration of a therapy that can slow gastric emptying, lowering plasma glucose levels, and reduce food intake.

Preferred exendins or exendin agonists for use include: exendin-4 (1-30) [SEQ ID NO: 4, i.e., His Gly Glu Gly Thr Phe Thr Ser Asp Leu Ser Lys Gln Met Glu Glu Glu Ala Val Arg Leu Phe Ile Glu Trp Leu Lys Asn Gly Gly]; exendin-4 (1-30) amide [SEQ ID NO: 5, i.e., His Gly Glu Gly Thr Phe Thr Ser Asp Leu Ser Lys Gln Met Glu Glu Glu Ala Val Arg Leu Phe Ile Glu Trp Leu Lys Asn Gly Gly-NH$_2$]; exendin-4 (1-28) amide [SEQ ID NO: 6, i.e., His Gly Glu Gly Thr Phe Thr Ser Asp Leu Ser Lys Gln Met Glu Glu Glu Ala Val Arg Leu Phe Ile Glu Trp Leu Lys Asn-NH$_2$]; $^{14}$Leu, $^{25}$Phe exendin-4 amide [SEQ ID NO: 7, i.e., His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-NH$_2$]; $^{14}$Leu, $^{25}$Phe exendin-4 (1-28) amide [SEQ ID NO: 8, i.e., His Gly Glu Gly Thr Phe Thr Ser Asp Leu Ser Lys Gln Leu Glu Glu Glu Ala Val Arg Leu Phe Ile Glu Phe Leu Lys Asn-NH$_2$]; and $^{14}$Leu, $^{22}$Ala, $^{25}$Phe exendin-4 (1-28) amide [SEQ ID NO: 9, i.e., His Gly Glu Gly Thr Phe Thr Ser Asp Leu Ser Lys Gln Leu Glu Glu Glu Ala Val Arg Leu Ala Ile Glu Phe Leu Lys Asn-NH$_2$].

DEFINITIONS

In accordance with the present invention and as used herein, the following terms are defined to have the following meanings, unless explicitly stated otherwise.

The term "amino acid" refers to natural amino acids, unnatural amino acids, and amino acid analogs, all in their D and L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Amino acid analogs include the natural and unnatural amino acids which are chemically blocked, reversibly or irreversibly, or modified on their N-terminal amino group or their side-chain groups, as for example, methionine sulfoxide, methionine sulfone, S-(carboxymethyl)-cysteine, S-(carboxymethyl)-cysteine sulfoxide and S-(carboxymethyl)-cysteine sulfone.

The term "amino acid analog" refers to an amino acid wherein either the C-terminal carboxy group, the N-terminal amino group or side-chain functional group has been chemically codified to another functional group. For example, aspartic acid-(beta-methyl ester) is an amino acid analog of aspartic acid; N-ethylglycine is an amino acid analog of glycine; or alanine carboxamide is an amino acid analog of alanine.

The term "amino acid residue" refers to radicals having the structure: (1) —C(O)—R—NH—, wherein R typically is —CH(R')—, wherein R' is an amino acid side chain, typically H or a carbon containing substitutent; or

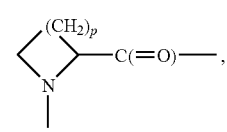

(2)

wherein p is 1, 2 or 3 representing the azetidinecarboxylic acid, proline or pipecolic acid residues, respectively.

The term "lower" referred to herein in connection with organic radicals such as alkyl groups defines such groups with up to and including about 6, preferably up to and including 4 and advantageously one or two carbon atoms. Such groups may be straight chain or branched chain.

"Pharmaceutically acceptable salt" includes salts of the compounds of the present invention derived from the combination of such compounds and an organic or inorganic acid. In practice the use of the salt form amounts to use of the base form. The compounds of the present invention are useful in both free base and salt form, with both forms being considered as being within the scope of the present invention.

In addition, the following abbreviations stand for the following: "ACN" or "CH$_3$CN" refers to acetonitrile. "Boc", "tBoc" or "Tboc" refers to t-butoxy carbonyl. "DCC" refers to N,N'-dicyclohexylcarbodiimide. "Fmoc" refers to fluorenylmethoxycarbonyl. "HBTU" refers to 2-(1H-benzotriazol-1-yl)-1,1,3,3,-tetramethyluronium hexafluorophosphate. "HOBt" refers to 1-hydroxybenzotriazole monohydrate. "homoP" or hPro" refers to homoproline. "MeAla" or "Nme" refers to N-methylalanine. "naph" refers to naphthylalanine. "pG" or pGly" refers to pentylglycine. "tBuG" refers to tertiary-butylglycine. "ThioP" or tPro" refers to thioproline. "3Hyp" refers to 3-hydroxyproline. "4Hyp" refers to 4-hydroxyproline. "NAG" refers to N-alkylglycine. "NAPG" refers to N-alkylpentylglycine. "Norval" refers to norvaline. "Norleu" refers to norleucine.

Other features and advantages of the invention will be apparent from the following description of the preferred embodiments thereof, and from the claims.

BRIEF DESCRIPTION OF THE DRAWINGS

FIG. 1 depicts the amino acid sequence for exendin-3 [SEQ ID NO: 1].

FIG. 2 depicts the amino acid sequence for exendin-4 [SEQ ID NO: 2].

FIGS. 3A-B depict the amino acid sequences for certain exendin agonist compounds useful in the present invention [SEQ ID NOs: 10 to 40].

FIG. 4A shows Compound Nos. 1-20 (SEQ ID NOs:49-68) having the amino acid sequence: His Xaa$_2$ Glu Gly Xaa$_5$ Xaa$_6$ Thr Xaa$_8$ Asp Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Val Arg Xaa$_{21}$ Phe Ile Xaa$_{24}$ Xaa$_{25}$ Leu Lys Asn Xaa$_{29}$ Xaa$_{30}$-NH$_2$, wherein the Xaa variables are defined in the figure.

FIG. 4B shows Compound Nos. 21-41 (SEQ ID NOs:69-89) having the amino acid sequence: His Gly Glu Gly Thr Phe Thr Ser Asp Leu Ser Lys Gln Xaa$_{14}$ Glu Glu Glu Ala Val Arg Leu Phe Ile Glu Xaa$_{25}$ Xaa$_{26}$ Xaa$_{27}$ Xaa$_{28}$ Xaa$_{29}$ Xaa$_{30}$ Xaa$_{31}$ Xaa$_{32}$ Xaa$_{33}$ Xaa$_{34}$ Xaa$_{35}$ Xaa$_{36}$ Xaa$_{37}$ Xaa$_{38}$-NH$_2$, wherein the Xaa variables are defined in the figure.

FIG. 4C shows Compound Nos. 42-61 (SEQ ID NOs:90-109) having the amino acid sequence: Xaa$_1$ Gly Xaa$_3$ Gly Thr Xaa$_6$ Xaa$_7$ Xaa$_8$ Xaa$_9$ Xaa$_{10}$ Ser Lys Gln Xaa$_{14}$ Xaa$_{15}$ Glu Glu Ala Val Arg Leu Xaa$_{22}$ Xaa$_{23}$ Xaa$_{24}$ Xaa$_{25}$ Leu Lys Asn Xaa$_{29}$ Xaa$_{30}$ Xaa$_{31}$ Xaa$_{32}$ Xaa$_{33}$ Xaa$_{34}$ Xaa$_{35}$ Xaa$_{36}$ Xaa$_{37}$ Xaa$_{38}$-NH$_2$, wherein the Xaa variables are defined in the figure.

FIG. 4D shows Compound Nos. 70-91 (SEQ ID NOs:118-139) having the amino acid sequence: Xaa$_1$Xaa$_2$Xaa$_3$Xaa$_4$Xaa$_5$Xaa$_6$Xaa$_7$Xaa$_8$Xaa$_9$Xaa$_{10}$Xaa$_{11}$Xaa$_{12}$Xaa$_{13}$Xaa$_{14}$ Glu Glu Glu Ala Val Arg Leu Phe Ile Glu Xaa$_{25}$ Leu Lys Asn-NH$_2$, wherein the Xaa variables are defined in the figure.

FIG. 4E shows Compound Nos. 92-104 (SEQ ID NOs: 140-153) having the amino acid sequence: Ala Gly Asp Gly Thr Phe Thr Ser Xaa$_9$ Xaa$_{10}$ Xaa$_{11}$ Xaa$_{12}$ Xaa$_{13}$ Xaa$_{14}$ Glu Glu Ala Val Arg Leu Phe Ile Glu Xaa$_{25}$ Leu Lys Asn-NH$_2$, wherein the Xaa variables are defined in the figure.

FIG. 4F shows Compound Nos. 105-124 (SEQ ID NOs: 154-173) having the amino acid sequence: Ala Gly Asp Gly Thr Phe Thr Ser Asp Leu Ser Lys Gln Xaa$_{14}$ Xaa$_{15}$ Xaa$_{16}$ Xaa$_{17}$ Ala Xaa$_{19}$ Xaa$_{20}$ Xaa$_{21}$ Xaa$_{22}$ Xaa$_{23}$ Glu Xaa$_{25}$ Leu Lys Asn-NH$_2$, wherein the Xaa variables are defined in the figure.

FIG. 4G shows Compound Nos. 125-136 (SEQ ID NOs: 174-185) having the amino acid sequence: Ala Gly Asp Gly Thr Phe Thr Ser Asp Leu Ser Lys Gln Xaa$_{14}$ Glu Glu Glu Ala Val Arg Leu Phe Xaa$_{23}$ Xaa$_{24}$ Xaa$_{25}$ Xaa$_{26}$ Xaa$_{27}$ Xaa$_{28}$-NH$_2$, wherein the Xaa variables are defined in the figure.

FIG. 4H shows Compound Nos. 137-158 (SEQ ID NOs: 186-207) having the amino acid sequence: Xaa$_1$ Gly Xaa$_3$ Xaa$_4$ Thr Phe Thr Ser Xaa$_9$ Xaa$_{10}$ Ser Lys Gln Xaa$_{14}$ Glu Glu Glu Ala Val Arg Leu Phe Ile Glu Xaa$_{25}$ Leu Lys Asn Gly Xaa$_{30}$ Xaa$_{31}$ Xaa$_{32}$ Xaa$_{33}$ Xaa$_{34}$ Xaa$_{35}$ Xaa$_{36}$ Xaa$_{37}$ Xaa$_{38}$ Xaa$_{39}$-NH$_2$, wherein the Xaa variables are defined in the figure.

FIG. 4I shows the amino acid sequences of Compound Nos. 159-174.

FIG. 8A depicts the plasma exendin-4 concentration after intra-tracheal instillation in db/db mice, 4.5 hours after treatment. FIG. 8B depicts the effect of intra-tracheal administration of exendin-4 on plasma glucose in db/db mice, 1.5 hours after treatment. Male db/db mice (approximately 50 g) were fasted for 2 hours, and the trachea was intubated under anesthesia. The animals were bled (75 μL, orbital sinus) before and after 20 μL of saline or 1 μg of exendin-4 dissolved in 20 μL of saline was administered into the trachea of each animal.

DETAILED DESCRIPTION OF THE INVENTION

Figure 5:
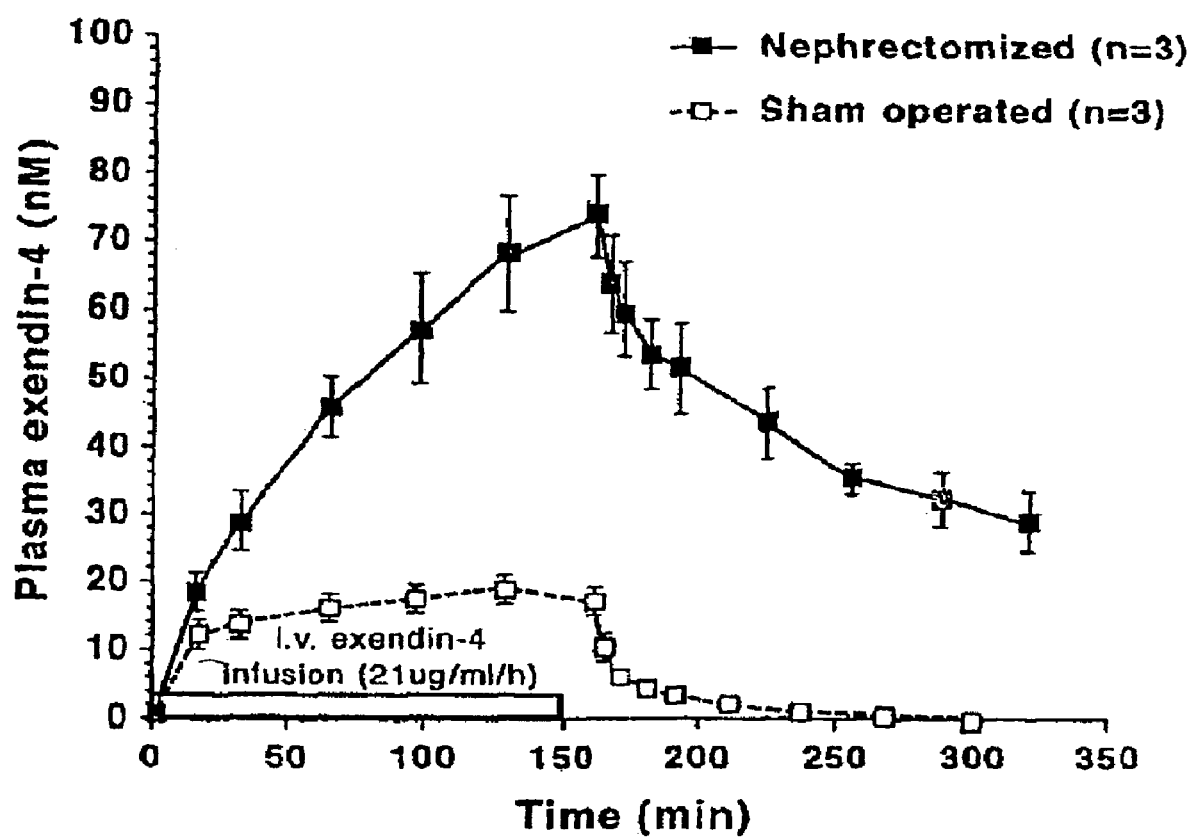
FIG. 5 is a graph showing the effect of functional nephrectomy on exendin-4 clearance.

The present invention relates to relates to methods of suppressing and/or lowering glucagon in a subject, comprising the administration of an exendin, an exendin agonist, or a modified exendin or exendin agonist having an exendin or exendin agonist peptide linked to one or more polyethylene glycol polymers or other compound useful to increase molecular weight. Such methods are useful, for example, in the treatment of hyperglucagonemia and other conditions in which lower levels of glucagon or suppression of glucagon secretion are of benefit. Such conditions include, but are not limited to, glucagonoma and necrolytic migratory erythema.
Modified Exendins and Exendin Agonists The modified exendins and exendin agonists of the present invention include, for example, one or more PEG polymers linked to an exendin or exendin agonist, such as a naturally occurring exendin, a synthetic exendin or an exendin agonist.
Exendin-4

Exendin-4 is a naturally occurring peptide isolated from the salivary secretions of the Gila monster. Animal testing of exendin-4 has shown that its ability to lower blood glucose persists for several hours. Exendin-4, a 39-amino acid polypeptide, is synthesized using solid phase synthesis as described herein, and this synthetic material has been shown to be identical to that of native exendin-4.

As described herein, the nonclinical pharmacology of exendin-4 has been studied. In the brain, exendin-4 binds principally to the area postrema and nucleus tractus solitarius region in the hindbrain and to the subformical organ in the forebrain. Exendin-4 binding has been observed in the rat and mouse brain and kidney. The structures to which exendin-4 binds in the kidney are unknown.

Various experiments have compared the biologic actions of exendin-4 and GLP-1 and demonstrated a more favorable spectrum of properties for exendin-4. A single subcutaneous dose of exendin-4 lowered plasma glucose in db/db (diabetic) and ob/ob (diabetic obese) mice by up to 40%. In Diabetic Fatty Zucker (ZDF) rats, 5 weeks of treatment with exendin-4 lowered $HbA_{1c}$ (a measure of glycosylated hemoglobin used to evaluate plasma glucose levels) by up to 41%. Insulin sensitivity was also improved by 76% following 5 weeks of treatment in obese ZDF rats. In glucose intolerant primates, dose-dependent decreases in plasma glucose were also observed.

An insulinotropic action of exendin-4 has also been observed in rodents, improving insulin response to glucose by over 100% in non-fasted Harlan Sprague Dawley (HSD) rats, and by up to ~10-fold in non-fasted db/db mice. Higher pre-treatment plasma glucose concentrations were associated with greater glucose-lowering effects. Thus the observed glucose lowering effect of exendin-4 appears to be glucose-dependent, and minimal if animals are already euglycemic.

Exendin-4 dose dependently slowed gastric emptying in HSD rats and was 90-fold more potent than GLP-1 for this action. Exendin-4 has also been shown to reduce food intake in NIH/Sw (Swiss) mice following peripheral administration, and was at least 1000 times more potent than GLP-1 for this action. Exendin-4 reduced plasma glucagon concentrations by approximately 40% in anesthetized ZDF rats during hyperinsulinemic, hyperglycemic clamp conditions, but did not affect plasma glucagon concentrations during euglycemic conditions in normal rats. Exendin-4 has been shown to dose-dependently reduce body weight in obese ZDF rats, while in lean ZDF rats, the observed decrease in body weight appears to be transient.

Through effects on lowering glucagon and suppressing glucagon secretion, exendins, exendin agonists, and modified exendins or exendin agonists containing exendin-4, for example, will be useful in people who would benefit from lowered glucagon, for example, people with glucagonoma and necrolytic migratory erythema, and people with diabetes whether or not they retain the ability to secrete insulin. See Example 5.

The toxicology of exendin-4 has been investigated in single-dose studies in mice, rats and monkeys, repeated-dose (up to 28 consecutive daily doses) studies in rats and monkeys and in vitro tests for mutagenicity and chromosomal alterations. To date, no deaths have occurred, and there have been no observed treatment-related changes in hematology, clinical chemistry, or gross or microscopic tissue changes. Exendin-4 was demonstrated to be non-mutagenic, and did not cause chromosomal aberrations at the concentrations tested (up to 5000 µg/mL).

In support of the investigation of the nonclinical pharmacokinetics and metabolism of exendin-4, a number of immunoassays have been developed. A radioimmunoassay with limited sensitivity (~100 µM) was used in initial pharmacokinetic studies. A two-site IRMA assay for exendin-4 was subsequently validated with a lower limit of quantitation of 15 µM. The bioavailability of exendin-4, given subcutaneously, was found to be approximately 50-80% using the radioimmunoassay. This was similar to that seen following intraperitoneal administration (48-60%). Peak plasma concentrations ($C_{max}$) occurred between 30 and 43 minutes ($T_{max}$). Both $C_{max}$ and AUC values were monotonically related to dose. The apparent terminal half-life for exendin-4 given subcutaneously was approximately 90-110 minutes. This was significantly longer than the 14-41 minutes seen following intravenous dosing. Similar results were obtained using the IRMA assay. Degradation studies with exendin-4 compared to GLP-1 indicate that exendin-4 is relatively resistant to degradation.

Exendin Agonists

The structure activity relationship (SAR) of exendin was investigated for structures that may relate to the antidiabetic activity of exendin, for its stability to metabolism, and for improvement of its physical characteristics, especially as it pertains to peptide stability and to amenability to alternative delivery systems, and various exendin agonist peptide compounds have been invented. Exendin agonists include exendin peptide analogs in which one or more naturally occurring amino acids are eliminated or replaced with another amino acid(s). Preferred exendin agonists are agonist analogs of exendin-4. Particularly preferred exendin agonists include those described in commonly owned WO 99/07404 (i.e., PCT Application Serial No. PCT/US98/16387 filed Aug. 6, 1998, entitled "Novel Exendin Agonist Compounds," which claims the benefit of U.S. Patent Application Ser. No. 60/055,404, filed Aug. 8, 1997); commonly owned WO 99/25727 (i.e., PCT Application Serial No. PCT/US98/24210, filed Nov. 13, 1998, entitled "Novel Exendin Agonist Compounds," which claims the benefit of U.S. Provisional Application No. 60/065,442 filed Nov. 14, 1997); and commonly owned WO 99/25728 (i.e., PCT Application Serial No. PCT/US98/24273, filed Nov. 13, 1998, entitled "Novel Exendin Agonist Compounds," which claims the benefit of U.S. Provisional Application No. 60/066,029 filed Nov. 14, 1997), all of which are incorporated herein by reference in their entirety, including any drawings.

Activity as exendin agonists can be indicated, for example, by activity in the assays described below. Effects of exendins or exendin agonists on gastric motility and gastric emptying can be identified, evaluated, or screened for, using the methods described herein, or other art-known or equivalent methods for determining gastric motility. Negative receptor assays or screens for exendin agonist compounds or candidate exendin agonist compounds, such as an amylin receptor assay/screen using an amylin receptor preparation as described in U.S. Pat. No. 5,264,372, issued Nov. 23, 1993, the contents of which are incorporated herein by reference, one or more calcitonin receptor assays/screens using, for example, T47D and MCF7 breast carcinoma cells, which contain calcium receptors coupled to the stimulation of adenyl cyclase activity, and/or a CGRP receptor assay/screen using, for example, SK-N-MC cells.

One such method for use in identifying or evaluating the ability of a compound to slow gastric motility, involves: (a) bringing together a test sample and a test system, the test sample containing one or more test compounds, the test system containing a system for evaluating gastric motility, the system being characterized in that it exhibits, for example, elevated plasma glucose in response to the introduction to the system of glucose or a meal; and, (b) determining the presence or amount of a rise in plasma glucose in the system. Positive and/or negative controls may be used as well.

Also included within the scope of the present invention are pharmaceutically acceptable salts of the compounds of formula (I-VIII) and pharmaceutical compositions including said compounds and salts thereof.

Formula I

Exendin agonist compounds also include those described in U.S. Provisional Application No. 60/065,442 (i.e., priority application to WO 99/25727) including compounds of the formula (I) [SEQ ID NO: 41]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein: $Xaa_1$ is His, Arg or Tyr; $Xaa_2$ is Ser, Gly, Ala or Thr; $Xaa_3$ is Ala, Asp or Glu; $Xaa_5$ is Ala or Thr; $Xaa_6$ is Ala, Phe, Tyr or naphthylalanine; $Xaa_7$ is Thr or Ser; $Xaa_8$ is Ala, Ser or Thr; $Xaa_9$ is Asp or Glu; $Xaa_{10}$ is Ala, Leu, Ile, Val, pentylglycine or Met; $Xaa_{11}$ is Ala or Ser; $Xaa_{12}$ is Ala or Lys; $Xaa_{13}$ is Ala or Gln; $Xaa_{14}$ is Ala, Leu, Ile, pentylglycine, Val or Met; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Ala, Phe, Tyr or naphthylalanine; $Xaa_{23}$ is Ile, Val, Leu, pentylglycine, tert-butylglycine or Met; $Xaa_{24}$ is Ala, Glu or Asp; $Xaa_{25}$ is Ala, Trp, Phe, Tyr or naphthylalanine; $Xaa_{26}$ is Ala or Leu; $Xaa_{27}$ is Ala or Lys; $Xaa_{28}$ is Ala or Asn; $Z_1$ is OH, $NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$ or Gly Gly $Xaa_{31}$ Ser Ser Gly Ala $Xaa_{36}$ $Xaa_{37}$ $Xaa_{38}$-$Z_2$; $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and $Z_2$ is OH or $NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms.

Preferred exendin agonist compounds include those wherein $Xaa_1$ is His or Tyr. More preferably $Xaa_1$ is His. Preferred are those compounds wherein $Xaa_2$ is Gly. Preferred are those compounds wherein $Xaa_{14}$ is Leu, pentylglycine or Met. Preferred compounds are those wherein $Xaa_{25}$ is Trp or Phe. Preferred compounds are those where $Xaa_6$ is Phe or naphthylalanine; $Xaa_{22}$ is Phe or naphthylalanine and $Xaa_{23}$ is Ile or Val. Preferred are compounds wherein $Xaa_{31}$, $Xaa_{36}$, $Xaa_{37}$ and $Xaa_{38}$ are independently selected from Pro, homoproline, thioproline and N-alkylalanine. Preferably $Z_1$ is $NH_2$. Preferably $Z_2$ is $NH_2$.

According to one aspect, preferred are compounds of formula (I) wherein $Xaa_1$ is His or Tyr, more preferably His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. More preferably $Z_1$ is —$NH_2$.

According to an especially preferred aspect, especially preferred compounds include those of formula (I) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or nephthylalaine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly Xaa₃₁-Z₂, Gly Gly Xaa₃₁ Ser-Z₂, Gly Gly Xaa₃₁ Ser Ser-Z₂, Gly Gly Xaa₃₁ Ser Ser Gly-Z₂, Gly Gly Xaa₃₁ Ser Ser Gly Ala-Z₂, Gly Gly Xaa₃₁ Ser Ser Gly Ala Xaa₃₆-Z₂, Gly Gly Xaa₃₁ Ser Ser Gly Ala Xaa₃₆ Xaa₃₇-Z₂, Gly Gly Xaa₃₁ Ser Ser Gly Ala Xaa₃₆ Xaa₃₇ Xaa₃₈-Z₂; Xaa₃₁, Xaa₃₆, Xaa₃₇ and Xaa₃₈ being independently Pro homoproline, thioproline or N-methylalanine; and Z₂ being —OH or —NH₂; provided that no more than three of Xaa₃, Xaa₅, Xaa₆, Xaa₈, Xaa₁₀, Xaa₁₁, Xaa₁₂, Xaa₁₃, Xaa₁₄, Xaa₁₅, Xaa₁₆, Xaa₁₇, Xaa₁₉, Xaa₂₀, Xaa₂₁, Xaa₂₄, Xaa₂₅, Xaa₂₆, Xaa₂₇ and Xaa₂₈ are Ala. Especially preferred compounds include those set forth in PCT application Serial No. PCT/US98/24210, filed Nov. 13, 1998, entitled "Novel Exendin Agonist Compounds" identified therein as compounds 2-23.

According to an especially preferred aspect, provided are compounds where Xaa₁₄ is Leu, Ile, Val or pentylglycine, more preferably Leu or pentylglycine, and Xaa₂₅ is Phe, Tyr or naphthylalanine, more preferably Phe or naphthylalanine. These compounds will be less susceptive to oxidative degradation, both in vitro and in vivo, as well as during synthesis of the compound.

Formula II

Exendin agonist compounds also include those described in U.S. Provisional Application No. 60/066,029 (i.e., priority application to WO 99/25728) including compounds of the formula (II) [SEQ ID NO: 42]:

Xaa₁ Xaa₂ Xaa₃ Xaa₄ Xaa₅ Xaa₆ Xaa₇ Xaa₈ Xaa₉ Xaa₁₀

Xaa₁₁ Xaa₁₂ Xaa₁₃ Xaa₁₄ Xaa₁₅ Xaa₁₆ Xaa₁₇ Ala

Xaa₁₉ Xaa₂₀ Xaa₂₁ Xaa₂₂ Xaa₂₃ Xaa₂₄ Xaa₂₅ Xaa₂₆

Xaa₂₇ Xaa₂₈-Z₁;

wherein Xaa₁ is His, Arg, Tyr, Ala, Norval, Val or Norleu; Xaa₂ is Ser, Gly, Ala or Thr; Xaa₃ is Ala, Asp or Glu; Xaa₄ is Ala, Norval, Val, Norleu or Gly; Xaa₅ is Ala or Thr; Xaa₆ is Ala, Phe, Tyr or naphthylalanine; Xaa₇ is Thr or Ser; Xaa₈ is Ala, Ser or Thr; Xaa₉ is Ala, Norval, Val, Norleu, Asp or Glu; Xaa₁₀ is Ala, Leu, Ile, Val, pentylglycine or Met; Xaa₁₁ is Ala or Ser; Xaa₁₂ is Ala or Lys; Xaa₁₃ is Ala or Gln; Xaa₁₄ is Ala, Leu, Ile, pentylglycine, Val or Met; Xaa₁₅ is Ala or Glu; Xaa₁₆ is Ala or Glu; Xaa₁₇ is Ala or Glu; Xaa₁₉ is Ala or Val; Xaa₂₀ is Ala or Arg; Xaa₂₁ is Ala or Leu; Xaa₂₂ is Phe, Tyr or naphthylalanine; Xaa₂₃ is Ile, Val, Leu, pentylglycine, tert-butylglycine or Met; Xaa₂₄ is Ala, Glu or Asp; Xaa₂₅ is Ala, Trp, Phe, Tyr or naphthylalanine; Xaa₂₆ is Ala or Leu; Xaa₂₇ is Ala or Lys; Xaa₂₈ is Ala or Asn; Z₁ is OH, NH₂, Gly-Z₂, Gly Gly-Z₂, Gly Gly Xaa₃₁-Z₂, Gly Gly Xaa₃₁ Ser-Z₂, Gly Gly Xaa₃₁ Ser Ser-Z₂, Gly Gly Xaa₃₁ Ser Ser Gly-Z₂, Gly Gly Xaa₃₁ Ser Ser Gly Ala-Z₂, Gly Gly Xaa₃₁ Ser Ser Gly Ala Xaa₃₆-Z₂, Gly Gly Xaa₃₁ Ser Ser Gly Ala Xaa₃₆ Xaa₃₇-Z₂, Gly Gly Xaa₃₁ Ser Ser Gly Ala Xaa₃₆ Xaa₃₇ Xaa₃₈-Z₂ or Gly Gly Xaa₃₁ Ser Ser Gly Ala Xaa₃₆ Xaa₃₇ Xaa₃₈ Xaa₃₉-Z₂; wherein Xaa₃₁, Xaa₃₆, Xaa₃₇ and Xaa₃₈ are independently Pro, homoproline, 3Hyp, 4Hyp, thioproline, N-alkylglycine, N-alkylpentylglycine or N-alkylalanine; Xaa₃₉ is Ser or Tyr; and Z₂ is OH or NH₂; provided that no more than three of Xaa₃, Xaa₄, Xaa₅, Xaa₆, Xaa₈, Xaa₉, Xaa₁₀, Xaa₁₁, Xaa₁₂, Xaa₁₃, Xaa₁₄, Xaa₁₅, Xaa₁₆, Xaa₁₇, Xaa₁₉, Xaa₂₀, Xaa₂₁, Xaa₂₄, Xaa₂₅, Xaa₂₆, Xaa₂₇ and Xaa₂₈ are Ala; and provided also that, if Xaa₁ is His, Arg or Tyr, then at least one of Xaa₃, Xaa₄ and Xaa₉ is Ala.

Preferred N-alkyl groups for N-alkylglycine, N-alkylpentylglycine and N-alkylalanine include lower alkyl groups preferably of 1 to about 6 carbon atoms, more preferably of 1 to 4 carbon atoms.

Suitable compounds of formula (IT) include those described in WO 99/25728 (i.e., application Serial No. PCT/US98/24273, filed Nov. 13, 1998, entitled "Novel Exendin Agonist Compounds"), identified therein in Examples 1-89 ("Compounds 1-89," respectively), as well as those corresponding compounds identified therein in Examples 104 and 105.

Preferred such exendin agonist compounds include those wherein Xaa₁ is His, Ala or Norval. More preferably Xaa₁ is His or Ala. Most preferably Xaa₁ is His. Preferred are those compounds of formula (II) wherein Xaa₂ is Gly. Preferred are those compounds of formula (II) wherein Xaa₃ is Ala. Preferred are those compounds of formula (II) wherein Xaa₄ is Ala. Preferred are those compounds of formula (II) wherein Xaa₉ is Ala. Preferred are those compounds of formula (II) wherein Xaa₁₄ is Leu, pentylglycine or Met. Preferred compounds of formula (II) are those wherein Xaa₂₅ is Trp or Phe. Preferred compounds of formula (II) are those where Xaa₆ is Ala, Phe or naphthylalanine; Xaa₂₂ is Phe or naphthylalanine; and Xaa₂₃ is Ile or Val. Preferred are compounds of formula (II) wherein Xaa₃₁, Xaa₃₆, Xaa₃₇ and Xaa₃₈ are independently selected from Pro, homoproline, thioproline and N-alkylalanine. Preferably Z₁ is —NH₂. Preferably Z₂ is —NH₂.

According to one aspect, preferred are compounds of formula (II) wherein Xaa₁ is Ala, His or Tyr, more preferably Ala or His; Xaa₂ is Ala or Gly; Xaa₆ is Phe or naphthylalanine; Xaa₁₄ is Ala, Leu, pentylglycine or Met; Xaa₂₂ is Phe or naphthylalanine; Xaa₂₃ is Ile or Val; Xaa₃₁, Xaa₃₆, Xaa₃₇ and Xaa₃₈ are independently selected from Pro, homoproline, thioproline or N-alkylalanine; and Xaa₃₉ is Ser or Tyr, more preferably Ser. More preferably Z₇ is —NH₂.

According to an especially preferred aspect, especially preferred compounds include those of formula (II) wherein: Xaa₁ is His or Ala; Xaa₂ is Gly or Ala; Xaa₃ is Ala, Asp or Glu; Xaa₄ is Ala or Gly; Xaa₅ is Ala or Thr; Xaa₆ is Phe or naphthylalanine; Xaa₇ is Thr or Ser; Xaa₈ is Ala, Ser or Thr; Xaa₉ is Ala, Asp or Glu; Xaa₁₀ is Ala, Leu or pentylglycine; Xaa₁₁ is Ala or Ser; Xaa₁₂ is Ala or Lys; Xaa₁₃ is Ala or Gln; Xaa₁₄ is Ala, Leu, Met or pentylglycine; Xaa₁₅ is Ala or Glu; Xaa₁₆ is Ala or Glu; Xaa₁₇ is Ala or Glu; Xaa₁₉ is Ala or Val; Xaa₂₀ is Ala or Arg; Xaa₂₁ is Ala or Leu; Xaa₂₂ is Phe or naphthylalanine; Xaa₂₃ is Ile, Val or tert-butylglycine; Xaa₂₄ is Ala, Glu or Asp; Xaa₂₅ is Ala, Trp or Phe; Xaa₂₆ is Ala or Leu; Xaa₂₇ is Ala or Lys; Xaa₂₈ is Ala or Asn; Z₁ is —OH, —NH₂, Gly-Z₂, Gly Gly-Z₂, Gly Gly Xaa₃₁-Z₂, Gly Gly Xaa₃₁ Ser-Z₂, Gly Gly Xaa₃₁ Ser Ser-Z₂, Gly Gly Xaa₃₁ Ser Ser Gly-Z₂, Gly Gly Xaa₃₁ Ser Ser Gly Ala-Z₂, Gly Gly Xaa₃₁ Ser Ser Gly Ala Xaa₃₆-Z₂, Gly Gly Xaa₃₁ Ser Ser Gly Ala Xaa₃₆ Xaa₃₇-Z₂, Gly Gly Xaa₃₁ Ser Ser Gly Ala Xaa₃₆ Xaa₃₇ Xaa₃₈-Z₂ or Gly Gly Xaa₃₁ Ser Ser Gly Ala Xaa₃₆ Xaa₃₇ Xaa₃₈ Xaa₃₉-Z₂; Xaa₃₁, Xaa₃₆, Xaa₃₇ and Xaa₃₈ being independently Pro homoproline, thioproline or N-methylalanine; and Z₂ being —OH or —NH₂; provided that no more than three of Xaa₃, Xaa₅, Xaa₆, Xaa₈, Xaa₁₀, Xaa₁₁, Xaa₁₂, Xaa₁₃, Xaa₁₄, Xaa₁₅, Xaa₁₆, Xaa₁₇, Xaa₁₉, Xaa₂₀, Xaa₂₁, Xaa₂₄, Xaa₂₅, Xaa₂₆, Xaa₂₇ and Xaa₂₈ are Ala; and provided also that, if Xaa₁ is His, Arg or Tyr, then at least one of Xaa₃, Xaa₄ and Xaa₉ is Ala. Especially preferred compounds of formula (II) include those described in WO 99/25728 (i.e., application Serial No. PCT/US98/24273, filed Nov. 13, 1998, entitled "Novel Exendin Agonist Compounds") as having the amino acid sequence of SEQ ID NOs: 5-93 therein.

According to an especially preferred aspect, provided are compounds of formula (II) where Xaa₁₄ is Ala, Leu, Ile, Val or pentylglycine, more preferably Leu or pentylglycine, and Xaa₂₅ is Ala, Phe, Tyr or naphthylalanine, more preferably Phe or naphthylalanine. These compounds will be less susceptible to oxidative degration, both in vitro and in vivo, as well as during synthesis of the compound.

Formula III

Also within the scope of the present invention are narrower genera of compounds having peptides of various lengths, for example genera of compounds which do not include peptides having a length of 28, 29 or 30 amino acid residues, respectively. Additionally, the present invention includes narrower genera of compounds described in PCT application Serial No. PCT/US98/24210, filed Nov. 13, 1998, entitled "Novel Exendin Agonist Compounds," published as WO 99/25727, and having particular amino acid sequences, for example, compounds of the formula (III) [SEQ ID NO: 43]:

Xaa$_1$ Xaa$_2$ Xaa$_3$ Gly Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{18}$ Xaa$_{19}$ Xaa$_{20}$ Xaa$_{21}$ Xaa$_{22}$ Xaa$_{23}$ Xaa$_{24}$ Xaa$_{25}$

Xaa$_{26}$ Xaa$_{27}$ Xaa$_{28}$-Z$_1$;

wherein Xaa$_1$ is His or Arg; Xaa$_2$ is Gly or Ala; Xaa$_3$ is Ala, Asp or Glu; Xaa$_5$ is Ala or Thr; Xaa$_6$ is Ala, Phe or naphthylalanine; Xaa$_7$ is Thr or Ser; Xaa$_8$ is Ala, Ser or Thr; Xaa$_9$ is Asp or Glu; Xaa$_{10}$ is Ala, Leu or pentylglycine; Xaa$_{11}$ is Ala or Ser; Xaa$_{12}$ is Ala or Lys; Xaa$_{13}$ is Ala or Gln; Xaa$_{14}$ is Ala, Leu or pentylglycine; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Phe or naphthylalanine; Xaa$_{23}$ is Ile, Val or tert-butylglycine; Xaa$_{24}$ is Ala, Glu or Asp; Xaa$_{25}$ is Ala, Trp, or Phe; Xaa$_{26}$ is Ala or Leu; Xaa$_{27}$ is Ala or Lys; Xaa$_{28}$ is Ala or Asn; Z$_1$ is OH, NH$_2$, Gly-Z$_2$, Gly Gly-Z$_2$, Gly Gly Xaa$_{31}$-Z$_2$, Gly Gly Xaa$_{31}$ Ser-Z$_2$, Gly Gly Xaa$_{31}$ Ser Ser-Z$_2$, Gly Gly Xaa$_{31}$ Ser Ser Gly-Z$_2$, Gly Gly Xaa$_{31}$ Ser Ser Gly Ala-Z$_2$, Gly Gly Xaa$_{31}$ Ser Ser Gly Ala Xaa$_{36}$-Z$_2$, Gly Gly Xaa$_{31}$ Ser Ser Gly Ala Xaa$_{36}$ Xaa$_{37}$-Z$_2$ or Gly Gly Xaa$_{31}$ Ser Ser Gly Ala Xaa$_{36}$ Xaa$_{37}$ Xaa$_{38}$-Z$_2$; Xaa$_{31}$, Xaa$_{36}$, Xaa$_{37}$ and Xaa$_{38}$ are independently selected from the group consisting of Pro, homoproline, thioproline and N-methylylalanine; and Z$_2$ is OH or NH$_2$; provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala; and pharmaceutically acceptable salts thereof.

Formula IV

Additionally, the present invention includes narrower genera of peptide compounds described in PCT Application Serial No. PCT/US98/24273, filed Nov. 13, 1998, entitled "Novel Exendin Agonist Compounds," published as WO 99/25728, as having particular amino acid sequences, for example, compounds of the formula [IV] [SEQ ID NO: 44]:

Xaa$_1$ Xaa$_2$ Xaa$_3$ Xaa$_5$ Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{18}$ Xaa$_{19}$ Xaa$_{20}$ Xaa$_{21}$ Xaa$_{22}$ Xaa$_{23}$ Xaa$_{24}$ Xaa$_{25}$

Xaa$_{26}$ Xaa$_{27}$ Xaa$_{28}$-Z$_1$;

wherein Xaa$_1$ is His or Ala; Xaa$_2$ is Gly or Ala; Xaa$_3$ is Ala, Asp or Glu; Xaa$_4$ is Ala or Gly; Xaa$_5$ is Ala or Thr; Xaa$_6$ is Ala, Phe or naphthylalanine; Xaa$_7$ is Thr or Ser; Xaa$_8$ is Ala, Ser or Thr; Xaa$_9$ is Ala, Asp or Glu; Xaa$_{10}$ is Ala, Leu or pentylglycine; Xaa$_{11}$ is Ala or Ser; Xaa$_{12}$ is Ala or Lys; Xaa$_{13}$ is Ala or Gln; Xaa$_{14}$ is Ala, Leu, Met or pentylglycine; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Phe or naphthylalanine; Xaa$_{23}$ is Ile, Val or tert-butylglycine; Xaa$_{24}$ is Ala, Glu or Asp; Xaa$_{25}$ is Ala, Trp or Phe; Xaa$_{26}$ is Ala or Leu; Xaa$_{27}$ is Ala or Lys; Xaa$_{28}$ is Ala or Asn; Z$_1$ is OH, NH$_2$, Gly-Z$_2$, Gly Gly-Z$_2$, Gly Gly Xaa$_{31}$-Z$_2$, Gly Gly Xaa$_{31}$ Ser-Z$_2$, Gly Gly Xaa$_{31}$ Ser Ser-Z$_2$, Gly Gly Xaa$_{31}$ Ser Ser Gly-Z$_2$, Gly Gly Xaa$_{31}$ Ser Ser Gly Ala-Z$_2$, Gly Gly Xaa$_{31}$ Ser Ser Gly Ala Xaa$_{36}$-Z$_2$, Gly Gly Xaa$_{31}$ Ser Ser Gly Ala Xaa$_{36}$ Xaa$_{37}$-Z$_2$, Gly Gly Xaa$_{31}$ Ser Ser Gly Ala Xaa$_{36}$ Xaa$_{37}$ Xaa$_{38}$-Z$_2$, Gly Gly Xaa$_{31}$ Ser Ser Gly Ala Xaa$_{36}$ Xaa$_{37}$ Xaa$_{38}$ Ser-Z$_2$; Xaa$_{31}$, Xaa$_{36}$, Xaa$_{37}$ and Xaa$_{38}$ are independently Pro, homoproline, thioproline, or N-methylalanine; and Z$_2$ is —OH or —NH$_2$; provided that no more than three of Xaa$_3$, Xaa$_5$, Xaa$_6$, Xaa$_8$, Xaa$_{10}$, Xaa$_1$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$, and Xaa$_{28}$ are Ala; and provided that, if Xaa$_1$ is His then at least one of Xaa$_3$, Xaa$_4$ and Xaa$_9$ is Ala; and pharmaceutically acceptable salts thereof.

Preferred compounds of formula (IV) include those wherein Xaa$_1$ is His or Ala. Preferably, Xaa$_1$ is His. Preferred compounds of formula (IV) include those wherein Xaa$_2$ is Gly. Preferred compounds of formula (IV) include those wherein Xaa$_4$ is Ala. Preferred compounds of formula (IV) include those wherein Xaa$_9$ is Ala. Preferred compounds of formula (IV) include those wherein Xaa$_{14}$ is Leu, pentylglycine or Met. Preferred compounds of formula (IV) include those wherein Xaa$_{25}$ is Trp or Phe. Preferred compounds of formula (IV) include those wherein Xaa$_6$ is Ala, Phe or naphthylalanine; Xaa$_{22}$ is Phe or naphthylalanine; and Xaa$_{23}$ is Ile or Val. Preferred compounds of formula (IV) include those wherein Z$_1$ is —NH$_2$. Preferred compounds of formula (IV) include those wherein Xaa$_{31}$, Xaa$_{36}$, Xaa$_{37}$ and Xaa$_{38}$ are independently selected from the group consisting of Pro, homoproline, thioproline and methylalanine. Preferred compounds of formula (IV) include those wherein Z$_2$ is —NH$_2$. Preferred compounds of formula (IV) include those wherein Z$_1$ is —NH$_2$.

Preferred compounds of formula (IV) include those having an amino acid sequence described in PCT application Serial No. PCT/US98/24273, filed Nov. 13, 1998, entitled "Novel Exendin Agonist Compounds," published as WO 99/25728, as being selected from SEQ ID NOs: 95-110 therein.

Formula V

Also provided are compounds described in PCT application PCT/US98/24210, filed Nov. 13, 1998, entitled "Novel Exendin Agonist Compounds," published as WO 99/25727, including compounds of the formula (V) [SEQ ID NO: 45]:

Xaa$_1$ Xaa$_2$ Xaa$_3$ Gly Xaa$_5$ Xaa$_6$ Xaa$_7$ Xaa$_8$ Xaa$_9$ Xaa$_{10}$

Xaa$_{11}$ Xaa$_{12}$ Xaa$_{13}$ Xaa$_{14}$ Xaa$_{15}$ Xaa$_{16}$ Xaa$_{17}$ Ala

Xaa$_{19}$ Xaa$_{20}$ Xaa$_{21}$ Xaa$_{22}$ Xaa$_{23}$ Xaa$_{24}$ Xaa$_{25}$ Xaa$_{26}$

X$_1$-Z$_1$;

wherein Xaa$_1$ is Ala, His, Arg or Tyr or 4-imidazopropionyl; Xaa$_2$ is Ser, Gly, Ala or Thr; Xaa$_3$ is Ala, Asp or Glu; Xaa$_5$ is Ala or Thr; Xaa$_6$ is Ala, Phe, Tyr or naphthylalanine; Xaa$_7$ is Thr or Ser; Xaa$_8$ is Ala, Ser or Thr; Xaa$_9$ is Ala, Asp or Glu; Xaa$_{10}$ is Ala, Leu, Ile, Val, pentylglycine or Met; Xaa$_{11}$ is Ala or Ser; Xaa$_{12}$ is Ala or Lys; Xaa$_{13}$ is Ala or Gln; Xaa$_{14}$ is Ala, Leu, Ile, pentylglycine, Val or Met; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala, Leu or Lys-NH$^\epsilon$—R where R is Lys, Arg, C$_1$-C$_{10}$ straight chain or branched alkanoyl or cycloalkylalkanoyl; $Xaa_{22}$ is Phe, Tyr or naphthylalanine; $Xaa_{23}$ is Ile, Val, Leu, pentylglycine, tert-butylglycine or Met; $Xaa_{24}$ is Ala, Glu or Asp; $Xaa_{25}$ is Ala, Trp, Phe, Tyr or naphthylalanine; $Xaa_{26}$ is Ala or Leu; $X_1$ is Lys Asn, Asn Lys, Lys-NH$^\epsilon$—R Asn, Asn Lys-NH$^\epsilon$—R, Lys-NH$^\epsilon$—R Ala, Ala Lys-NH$^\epsilon$—R where R is Lys, Arg, $C_1$-$C_{10}$ straight chain or branched alkanoyl or cycloalkylalkanoyl; $Z_1$ is OH, NH$_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$ or Gly Gly $Xaa_{31}$ Ser Ser Gly Ala $Xaa_{36}$ $Xaa_{37}$ $Xaa_{38}$-$Z_2$; wherein $Xaa_{31}$, $Xaa_{36}$, $Xaa_{37}$ and $Xaa_{38}$ are independently selected from the group consisting of Pro, homoproline, 3Hyp, 4Hyp, thioproline, N-alkylglycine, N-alkylpentylglycine and N-alkylalanine; and $Z_2$ is —OH or —NH$_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, and $Xaa_{26}$ are Ala. Also within the scope of the present invention are pharmaceutically acceptable salts of the compound of formula (V) and pharmaceutical compositions including said compounds and salts thereof.

Preferred exendin agonist compounds of formula (V) include those wherein $Xaa_1$ is His, Tyr or 4-imidazopropionyl. More preferably $Xaa_1$ is His. Preferred are those compounds of formula (V) wherein $Xaa_1$ is 4-imidazopropionyl. Preferred are those compounds of formula (V) wherein $Xaa_2$ is Gly. Preferred compounds of formula (V) are those wherein $Xaa_{14}$ is Leu, pentylglycine or Met. Preferred compounds of formula (V) are those wherein $Xaa_{25}$ is Trp or Phe.

According to one aspect, preferred are compounds of formula (V) wherein $Xaa_6$ is Phe or naphthylalanine; and $Xaa_{22}$ is Phe or naphthylalanine; and $Xaa_{23}$ is Ile or Val. More preferably, $Z_1$ is —NH$_2$. According to one aspect, especially preferred are such compounds of formula (V) wherein $Xaa_{31}$, $Xaa_{36}$, $Xaa_{37}$ and $Xaa_{38}$ are independently selected from the group consisting of Pro, homoproline, thioproline and N-alkylalanine. More preferred, $Z_2$ is —NH$_2$.

Preferred compounds of formula (V) include those wherein $X_1$ is Lys Asn, Lys-NH$^\epsilon$—R Asn, or Lys-NH$^\epsilon$—R Ala where R is Lys, Arg, $C_1$-$C_{10}$ straight chain or branched alkanoyl. Preferred compounds of formula (V) include compounds described in PCT application Serial No. PCT/US98/24210, filed Nov. 13, 1998, entitled "Novel Exendin Agonist Compounds," published as WO 99/25727, and identified therein as Compound Nos. 62-69.

Preferred are those compounds of formula (V) wherein $Xaa_2$ is Gly. Preferred are those compounds of formula (V) wherein $Xaa_3$ is Ala. Preferred are those compounds of formula (V) wherein $Xaa_9$ is Ala. Preferred are those compounds of formula (V) wherein $Xaa_{14}$ is Leu, pentylglycine or Met. Preferred compounds of formula (V) are those wherein $Xaa_{25}$ is Trp or Phe. Preferred compounds of formula (V) are those where $Xaa_6$ is Ala, Phe or naphthylalanine; $Xaa_{22}$ is Phe or naphthylalanine; and $Xaa_{23}$ is Ile or Val. Preferred are compounds of formula (V) wherein $Xaa_{31}$, $Xaa_{36}$, $Xaa_{37}$ and $Xaa_{38}$ are independently selected from Pro, homoproline, thioproline and N-alkylalanine. Preferably $Z_1$ is —NH$_2$. Preferably $Z_2$ is —NH$_2$.

According to one aspect, preferred are compounds of formula (V) wherein $Xaa_1$ is Ala, His or Tyr, more preferably Ala or His; $Xaa_2$ is Ala or Gly; $Xaa_6$ is Phe or naphthylalanine; $Xaa_{14}$ is Ala, Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. More preferably $Z_1$ is —NH$_2$.

According to an especially preferred aspect, especially preferred compounds include those of formula (V) wherein: $Xaa_1$ is His or Ala; $Xaa_2$ is Gly or Ala; $Xaa_3$ is Ala, Asp or Glu; $Xaa_5$ is Ala or Thr; $Xaa_6$ is Phe or naphthylalanine; $Xaa_7$ is Thr or Ser; $Xaa_8$ is Ala, Ser or Thr; $Xaa_9$ is Ala, Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu, Met or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —NH$_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$ or Gly Gly $Xaa_{31}$ Ser Ser Gly Ala $Xaa_{36}$ $Xaa_{37}$ $Xaa_{38}$ $Xaa_{39}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —NH$_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, and $Xaa_9$ is Ala. Especially preferred compounds of formula (V) include those described in PCT application Serial No. PCT/US98/24210, filed Nov. 13, 1998, entitled "Novel Exendin Agonist Compounds," published as WO 99/25727, and having the amino acid sequences identified therein as SEQ ID NOs: 5-93.

According to an especially preferred aspect, provided are compounds of formula (V) where $Xaa_{14}$ is Ala, Leu, Ile, Val or pentylglycine, more preferably Leu or pentylglycine, and $Xaa_{25}$ is Ala, Phe, Tyr or naphthylalanine, more preferably Phe or naphthylalanine. These compounds will be less susceptible to oxidative degration, both in vitro and in vivo, as well as during synthesis of the compound.

Formula VI

Also provided are peptide compounds described in PCT Application Serial No. PCT/US98/24273, filed Nov. 13, 1998, entitled "Novel Exendin Agonist Compounds," published as WO 99/25728, including compounds of the formula (VI) [SEQ ID NO: 46]:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $X_1$-$Z_1$;

wherein $Xaa_1$ is His, Arg, Tyr, Ala, Norval, Val, Norleu or 4-imidazopropionyl; $Xaa_2$ is Ser, Gly, Ala or Thr; $Xaa_3$ is Ala, Asp or Glu; $Xaa_4$ is Ala, Norval, Val, Norleu or Gly; $Xaa_5$ is Ala or Thr; $Xaa_6$ is Ala, Phe, Tyr or naphthylalanine; $Xaa_7$ is Thr or Ser; $Xaa_8$ is Ala, Ser or Thr; $Xaa_9$ is Ala, Norval, Val, Norleu, Asp or Glu; $Xaa_{10}$ is Ala, Leu, Ile, Val, pentylglycine or Met; $Xaa_{11}$ is Ala or Ser; $Xaa_{12}$ is Ala or Lys; $Xaa_{13}$ is Ala or Gln; $Xaa_{14}$ is Ala, Leu, Ile, pentylglycine, Val or Met; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala, Leu or Lys-NH$^\epsilon$—R where R is Lys, Arg, $C_{1-10}$ straight chain or branched alkanoyl or cycloalleyl-alkanoyl; $Xaa_{22}$ is Phe, Tyr or naphthylalanine; $Xaa_{23}$ is Ile, Val, Leu, pentylglycine, tert-butylglycine or Met; $Xaa_{24}$ is Ala, Glu or Asp; $Xaa_{25}$ is Ala, Trp, Phe, Tyr or naphthylalanine; $Xaa_{26}$ is Ala or Leu; $X_1$ is Lys Asn, Asn Lys, Lys-NH$^\epsilon$—R Asn, Asn Lys-NH$^\epsilon$—R, Lys-NH$^\epsilon$—R Ala, Ala Lys-NH$^\epsilon$—R where R is Lys, Arg, $C_1$-$C_{10}$ straight chain or branched alkanoyl or cycloalkylalkanoyl; $Z_7$ is OH, NH$_2$, Gly-Z$_2$, Gly Gly-Z$_2$, Gly Gly Xaa$_{31}$-Z$_2$, Gly Gly Xaa$_{31}$ Ser-Z$_2$, Gly Gly Xaa$_{31}$ Ser Ser-Z$_2$, Gly Gly Xaa$_{31}$ Ser Ser Gly-Z$_2$, Gly Gly Xaa$_{31}$ Ser Ser Gly Ala-Z$_2$, Gly Gly Xaa$_{31}$ Ser Ser Gly Ala Xaa$_{36}$-Z$_2$, Gly Gly Xaa$_{31}$ Ser Ser Gly Ala Xaa$_{36}$ Xaa$_{37}$-Z$_2$, Gly Gly Xaa$_{31}$ Ser Ser Gly Ala Xaa$_{36}$ Xaa$_{37}$ Xaa$_{38}$-Z$_2$ or Gly Gly Xaa$_{31}$ Ser Ser Gly Ala Xaa$_{36}$ Xaa$_{37}$ Xaa$_{38}$ Xaa$_{39}$-Z$_2$; wherein Xaa$_{31}$, Xaa$_{36}$, Xaa$_{37}$ and Xaa$_{38}$ are independently selected from the group consisting of Pro, homoproline, 3Hyp, 4Hyp, thioproline, N-alkylglycine, N-alkylpentylglycine and N-alkylalanine; Xaa$_{31}$ is Ser or Tyr; and Z$_2$ is —OH or —NH$_2$; provided that no more than three of Xaa$_3$, Xaa$_4$, Xaa$_5$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, are Ala; and provided also that, if Xaa$_1$ is His, Arg, Tyr, or 4-imidazopropionyl then at least one of Xaa$_3$, Xaa$_4$ and Xaa$_9$ is Ala.

Preferred compounds of formula (VI) include those wherein Xaa$_1$ is His, Ala, Norval or 4-imidazopropionyl. Preferably, Xaa$_1$ is His, or 4-imidazopropionyl or Ala, more preferably His or 4-imidazopropionyl. Preferred compounds of formula (VI) include those wherein Xaa$_2$ is Gly. Preferred compounds of formula (VI) include those wherein Xaa$_4$ is Ala. Preferred compounds of formula (VI) include those wherein Xaa$_9$ is Ala. Preferred compounds of formula (VI) include those wherein Xaa$_{14}$ is Leu, pentylglycine or Met. Preferred compounds of formula (VI) include those wherein Xaa$_{25}$ is Trp or Phe. Preferred compounds of formula (VI) include those wherein Xaa$_6$ is Ala, Phe or naphthylalanine; Xaa$_{22}$ is Phe or naphthylalanine; and Xaa$_{23}$ is Ile or Val. Preferred compounds of formula (VI) include those wherein Z$_1$ is —NH$_2$. Preferred compounds of formula (VI) include those wherein Xaa$_{31}$, Xaa$_{36}$, Xaa$_{37}$ and Xaa$_{38}$ are independently selected from the group consisting of Pro, homoproline, thioproline and N-alkylalanine. Preferred compounds of formula (VI) include those wherein Xaa$_{39}$ is Ser or Tyr, preferably Ser. Preferred compounds of formula (VI) include those wherein Z$_2$ is —NH$_2$. Preferred compounds of formula (VI) include those 42 wherein Z$_1$ is —NH$_2$. Preferred compounds of formula (VI) include those wherein Xaa$_{21}$ is Lys-NH$^\epsilon$—R where R is Lys, Arg, $C_1$-$C_{10}$ straight chain or branched alkanoyl. Preferred compounds of formula (VI) include those wherein X$_1$ is Lys Asn, Lys-NH$^\epsilon$—R Asn, or Lys-NH$^\epsilon$—R Ala where R is Lys, Arg, $C_1$-$C_{10}$ straight chain or branched alkanoyl.

Preferred compounds of formula (VI) include those described in PCT Application Serial No. PCT/US98/24273, filed Nov. 13, 1998, entitled "Novel Exendin Agonist Compounds," published as WO 99/25728, as having an amino acid sequence selected from those identified therein as SEQ ID NOs: 95-110.

Formula VII

Compounds particularly useful according to the present invention are exendin agonist compounds described in U.S. patent application Ser. No. 09/003,869, filed Jan. 7, 1998, entitled "Use of Exendins And Agonists Thereof For The Reduction of Food Intake," issued as U.S. Pat. No. 5,956,026, including compounds of the formula (VII) [SEQ ID NO: 47]:

```
Xaa₁ Xaa₂ Xaa₃ Gly Thr Xaa₆ Xaa₇ Xaa₈ Xaa₉ Xaa₁₀

Ser Lys Gln Xaa₁₄ Glu Glu Glu Ala Val Arg Leu

Xaa₂₂ Xaa₂₃ Xaa₂₄ Xaa₂₅ Leu Lys Asn Gly Gly Xaa₃₁

Ser Ser Gly Ala Xaa₃₆ Xaa₃₇ Xaa₃₈ Xaa₃₉-Z
``` wherein Xaa$_1$ is His, Arg or Tyr; Xaa$_2$ is Ser, Gly, Ala or Thr; Xaa$_3$ is Asp or Glu; Xaa$_6$ is Phe, Tyr or naphthalanine; Xaa$_7$ is Thr or Ser; Xaa$_8$ is Ser or Thr; Xaa$_9$ is Asp or Glu; Xaa$_{10}$ is Leu, Ile, Val, pentylglycine or Met; Xaa$_{14}$ is Leu, Ile, pentylglycine, Val or Met; Xaa$_{22}$ is Phe, Tyr or naphthalanine; Xaa$_{23}$ is Ile, Val, Leu, pentylglycine, tert-butylglycine or Met; Xaa$_{24}$ is Glu or Asp; Xaa$_{25}$ is Trp, Phe, Tyr, or naphthylalanine; Xaa$_{31}$, Xaa$_{36}$, Xaa$_{37}$ and Xaa$_{38}$ are independently Pro, homoproline, 3Hyp, 4Hyp, thioproline, N-alkylglycine, N-alkylpentylglycine or N-alkylalanine; Xaa$_{39}$ is Ser, Thr or Tyr; and Z is OH or NH$_2$; with the proviso that the compound does not have the formula of either SEQ ID NOs: 1 or 2. Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds include those having amino acid sequences of SEQ ID NOs: 10 to 40. Also useful in the present invention are pharmaceutically acceptable salts of the compounds of formula (VII).

Preferred exendin agonist compounds include those wherein Xaa$_1$ is His or Tyr. More preferably Xaa$_1$ is His. Preferred are those compounds wherein Xaa$_2$ is Gly. Preferred are those compounds wherein Xaa$_{14}$ is Leu, pentylglycine or Met. Preferred compounds include those wherein Xaa$_{25}$ is Trp or Phe. Also preferred are compounds where Xaa$_6$ is Phe or naphthalanine; Xaa$_{23}$ is Ile or Val and Xaa$_{31}$, Xaa$_{36}$, Xaa$_{37}$ and Xaa$_{38}$ are independently selected from Pro, homoproline, thioproline or N-alkylalanine. Preferably N-alkylalanine has a N-alkyl group of 1 to about 6 carbon atoms. According to an especially preferred aspect, Xaa$_{36}$, Xaa$_{37}$ and Xaa$_{38}$ are the same amino acid reside. Preferred are compounds wherein Xaa$_{39}$ is Ser or Tyr, more preferably Ser. Preferably Z is —NH$_2$.

According to one aspect, preferred are compounds of formula (VII) wherein Xaa$_1$ is His or Tyr, more preferably His; Xaa$_2$ is Gly; Xaa$_6$ is Phe or naphthalanine; Xaa$_{14}$ is Leu, pentylglycine or Met; Xaa$_{22}$ is Phe or naphthalanine; Xaa$_{23}$ is Ile or Val; Xaa$_{31}$, Xaa$_{36}$, Xaa$_{37}$ and Xaa$_{38}$ are independently selected from Pro, homoproline, thioproline or N-alkylalanine; and Xaa$_{39}$ is Ser or Tyr, more preferably Ser. More preferably Z is —NH$_2$.

According to an especially preferred aspect, especially preferred compounds include those of formula (VII) wherein: Xaa$_1$ is His or Arg; Xaa$_2$ is Gly; Xaa$_3$ is Asp or Glu; Xaa$_6$ is Phe or napthylalanine; Xaa$_7$ is Thr or Ser; Xaa$_8$ is Ser or Thr; Xaa$_9$ is Asp or Glu; Xaa$_{10}$ is Leu or pentylglycine; Xaa$_{14}$ is Leu or pentylglycine; Xaa$_{22}$ is Phe or naphthalanine; Xaa$_{23}$ is Ile, Val or t-butyltylglycine; Xaa$_{24}$ is Glu or Asp; Xaa$_{25}$ is Trp or Phe; Xaa$_{31}$, Xaa$_{36}$, Xaa$_{37}$, and Xaa$_{38}$ are independently Pro, homoproline, thioproline, or N-methylalanine; Xaa$_{39}$ is Ser or Tyr: and Z is —OH or —NH$_2$; with the proviso that the compound does not have the formula of either SEQ ID NOs: 1 or 2. More preferably Z is —NH$_2$. Especially preferred compounds include those having the amino acid sequence of SEQ ID NOs: 10, 11, 22, 23, 24, 27, 29, 36, 37 and 40.

According to an especially preferred aspect, provided are compounds where Xaa$_{14}$ is Leu, Ile, Val or pentylglycine, more preferably Leu or pentylglycine, and Xaa$_{25}$ is Phe, Tyr or naphthylalanine, more preferably Phe or naphthylalanine. These compounds are believed to exhibit advantageous duration of action and to be less subject to oxidative degration, both in vitro and in vivo, as well as during synthesis of the compound.

Formula VIII

Also provided are compounds described in PCT Application Serial No. PCT/US98/16387, filed Aug. 6, 1998, entitled "Novel Exendin Agonist Compounds," published as WO 99/07404, including compounds of the formula (VIII) [SEQ ID NO: 48]:

Xaa$_1$ Xaa$_2$ Xaa$_3$ Gly Thr Xaa$_6$ Xaa$_7$ Xaa$_8$ Xaa$_9$ Xaa$_{10}$

Ser Lys Gln Xaa$_{14}$ Glu Glu Glu Ala Val Arg Leu

Xaa$_{22}$ Xaa$_{23}$ Xaa$_{24}$ Xaa$_{25}$ Leu X$_1$ Gly Gly Xaa$_{31}$ Ser

Ser Gly Ala Xaa$_{36}$ Xaa$_{37}$ Xaa$_{38}$ Xaa$_{39}$-Z wherein Xaa$_1$ is His, Arg, Tyr or 4-imidazopropionyl; Xaa$_2$ is Ser, Gly, Ala or Thr; Xaa$_3$ is Asp or Glu; Xaa$_6$ is Phe, Tyr or naphthylalanine; Xaa$_7$ is Thr or Ser; Xaa$_8$ is Ser or Thr; Xaa$_9$ is Asp or Glu; Xaa$_{10}$ is Leu, Ile, Val, pentylglycine or Met; Xaa$_{14}$ is Leu, Ile, pentylglycine, Val or Met; Xaa$_{22}$ is Phe, Tyr or naphthylalanine; Xaa$_{23}$ is Ile, Val, Leu, pentylglycine, tert-butylglycine or Met; Xaa$_{24}$ is Glu or Asp; Xaa$_{25}$ is Trp, Phe, Tyr, or naphthylalanine; X$_1$ is Lys Asn, Asn Lys, Lys-NH$^\epsilon$—R Asn, Asn Lys-NH$^\epsilon$—R where R is Lys, Arg, C$_1$-C$_{10}$ straight chain or branched alkanoyl or cycloalkylalkanoyl; Xaa$_{31}$, Xaa$_{36}$, Xaa$_{37}$ and Xaa$_{38}$ are independently Pro, homoproline, 3Hyp, 4Hyp, thioproline, N-alkylglycine, N-alkylpentylglycine or N-alkylalanine; Xaa$_{39}$ is Ser, Thr or Tyr; and Z is —OH or —NH$_2$; with the proviso that the compound does not have the formula of either SEQ ID NOs: 1 or 2.

Suitable compounds of formula (VIII) include compounds described in PCT Application Serial No. PCT/US98/16387, filed Aug. 6, 1998, entitled "Novel Exendin Agonist Compounds," published as WO 99/07404, having the amino acid sequences of SEQ ID NOs: 37-40 therein.

Preferred exendin agonist compounds of formula (VIII) include those wherein Xaa$_1$ is His, Tyr or 4-imidazopropionyl. More preferably, Xaa$_1$ is His or 4-imidazopropionyl. Preferred are those compounds of formula (VIII) wherein Xaa$_2$ is Gly. Preferred are those compounds of formula (VIII) wherein Xaa$_{14}$ is Leu, pentylglycine or Met. Preferred are those compounds of formula (VIII) wherein Xaa$_{25}$ is Trp or Phe. Preferred are those compounds of formula (VIII) wherein X$_1$ is Lys Asn, or Lys-NH$^\epsilon$—R Asn, where R is Lys, Arg, C$_1$-C$_{10}$ straight chain or branched alkanoyl.

Also preferred are compounds of formula (VIII) wherein Xaa$_6$ is Phe or naphthylalanine; Xaa$_{22}$ is Phe or naphthylalanine; Xaa$_{23}$ is Ile or Val and Xaa$_{31}$, Xaa$_{36}$, Xaa$_{37}$ and Xaa$_{38}$ are independently selected from Pro, homoproline, thioproline or N-alkylalanine. According to an especially preferred aspect, Xaa$_{39}$ is Ser or Tyr. Preferred are those such compounds wherein Xaa$_{39}$ is Ser. Preferably, Z is —NH$_2$.

According to one preferred aspect, preferred are compounds of formula (VIII) wherein Xaa$_6$ is Phe or naphthylalanine; Xaa$_{22}$ is Phe or naphthylalanine; Xaa$_{23}$ is Ile or Val, X$_1$ is Lys Asn, or Lys-NH$^\epsilon$—R Asn, where R is Lys, Arg, C$_1$-C$_{10}$ straight chain or branched alkanoyl and Xaa$_{31}$, Xaa$_{36}$, Xaa$_{37}$ and Xaa$_{38}$ are independently selected from Pro, homoproline, thioproline or N-alkylalanine.

Preparation of Modified Exendins and Exendin Agonists

The modified exendins and exendin agonists of the present invention may be made by linking one or more polyethylene glycol polymers to an exendin or exendin agonist. The synthesis of exendins and exendin agonists is thus described first, followed by methodology for linking the polyethylene glycol polymer(s) to the exendin or exendin agonist.

Preparation of Exendins and Exendin Agonists

Exendins and exendin agonist compounds such as exendin analogs and exendin derivatives, described herein may be prepared through peptide purification as described in, for example, Eng, et al., J. Biol. Chem. 265:20259-62, 1990; and Eng, et al., J. Biol. Chem. 267:7402-05, 1992, hereby incorporated by reference herein. Alternatively, exendins and exendin agonist peptides may be prepared by methods known to those skilled in the art, for example, as described in Raufman, et al. (J. Biol. Chem. 267:21432-37, 1992), hereby incorporated by reference herein, using standard solid-phase peptide synthesis techniques and preferably an automated or semiautomated peptide synthesizer. The compounds that constitute active ingredients of the formulations and dosages of the present invention may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: BSD-112344.1-Arg (Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu(t-Bu), Fmoc-His (Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−50° C. to 0° C., 1 hour). The peptide may be extracted from the resin with alternating water and acetic acid, and the filtrates lyophilized. The Fmoc-peptide resins may be cleaved according to standard methods (Introduction to Cleavage Techniques, Applied Biosystems, Inc., 1990, pp. 6-12). Peptides may also be assembled using an Advanced Chem Tech Synthesizer (Model MPS 350, Louisville, Ky.).

Peptides may be purified by reverse phase high performance liquid chromatography (RP-HPLC) (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen, et al., The Pico Tag Method: A Manual of Advanced Techniques for Amino Acid Analysis, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried and on a VG-Trio machine.

Peptide active ingredient compounds useful in the formulations and dosages of the invention may also be prepared using recombinant DNA techniques, using methods now known in the art. See, e.g., Sambrook et al., *Molecular Cloning: A Laboratory Manual*, 2d Ed., Cold Spring Harbor (1989). Alternatively, such compounds may be prepared by homogeneous phase peptide synthesis methods. Non-peptide compounds useful in the present invention may be prepared by art-known methods. For example, phosphate-containing amino acids and peptides containing such amino acids, may be prepared using methods known in the art. See, e.g., Bartlett and Landen, *Biorg. Chem.* 14:356-377 (1986).

Conjugation of Polyethylene Glycol Polymers

There are several strategies for coupling PEG to peptides/proteins. See, Francis, Int. J. Hematology 68:1 (1998); Gombotz, Bioconjugate Chem. 6:150 (1995); and Delgado, Crit. Rev. Therap. Drug Carrier Sys. 9:249 (1992) all of which are incorporated herein by reference in their entirety. Those skilled in the art, therefore, will be able to utilize such well-known techniques for linking one or more polyethylene glycol polymers to the exendins and exendin agonists described herein. Suitable polyethylene glycol polymers typically are commercially available or may be made by techniques well know to those skilled in the art. The polyethylene glycol polymers preferably have molecular weights between 500 and 20,000 and may be branched or straight chain polymers.

The attachment of a PEG on an intact peptide or protein can be accomplished by coupling to amino, carboxyl or thiol groups. These groups will typically be the N and C termini and on the side chains of such naturally occurring amino acids as lysine, aspartic acid, glutamic acid and cysteine. Since exendin 4 and other exendins and exendin agonists can be prepared by solid phase peptide chemistry techniques, a variety of moieties containing diamino and dicarboxylic groups with orthogonal protecting groups can be introduced for conjugation to PEG.

The present invention also provides for conjugation of an exendin or exendin agonist to one or more polymers other than polyethylene glycol which can regulate kidney clearance in a manner similar to polyethylene glycol. Examples of such polymers include albumin and gelatin. See, Gombotz and Pettit, *Bioconjugate Chem.*, 6:332-351, 1995, which is incorporated herein by reference in its entirety.

Utility

The formulations and dosages described herein are useful in view of their pharmacological properties. In particular, the compounds described herein possess activity as agents to reduce glucagon levels and suppress glucagon secretion, as evidenced by the ability to lower glucagon levels in animals and humans. They can be used to treat conditions or diseases that can be alleviated by reducing glucagon levels and suppressing glucagon secretion.

The compounds referenced above may form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g., sodium and potassium salts, and alkali earth salts, e.g., calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Formulation and Administration

Exendin and exendin agonist formulations and dosages of the invention are useful in view of their exendin-like effects, and may conveniently be provided in the form of formulations suitable for parenteral (including intravenous, intramuscular and subcutaneous) administration. Also described herein are formulations and dosages useful in alternative delivery routes, including oral, nasal, buccal, sublingual and pulmonary.

The feasibility of alternate routes of delivery for exendin-4 has been explored by measuring exendin-4 in the circulation in conjunction with observation of a biologic response, such as plasma glucose lowering in diabetic animals, after administration. Passage of exendin-4 has been investigated across several surfaces, the respiratory tract (nasal, tracheal and pulmonary routes) and the gut (sublingual, gavage and intraduodenal routes). Biologic effect and appearance of exendin-4 in blood have been observed with each route of administration via the respiratory tract, and with sublingual and gavaged peptide via the gastrointestinal tract. Intra-tracheal administration, nasal administration, administration via the gut, and sublingual administration have all been described.

In some cases, it will be convenient to provide a modified exendin or exendin agonist and another anti-glucagon agent, such as an amylin or an amylin agonist, in a single composition or solution for administration together. In other cases, it may be more advantageous to administer another anti-glucagon agent separately from the exendin, exendin agonist, or modified exendin or exendin agonist. In yet other cases, it may be beneficial to provide an exendin, exendin agonist, or modified exendin or exendin agonist either co-formulated or separately with other glucagon lowering agents such as amylin. A suitable administration format may best be determined by a medical practitioner for each patient individually. Suitable pharmaceutically acceptable carriers and their formulation are described in standard formulation treatises, e.g., Remington's Pharmaceutical Sciences by E. W. Martin. See also Wang, Y. J. and Hanson, M. A. "Parenteral Formulations of Proteins and Peptides: Stability and Stabilizers," Journal of Parenteral Science and Technology, Technical Report No. 10, Supp. 42:2S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 3.0 to about 7.0, more specifically from about 4.0 to 6.0, and preferably from about 4.0 to about 5.0. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/ acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The claimed compounds can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

If desired, solutions of the above compositions may be thickened with a thickening agent such as methylcellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

Other pharmaceutically acceptable carriers and their formulation are described in standard formulation treatises, e.g., Remington's Pharmaceutical Sciences by E. W. Martin. See also Wang, Y. J. and Hanson, M. A. "Parenteral Formulations of Proteins and Peptides: Stability and Stabilizers," Journal of Parenteral Science and Technology, Technical Report No. 10, Supp. 42:2S (1988).

For use by the physician, the compounds will be provided in dosage unit form containing an amount of an exendin, exendin agonist, or modified exendin or exendin agonist, with or without another anti-glucagon agent. Therapeutically effective amounts of an exendin, exendin agonist, or modified exendin or exendin agonist for use in the control of glucagon and in conditions in which glucagon levels are beneficially lowered or regulated are those that decrease post-prandial blood glucagon levels as desired. In diabetic or glucose intolerant individuals, plasma glucagon levels may be higher than in normal individuals. In such individuals, beneficial reduction or "smoothing" of post-prandial blood glucagon levels, may be obtained. As will be recognized by those in the field, an effective amount of therapeutic agent will vary with many factors including the age and weight of the patient, the patient's physical condition, the glucagon level or level of inhibition of glucagon suppression to be obtained, and other factors.

Such pharmaceutical compositions are useful in causing glucagon to be lowered in a subject and may be used as well in other disorders where lowered or suppressed glucagon is beneficially reduced.

The effective daily anti-glucagon dose of the compounds will typically be in the range of 0.01 or 0.03 to about 5 mg/day, preferably about 0.01 or 0.5 to 2 mg/day and more preferably about 0.01 or 0.1 to 1 mg/day, for a 70 kg patient, administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of, for example, diabetes mellitus as manifested by elevated glucagon. Administration may be by injection, preferably subcutaneous or intramuscular. Orally active compounds may be taken orally, however dosages should be increased 5-10 fold.

Generally, in treating or preventing elevated, inappropriate, or undesired post-prandial blood glucagon levels, the compounds of this invention may be administered to patients in need of such treatment in a dosage ranges similar to those given above, however, the compounds are administered more frequently, for example, one, two, or three times a day. Particularly preferred are the exendin and exendin agonist formulations and dosages and routes of administration thereof described commonly owned WO 00/41546 and WO 00/41548 (i.e., claiming priority to U.S. Provisional Application 60/116,380, entitled "Novel Exendin Agonist Formulations And Methods Of Administration Thereof," filed Jan. 14, 1999 (and the corresponding PCT application claiming priority from it that was filed on Jan. 14, 2000, Ser. No. PCT/US00/00942, and U.S. Provisional Application 60/175,365, entitled "Use of Exendins and Agonists Thereof for Modulation of Triglyceride Levels and Treatment of Dyslipidemia," filed Jan. 10, 2000), from which this application claims priority and the disclosures of which have been incorporated by referenced in their entirety as if fully set forth herein.

A form of repository or "depot" slow release preparation may be used so that therapeutically effective amounts of the preparation are delivered into the bloodstream over many hours or days following transdermal injection or other form of delivery.

The effective daily doses of the compounds are described. The exact dose to be administered may be determined by the attending clinician and may be further dependent upon the efficacy of the particular exendin or exendin agonist compound used, as well as upon the age, weight and condition of the individual. The optimal mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

In particular, the formulation which best supports a parenteral liquid dosage form is one in which the active ingredient(s) is stable with adequate buffering capacity to maintain the pH of the solution over the intended shelf life of the product. The dosage form should be either an isotonic and/or an iso-osmolar solution to either facilitate stability of the active ingredient or lessen the pain on injection or both. Devices that deliver very small injection volumes, however, may not require that the formulation be either isotonic and/or iso-osmolar. If the dosage form is packaged as a unit-dose, then a preservative may be included but is not required. If, however, the dosage form is packaged in a multi-use container, then a preservative is necessary.

These dosage forms include approximately 0.005 to about 0.4%, more specifically from about 0.005 to about 0.02%, or from about 0.005 to about 0.05% (w/v), respectively of the active ingredient in an aqueous system along with approximately 0.02 to 0.5% (w/v) of an acetate, phosphate, citrate or glutamate or similar buffer either alone or in combination to obtain a pH of the final composition of approximately 3.0 to 7.0, more specifically from about pH 4.0 to about 6.0, or from about 4.0 to 5.0, as well as either approximately 1.0 to 10% (w/v) of a carbohydrate or polyhydric alcohol iso-osmolality modifier (preferably mannitol) or up to about 0.9% saline or a combination of both leading to an isotonic or an iso-osmolar solution in an aqueous continuous phase. Approximately 0.005 to 1.0% (w/v) of an anti-microbial preservative selected from the group consisting of m-cresol, benzyl alcohol, methyl ethyl, propyl and butyl parabens and phenol is also present if the formulation is packaged in a multi-use container. A sufficient amount of water for injection is added to obtain the desired concentration of solution. Sodium chloride, as well as other excipients, may also be present, if desired. Such excipients, however, must maintain the overall stability of the active ingredient.

Polyhydric alcohols and carbohydrates share the same feature in their backbones, i.e., —CHOH—CHOH—. The polyhydric alcohols include such compounds as sorbitol, mannitol, glycerol, and polyethylene glycols (PEGs). These compounds are straight-chain molecules. The carbohydrates, such as mannose, ribose, trehalose, maltose, glycerol, inositol, glucose and lactose, on the other hand, are cyclic molecules that may contain a keto or aldehyde group. These two classes of compounds will also be effective in stabilizing protein against denaturation caused by elevated temperature and by freeze-thaw or freeze-drying processes. Suitable carbohydrates include galactose, arabinose, lactose or any other carbohydrate which does not have an adverse affect on a diabetic patient, i.e., the carbohydrate is not metabolized to form large concentrations of glucose in the blood. Such carbohydrates are well known in the art as suitable for diabetics.

Preferably, the peptides of the present invention are admixed with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Mannitol is the preferred polyhydric alcohol.

The liquid formulation of the invention should be substantially isotonic and/or iso-osmolar. An isotonic solution may be defined as a solution that has a concentration of electrolytes, or a combination of electrolytes and non-electrolytes that will exert equivalent osmotic pressure as that into which it is being introduced, here for example in the case of parenteral injection of the formulation, a mammalian tissue. Similarly, an iso-osmolar solution may be defined as a solution that has a concentration of non-electrolytes that will exert equivalent osmotic pressure as that into which it is being introduced. As used herein, "substantially isotonic" means within ±20% of isotonicity, preferably within ±10%. As used herein, "substantially iso-osmolar" means within ±20% of iso-osmolality, preferably within ±10%. The formulated product for injection is included within a container, typically, for example, a vial, cartridge, prefilled syringe or disposable pen.

The formulation which best support a unit-dose parenteral lyophilized dosage form is one in which the active ingredient is reasonably stable, with or without adequate buffering capacity to maintain the pH of the solution over the intended shelf life of the reconstituted product. The dosage form should contain a bulking agent to facilitate cake formation. The bulking agent may also act as a tonicifer and/or iso-osmolality modifier upon reconstitution to either facilitate stability of the active ingredient and/or lessen the pain on injection. As noted above, devices that deliver very small injection volumes may not require the formulation to be isotonic and/or iso-osmolar. A surfactant may also benefit the properties of the cake and/or facilitate reconstitution.

These dosage forms include approximately 0.005 to about 0.4%, more specifically from about 0.005 to about 0.02%, or 0.005 to 0.05% (w/v) of the active ingredient. It may not be necessary to include a buffer in the formulation and/or to reconstitute the lyophile with a buffer if the intention is to consume the contents of the container within the stability period established for the reconstituted active ingredient. If a buffer is used, it may be included in the lyophile or in the reconstitution solvent. Therefore, the formulation and/or the reconstitution solvent may contain individually or collectively approximately 0.02 to 0.5% (w/v) of an acetate, phosphate, citrate or glutamate buffer either alone or in combination to obtain a pH of the final composition of approximately 3.0 to 7.0, more specifically from about pH 4.0 to about 6.0, or from about 4.0 to 5.0. The bulking agent may consist of either approximately 1.0 to 10% (w/v) of a carbohydrate or polyhydric alcohol iso-osmolality modifier (as described above) or up to 0.9% saline or a combination of both leading to a isotonic or iso-osmolar solution in the reconstituted aqueous phase. A surfactant, preferably about 0.1 to about 1.0% (w/v) of polysorbate 80 or other non-ionic detergent, may be included. As noted above, sodium chloride, as well as other excipients, may also be present in the lyophilized unit-dosage formulation, if desired. Such excipients, however, must maintain the overall stability of the active ingredient. The formulation will be lyophilized within the validation parameters identified to maintain stability of the active ingredient.

The liquid formulation of the invention before lyophilization should be substantially isotonic and/or iso-osmolar either before lyophilization or to enable formation of isotonic and/or iso-osmolar solutions after reconstitution. The formulation should be used within the period established by shelf-life studies on both the lyophilized form and following reconstitution. The lyophilized product is included within a container, typically, for example, a vial. If other containers are used such as a cartridge, pre-filled syringe, or disposable pen, the reconstitution solvent may also be included.

As with the parenteral liquid and lyophilized unit-dosage formulations described above, the formulation which best supports a multi-dose parenteral lyophilized dosage form is one in which the active ingredient is reasonably stable with adequate buffering capacity to maintain the pH of the solution over the intended "in-use" shelf-life of the product. The dosage form should contain a bulking agent to facilitate cake formation. The bulking agent may also act as a tonicifer and/or iso-osmolality modifier upon reconstitution to either facilitate stability of the active ingredient or lessen the pain on injection or both. Again, devices that deliver very small injection volumes may not require the formulation to be either isotonic and/or iso-osmolar. A preservative is, however, necessary to facilitate multiple use by the patient.

These dosage forms include approximately 0.005 to about 0.4%, more specifically from about 0.005 to about 0.02%, or from about 0.005 to 0.05% (w/v), respectively of the active ingredient. It may not be necessary to include a buffer in the formulation and/or to reconstitute the lyophile with a buffer if the intention is to consume the contents of the container within the stability period established for the reconstituted active ingredient. If a buffer is used, it may be included in the lyophile or in the reconstitution solvent. Therefore, the formulation and/or the reconstitution solvent may contain individually or collectively approximately 0.02 to 0.5% (w/v) of an acetate, phosphate, citrate or glutamate buffer either alone or in combination to obtain a pH of the final composition of approximately 3.0 to 7.0, more specifically from about pH 4.0 to about 6.0, or from about 4.0 to 5.0. The bulking agent may consist of either approximately 1.0 to 10% (w/v) of a carbohydrate or a polyhydric alcohol iso-osmolality modifier (preferably mannitol) or up to 0.9% saline, or a combination of both, leading to an isotonic or iso-osmolar solution in the reconstituted aqueous phase. A surfactant, preferably about 0.1 to about 1.0% (w/v) of polysorbate 80 or other non-ionic detergent, may be included. Approximately 0.005 to 1.0% (w/v) of an anti-microbial preservative selected from the group consisting of m-cresol, benzyl alcohol, methyl, ethyl, propyl and butyl parabens and phenol (preferably m-cresol) is also present if the formulation is packaged in a multi-use container. Sodium chloride, as well as other excipients, may also be present, if desired. Again, however, such excipients must maintain the overall stability of the active ingredient. The formulation should be lyophilized within the validation parameters identified to maintain stability of the active ingredient. The liquid formulation of the invention should be substantially isotonic and/or iso-osmolar either before lyophilization or to enable formation of isotonic and/or iso-osmolar solutions after reconstitution. The formulation should be used within the period established by shelf-life studies on both the lyophilized form and following reconstitution. The lyophilized product is included within a container, typically, for example, a vial. If other containers are used such as a cartridge, pre-filled syringe or disposable pen, the reconstitution solvent may also be included.

The formulations that best support oral, nasal, pulmonary and/or intra-tracheal dosage forms may be either preserved or unpreserved liquid formulations and/or dry powder or, for oral administration, solid formulations. The preserved or unpreserved liquid formulations will be essentially identical to the formulations described above under preserved or unpreserved liquid parenteral formulations. The pH of the solution should be about 3.0 to 7.0, with a pH greater than or equal to about 5.0 being most preferred to reduce the potential for bronchoconstriction. The dry powder formulations may contain a bulking agent and/or salts to facilitate particle size formation and appropriate particle size distribution. A surfactant and/or salts may also benefit the properties of the particle morphology and/or facilitate tissue uptake of the active ingredient.

These dry powder dosage forms can range from 1% to 100% (w/w), respectively of the active ingredient. It may not be necessary to include a bulking agent and/or salts to facilitate particle size formation and/or distribution. The bulking agent and/or salts may consist of either approximately 0 to 99% (w/w) of a carbohydrate or polyhydric alcohol or approximately 0 to 99% salt or a combination of both leading to the preferred particle size and distribution. A surfactant, preferably about 0.1 to about 1.0% (w/w) of polysorbate 80 or other non-ionic detergent, may be included. Sodium chloride, as well as other excipients, may also be present, if desired. Such excipients, however, must maintain the overall stability of the active ingredient and facilitate the proper level of hydration.

The formulations that best support nasal and/or intra-tracheal dosage forms may be either preserved or unpreserved liquid dosage formulations described previously.

Dissolvable gels and/or patches may be used to facilitate buccal delivery. The gels may be prepared from various types of starch and/or cellulose derivatives.

Sublingual delivery may be best supported by liquid formulations similar to those described above as parenteral liquid or parenteral lyophilized formulations after reconstitution except without the need for the dosage form to be an isotonic and/or iso-osmolar solution. Solid dosage forms may be similar to oral solid dosage forms except that they must be readily dissolvable under the tongue.

Oral delivery may be best supported by a liquid (gel cap) formulation that is similar to the parenteral liquid formulation except that the solution may be more concentrated and may contain additional additives to facilitate uptake of the active ingredient by the small intestine. Solid dosage forms will contain inert ingredients along with the active ingredient to facilitate tablet formation. These ingredients may include polyhedral alcohols (such as mannitol), carbohydrates, or types of starch, cellulose derivatives, and/or other inert, physiologically compatible materials. The tablet may be enterically coated to minimize digestion in the stomach and thereby facilitate dissolution and uptake further along the alimentary canal.

Clinical Studies

As described in Example 14 below, a double blind, placebo-controlled single ascending dose study examining the safety, tolerability, and pharmacokinetics of subcutaneous exendin-4 in healthy volunteers has been completed. Five single subcutaneous doses of exendin-4 (0.01, 0.05, 0.1, 0.2 or 0.3 μg/kg) were studied in 40 healthy male volunteers in the fasting state. Maximum plasma exendin-4 concentrations were achieved between one and two hours post-dose with little difference among the doses examined. Examination of the data indicated a dose dependent increase for $C_{max}$. There were no serious adverse events reported in this study.

In the healthy male volunteers that participated in this study, exendin-4 was well tolerated at subcutaneous doses up to and including 0.1 µg/kg. A decrease in plasma glucose concentration was also observed at this dose. At doses of 0.2 µg/kg and higher, the most commonly observed adverse events were headache, nausea, vomiting, dizziness, and postural hypotension. There was a transient fall in plasma glucose concentration following administration of doses of 0.05 µg/kg and above.

Alternate Routes of Delivery

The feasibility of alternate routes of delivery for exendin-4 has been explored by measuring exendin-4 in the circulation in conjunction with observation of a biologic response, such as plasma glucose lowering in diabetic animals, after administration. Passage of exendin-4 has been investigated across several surfaces, the respiratory tract (nasal, tracheal, and pulmonary routes) and the gut (sublingual, gavage and intraduodenal routes). Biologic effect and appearance of exendin-4 in blood have been observed with each route of administration via the respiratory tract, and with sublingual and gavaged peptide via the gastrointestinal tract.

Figure 7:
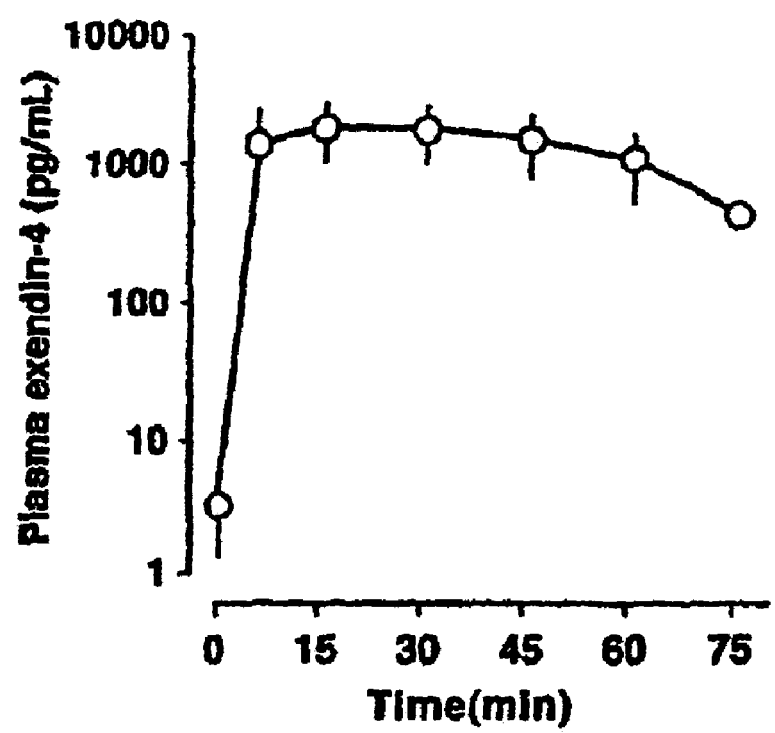
FIG. 7 depicts the plasma levels of exendin-4 in rats after intra-tracheal administration. Male rats (350-400 g) fasted overnight were cannulated in the trachea and femoral artery under anesthesia. Blood was drawn from the arterial line before and after (5, 15, 30, 45, 60, and 75 minutes) 20 μg of exendin-4 dissolved in 50 μL saline was administered into the trachea of each rat (n=4). Plasma exendin-4 levels were determined with an immunoradiometric assay (IRMA).

Intra-tracheal Administration—As described herein, intra-tracheal administration of exendin-4 into fasted rats (20 µg/50 µL/animal) produced a rise in the mean plasma exendin-4 concentration to 2060±960 pg/mL within 5-10 minutes after administration. Elevated plasma exendin-4 concentrations were maintained for at least 1 hour after instillation (see FIG. 7). In diabetic db/db mice, intra-tracheal instillation of exendin-4 (1 µg/animal) lowered plasma glucose concentration by 30% while that in the vehicle control group increased by 41% 1.5 hours after treatment. In these animals the mean plasma concentration of exendin-4 was 777±365 pg/ml at 4.5 hours after treatment (see FIGS. 8a and 8b).

Figure 9B:
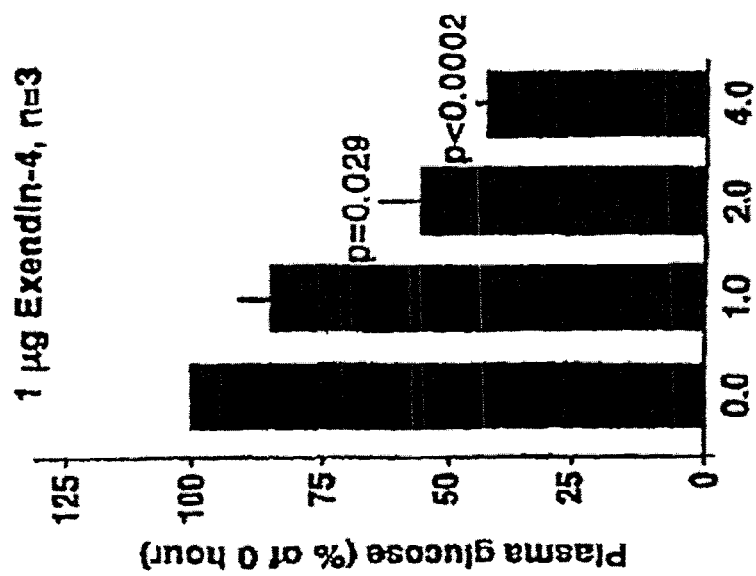
FIGS. 9A and 9B depict the effect of intra-tracheal administration of exendin-4 on plasma glucose in ob/ob mice.
Figure 9A:
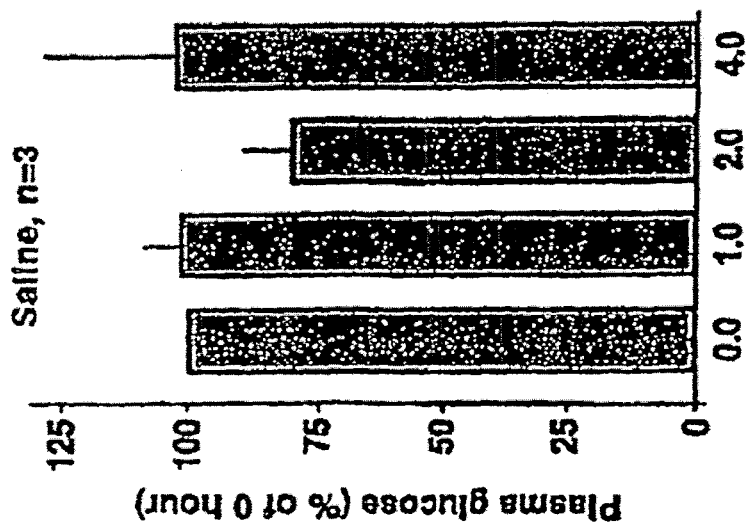

In diabetic ob/ob mice, intra-tracheal instillation of exendin-4 (1 µg/animal) decreased plasma glucose concentration to 43% of the pre-treatment level after 4 hours while that in the vehicle control group was not changed (see FIGS. 9a and 9b).

Figure 10B:
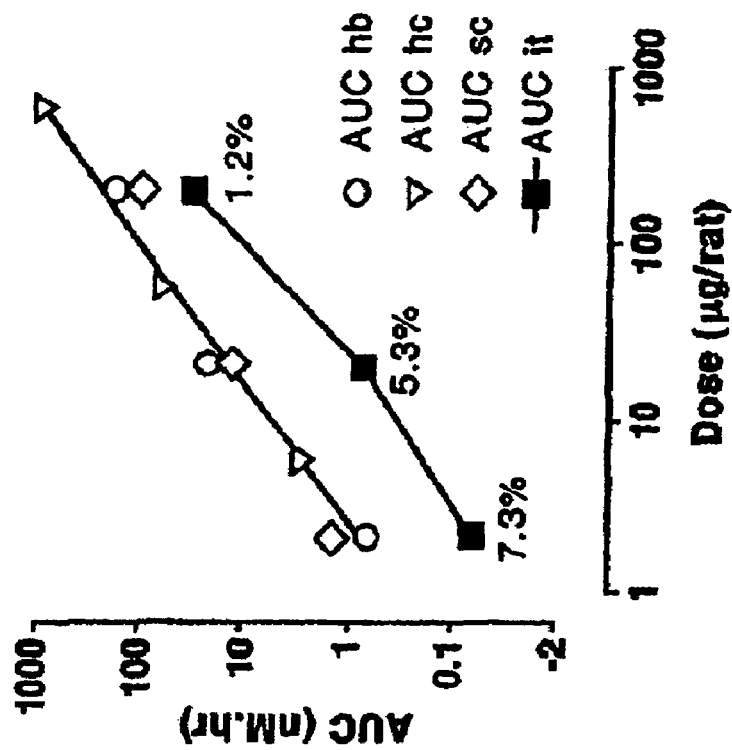
FIG. 10B depicts the bioavailability of exendin-4 following intra-tracheal instillation into rats.
Figure 10A:
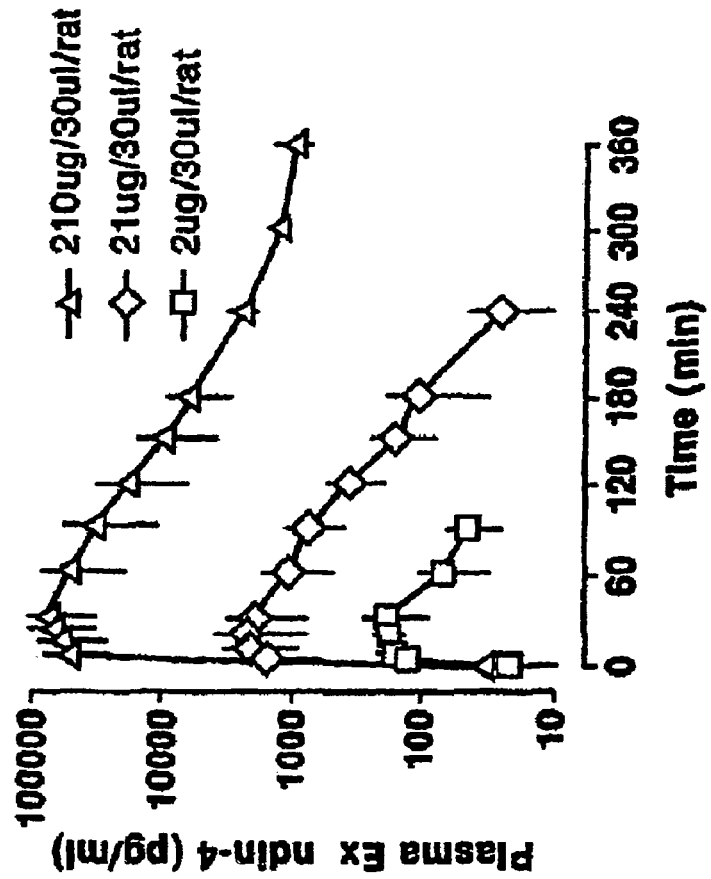
FIG. 10A depicts the plasma exendin-4 concentration after intra-tracheal instillation into rats.
Figure 11:
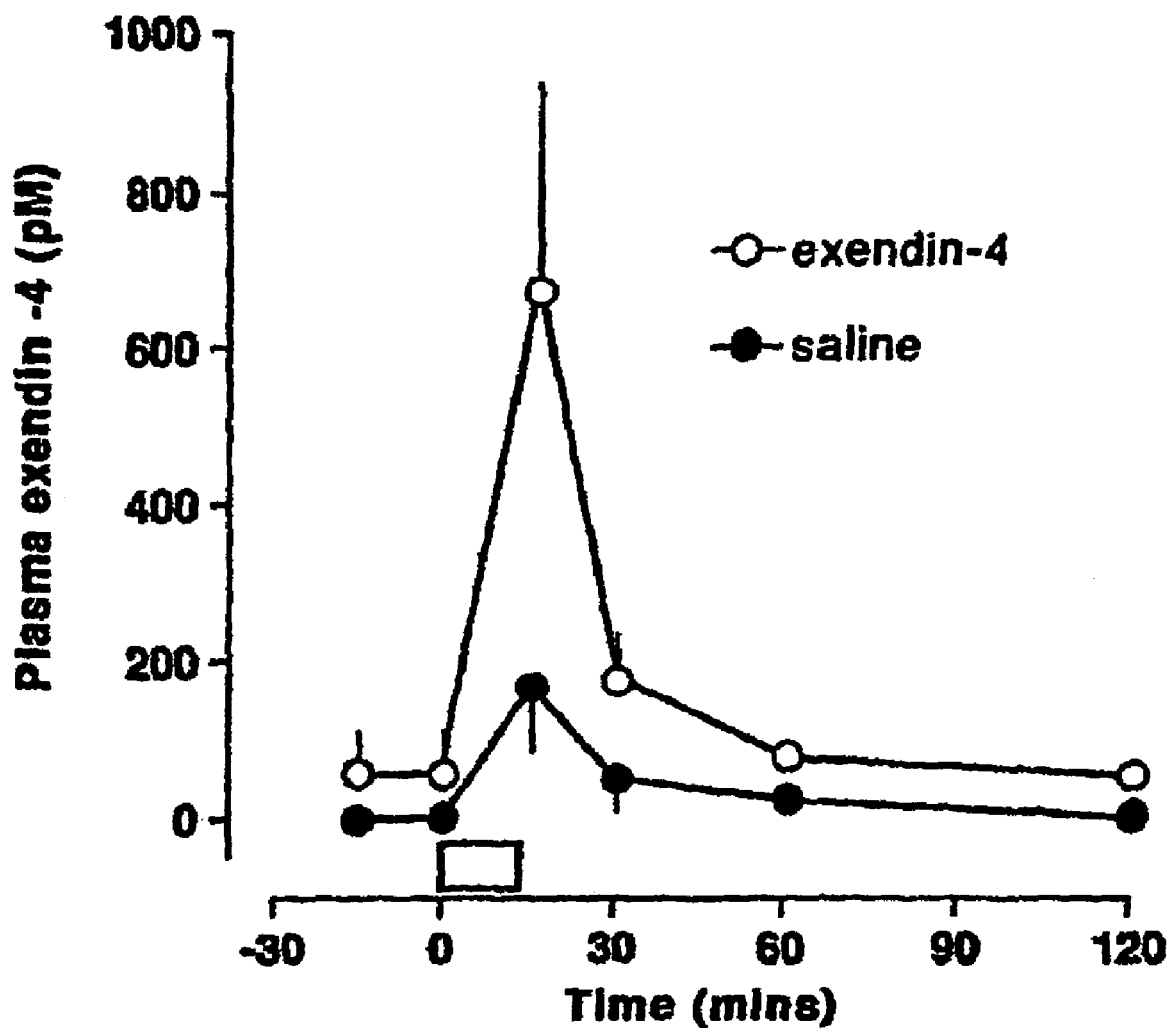
FIG. 11 depicts plasma exendin-4 concentrations in rats (n=6) exposed to saline or aerosolized exendin-4 (8 ng/ml) for 10 minutes. Male rats (approximately 350 g each) fasted overnight were placed in a 2 liter chamber and exposed to aerosolized exendin-4 for 10 minutes. Exendin-4 was nebulized at a rage of 0.2 mg/min at a flow rate of 5 L/min. The concentration of aerosolized exendin-4 was estimated from samples of chamber atmosphere drawn during the course of the experiment.
Figure 12A:
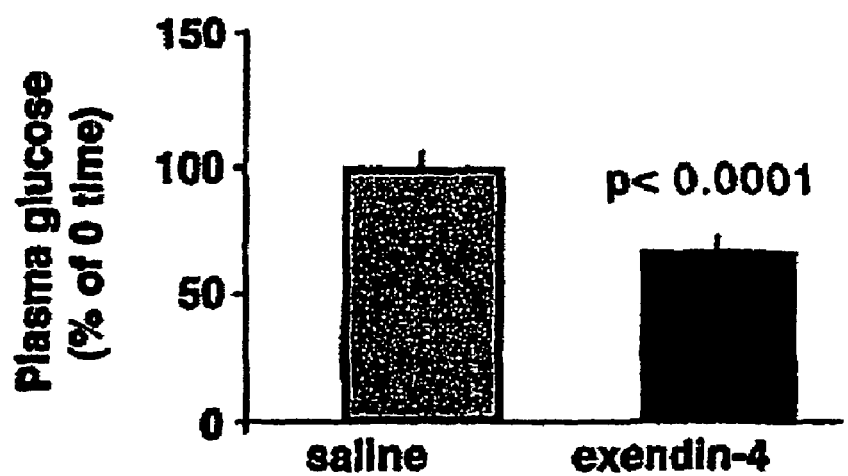
FIG. 12A depicts the effect of ten minutes of exposure to saline or aerosolized exendin-4 (8 μg/ml) on plasma glucose in db/db mice (n=11) one hour after treatment.
Figure 12B:
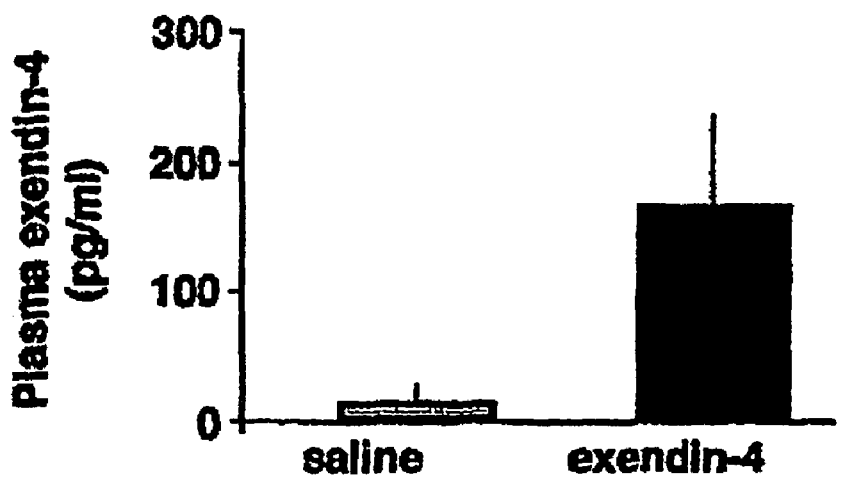
FIG. 12B depicts the plasma exendin-4 concentration after ten minutes of exposure of db/db mice (n=11) to saline or aerosolized exendin-4 (8 ng/ml atmosphere).
Figure 13:
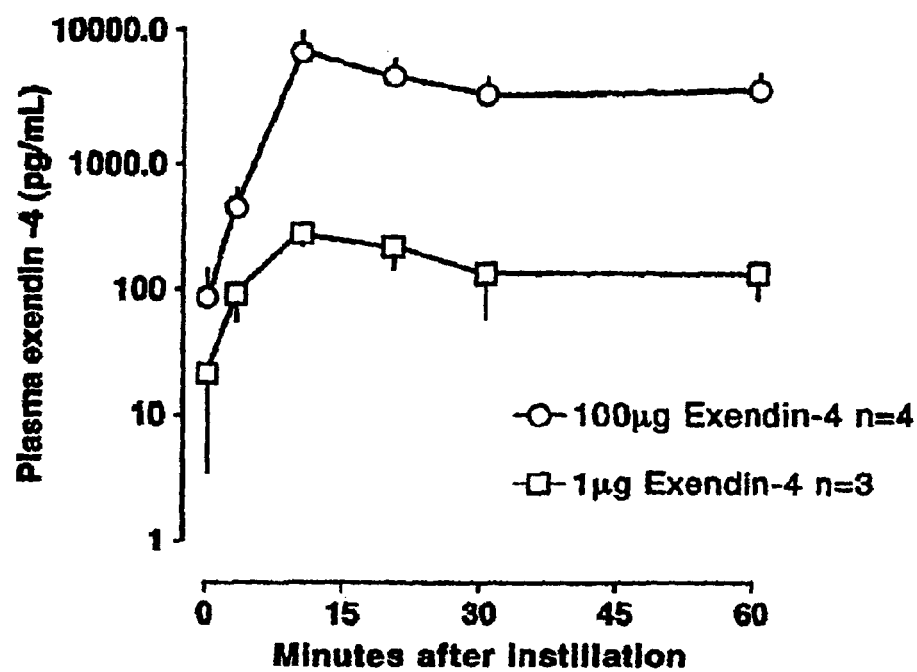
FIG. 13 depicts plasma exendin-4 concentrations in rats after intra-nasal administration of exendin-4. Halan Sprague Dawley rats (311-365 g), nonfasted, were dosed with 0, 1, or 100 µg of exendin-4 in 2 µl of saline by application into the nostrils. Blood samples from anesthetized (Hurricane) tail tip were collected at 0, 3, 10, 20, 30, and 60 minutes after dosing for exendin-4 plasma levels measured by IRMA.
Figure 14:
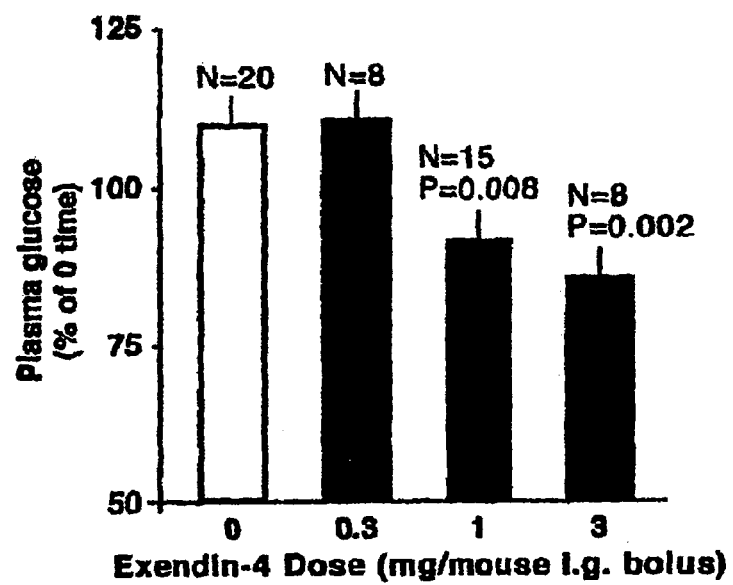
FIG. 14 depicts the effect of intra-gastric administration of exendin-4 on plasma glucose in diabetic db/db mice. Male db/db mice (approximately 50 g) were fasted for 2 hours and bled (40 µl, orbital sinus) before and 1 hour after 200 µl of saline or exendin-4 dissolved in sale was administered i.g. into each animal. Sublingual application of exendin-4 (100 µg/5 µl/animal) to diabetic db/db mice led to a 15% decrease in plasma glucose concentration one hour after treatment. A 30% increase was observed for the control group receiving saline. The mean exendin-4 plasma level at 60 minutes was 4520±1846 pg/mL (see FIG. 8).
Figure 15A:
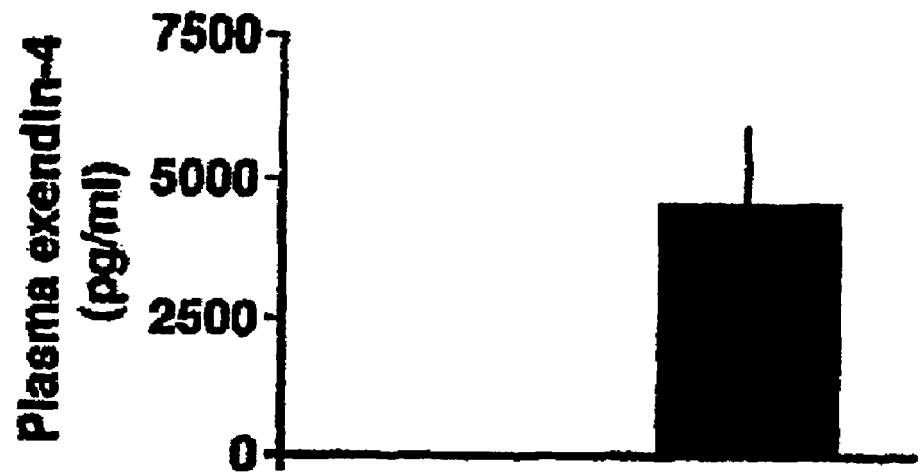
FIG. 15A depicts the plasma exendin-4 concentration after sublingual administration of 100 µg exendin-4 in a 5 µl bolus to db/db mice.
Figure 15B:
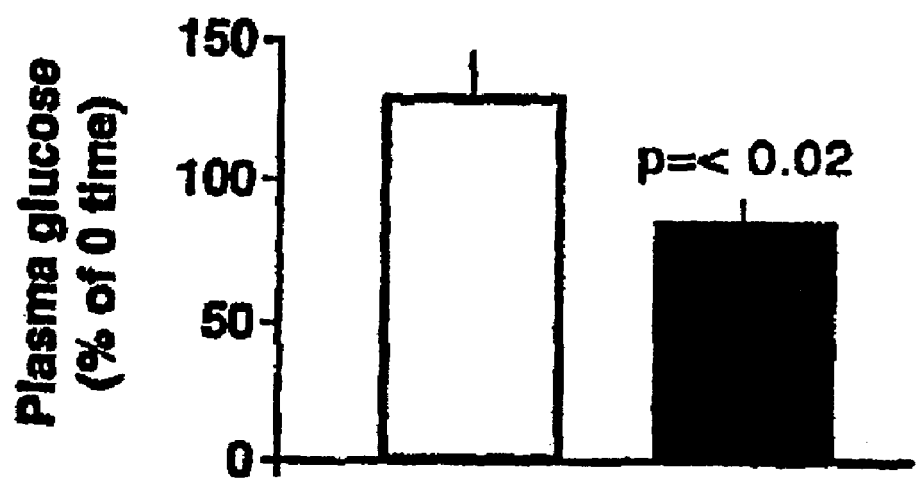
FIG. 15B depicts the effect of 100 µg exendin-4 in a 5 µl bolus of sublingual administration of exendin-4 on plasma glucose in db/db mice.
Figure 15C:
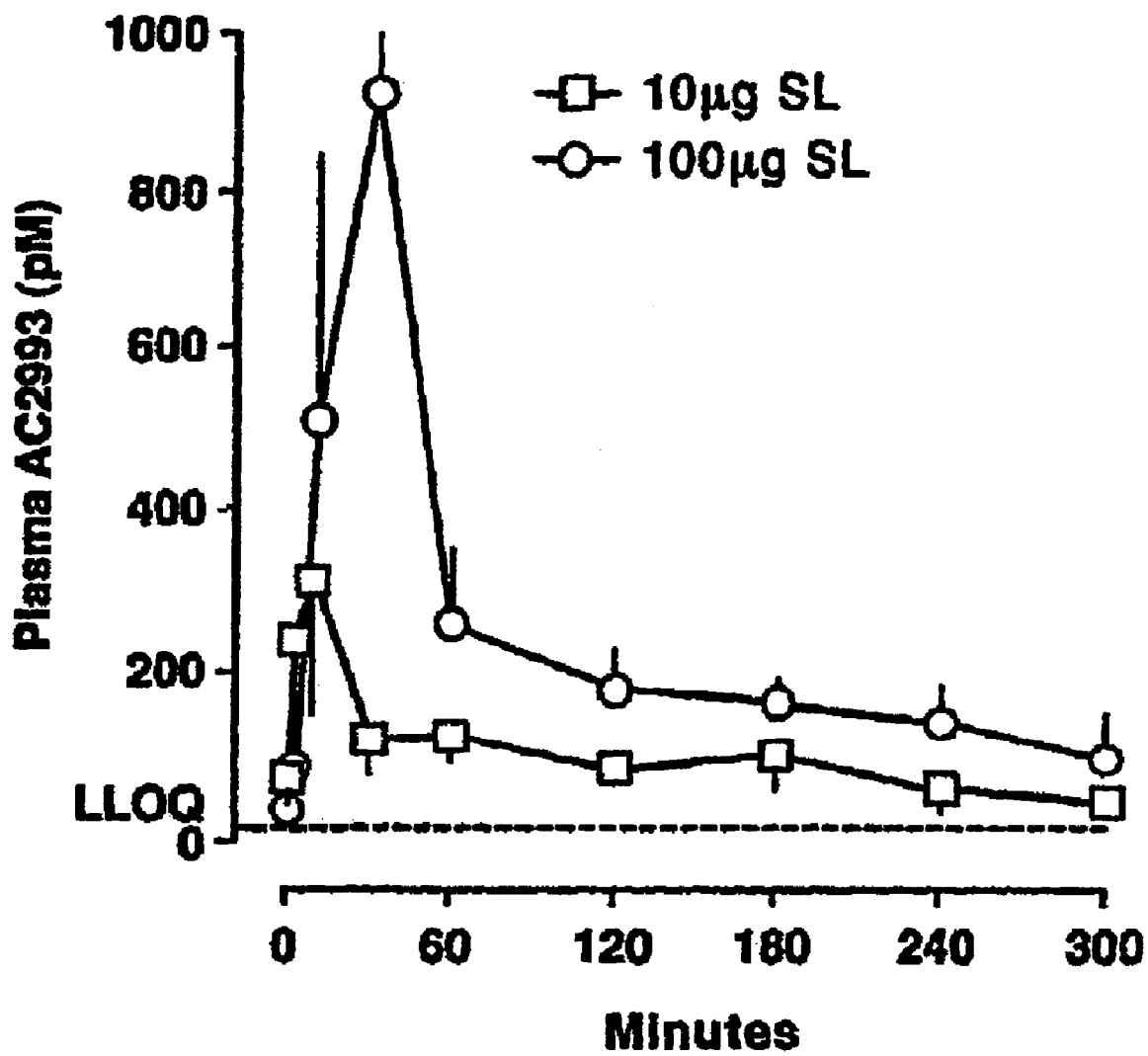
FIG. 15C depicts the plasma exendin-4 concentration after sublingual administration to rats. 10 µg or 100 µg exendin-4 dose was given in 3 µl saline under the tongue in HSD rats (about 300 g) briefly anesthetized with methophane.
Figure 15D:
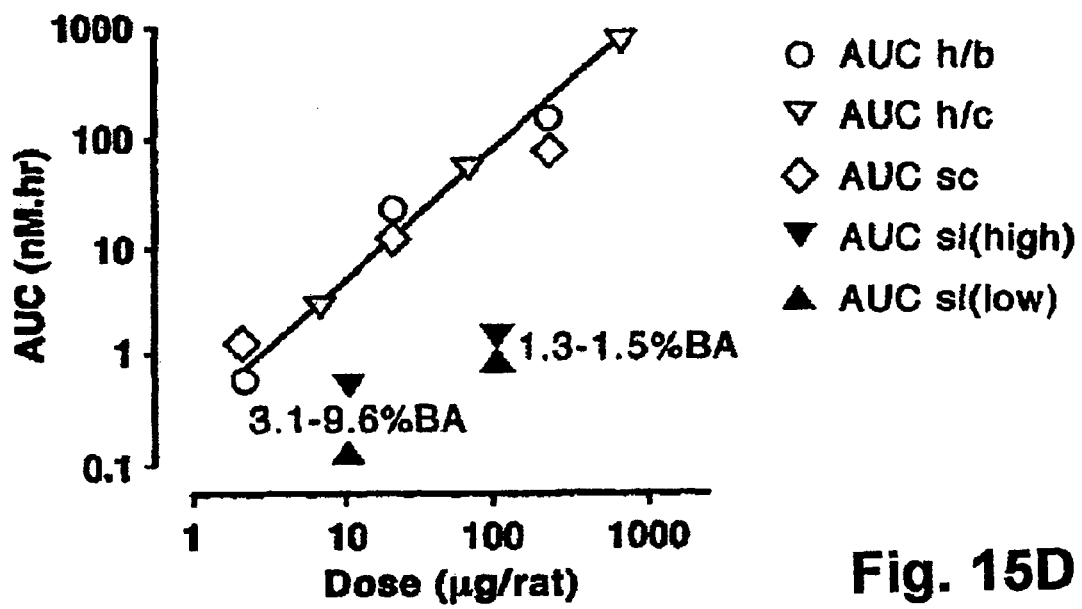
FIG. 15D depicts the bioavailability of exendin-4 after sublingual administration.
Figure 15E:
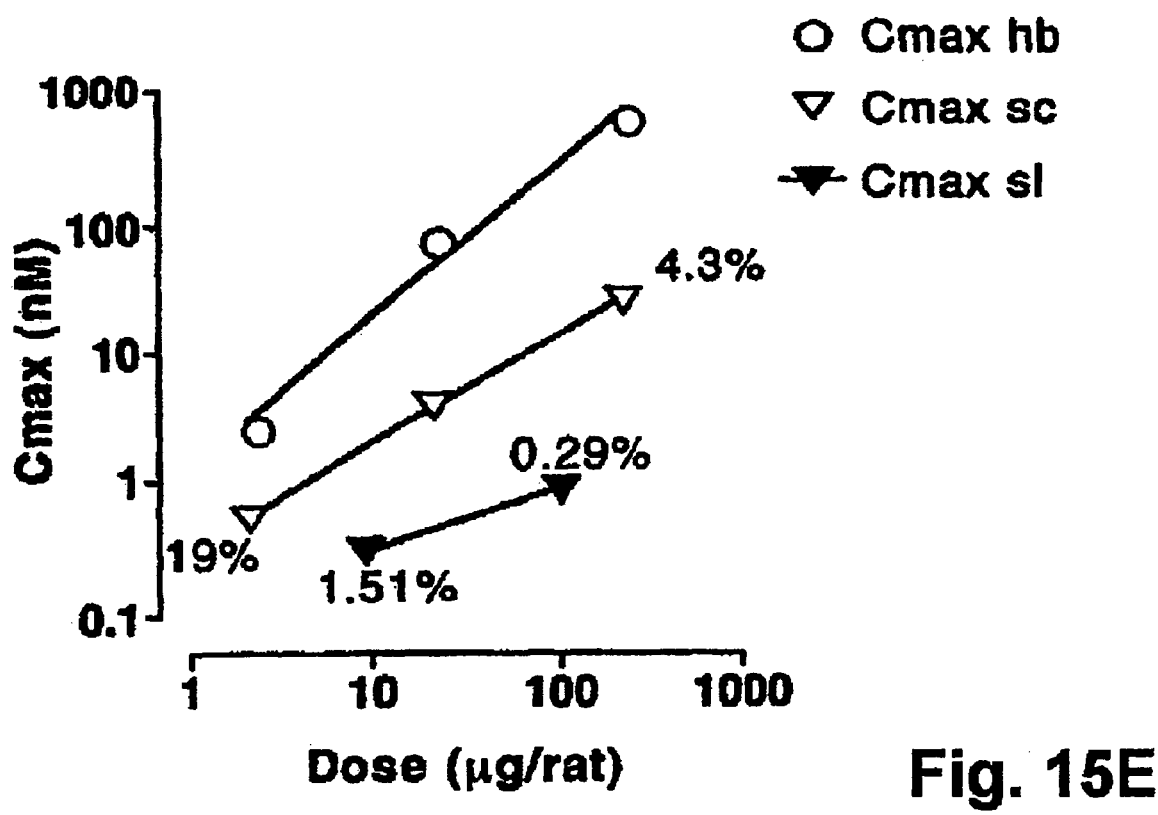
FIG. 15E depicts the Cmax of sublingual exendin-4.

Nine overnight-fasted male Sprague Dawley rats (age 96-115 days, weight 365-395, mean 385 g) were anesthetized with halothane, tracheotomized, and catheterized via the femoral artery. At t=0 min, 30 µL of saline in which was dissolved 2.1 µg (n=3), 21 µg (n=3) or 210 µg of exendin-4 was instilled into the trachea beyond the level of intubation. Blood samples were taken after 5, 10, 20, 30, 60, 90, 120, 150, 180, 240, 300 and 360 min, centrifuged and plasma stored at −20° C. for subsequent immunoradiometric (IRMA) assay directed to N-terminal and C-terminal epitopes of the intact exendin-4 molecule. Following intra-tracheal administration, 61-74% of peak plasma concentration was observed within 5 min. Tmax occurred between 20 and 30 min after administration. AUC and Cmax were proportional to dose. At a dose of 2.1 µg (1.5 nmol/kg), resulting in plasma concentrations of ~50 pM (where glucose-lowering effects in man are observed), bioavailability was 7.3%. The coefficient of variation was 44%. At higher doses, bioavailability was slightly lower, and the CV was higher (see FIGS. 10a and 10b). Via the tracheal route of administration, the t½ (defined pragmatically as time for plasma to fall below 50% of Cmax) was 30-60 min for the lowest dose and 60-90 min for the 2 higher doses. In summary, biologically effective quantities of exendin-4 are rapidly absorbed via the trachea without evoking apparent respiratory distress. The respiratory tract is a viable route of administration of exendin-4.

Pulmonary Administration—Increased plasma concentrations of exendin-4 were detected in rats exposed to aerosolized exendin-4. Exposure of rats to approximately 8 ng of aerosolized exendin-4 per mL of atmosphere for 10 minutes resulted in peak plasma exendin-4 concentrations of 300-1900 pg/mL 5 minutes following treatment (see FIG. 11). Similar exposure of diabetic db/db mice to aerosolized exendin-4 lead to a 33% decrease in plasma glucose concentration after 1 hour, when a mean plasma exendin-4 concentration of 170±67 pg/mL was detected. Diabetic db/db mice in the control group exposed to aerosolized saline recorded no change in plasma glucose (see FIGS. 12*a* and 12*b*).

Nasal administration—Application of exendin-4 into the nasal cavity of rats led to a rise in plasma concentrations. Peak values of 300 pg/mL and 6757 pg/mL were detected 10 minutes after administration of 1 μg and 100 μg exendin-4 (dissolved in 2 μL saline), respectively (see FIG. 13).

Administration via the Gut—Male db/db mice (approximately 50 g body wt.) were fasted for 2 h and before and after an intra-gastric administration of saline or exendin-4 (exendin-4). A 9% decrease in plasma glucose concentration was observed with 1 mg/200 μl/animal and a 15% decrease was observed with 3 mg/200 μl/animal, compared with a 10% increase plasma glucose in the controls one hour after treatment (see FIG. 14).

Sublingual Administration—Sublingual application of exendin-4 (100 μg/5 μL/animal) to diabetic db/db mice led to a 15% decrease in plasma glucose concentration one hour after treatment. A 30% increase was observed for the control group receiving saline. The mean exendin-4 plasma level at 60 minutes was 4520±1846 pg/mL (see FIGS. 15*a*, 15*b*, and 15*c*).

Eight Sprague Dawley rats (~300 g) were briefly anesthetized with metophane while a solution containing 10 μg/3 μL (n=4) or 100 μg/3 μL (n=4) was pipetted under the tongue. Blood samples were subsequently collected from the topically anesthetized tail and assayed for exendin-4 by IRMA. Plasma concentrations had begun to rise by 3 min after administration and were maximal 10 min and 30 min after administration (10 μg and 100 μg doses, respectively). Plasma exendin-4 concentration subsequently remained above the lower limit of quantitation (LLOQ) beyond 5 hours. Area-under-the-curve to the end of each experiment was calculated by the trapezoidal method. Two numbers were derived, one derived from total immunoreactivity, the other derived from the increment above the non-zero value present at t=0. These values were compared to historical intravenous bolus data in the same animal model to obtain, respectively, high and low estimates of bioavailability. For the 10 μg dose, sublingual bioavailability was 3.1-9.6%, and for a 100 μg dose, bioavailability was lower at 1.3-1.5%. Variability of AUC was greatest in the first hour after administration (CV 74% and 128% for 10 and 100 μg doses). For the 5-hour integral, coefficient of variation of the AUC was 20% and 64%, respectively. Peak plasma concentration (Cmax) occurred as rapidly after sublingual administration as after subcutaneous administration (Tmax ~30 min). Cmax after sublingual administration of 10 μg exendin-4 was 1.5% that after an intravenous bolus, but 14.5% of that obtained after a subcutaneous bolus. Cmax after sublingual administration of 100 μg exendin-4 was only 0.29% of that observed after an intravenous bolus, and 6.1% of that obtained after a subcutaneous bolus (see FIGS. 15*d* and 15*e*). Thus, exendin-4 can be delivered at bioeffective doses via the sublingual route. Bioavailability and $C_{max}$ were greatest, $T_{max}$ was shortest, and variability of availability was least with the lowest sublingual dose. The lowest sublingual dose resulted in plasma concentrations similar to those that are predicted to be effective in lowering glucose in humans (~50-100 μM).

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other vertebrates such as other primates, farm animals such as swine, cattle and poultry, and sports animals and pets such as horses, dogs and cats.

To assist in understanding the present invention the following Examples are included which describe the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

Example 1

Preparation of Exendin-3

[SEQ ID NO: 1]
His Ser Asp Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro Pro Ser-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.). In general, single-coupling cycles were used throughout the synthesis and Fast Moc (HBTU activation) chemistry was employed. Deprotection (Fmoc group removal) of the growing peptide chain was achieved using piperidine. Final deprotection of the completed peptide resin was achieved using a mixture of triethylsilane (0.2 mL), ethanedithiol (0.2 mL), anisole (0.2 mL), water (0.2 mL) and trifluoroacetic acid (15 mL) according to standard methods (Introduction to Cleavage Techniques, Applied Biosystems, Inc.) The peptide was precipitated in ether/water (50 mL) and centrifuged. The precipitate was reconstituted in glacial acetic acid and lyophilized. The lyophilized peptide was dissolved in water). Crude purity was about 75%.

Used in purification steps and analysis were Solvent A (0.1% TFA in water) and Solvent B (0.1% TFA in ACN).

The solution containing peptide was applied to a preparative C-18 column and purified (10% to 40% Solvent B in Solvent A over 40 minutes). Purity of fractions was determined isocratically using a C-18 analytical column. Pure fractions were pooled furnishing the above-identified peptide. Analytical RP-HPLC (gradient 30% to 60% Solvent B in Solvent A over 30 minutes) of the lyophilized peptide gave product peptide having an observed retention time of 19.2 minutes.

Example 2

Preparation of Exendin-4

[SEQ ID NO: 2]
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro Pro Ser-NH$_2$

The above amidated peptide was assembled on 4-(2'-4'-dimethoxyphenyl)-Fmoc aminomethyl phenoxy acetamide norleucine MBHA resin (Novabiochem, 0.55 mmole/g) using Fmoc-protected amino acids (Applied Biosystems, Inc.), cleaved from the resin, deprotected and purified in a similar way to Exendin-3 as describe in Example 1. Used in analysis were Solvent A (0.1% TFA in water) and Solvent B (0.1% TFA in ACN). Analytical RP-HPLC (gradient 36% to 46% Solvent B in Solvent A over 30 minutes) of the lyophilized peptide gave product peptide having an observed retention time of 14.9 minutes. Electrospray Mass Spectrometry (M): calculated 4186.6. found 4186.0 to 4186.8 (four lots).

Example 3

Clearance by the Kidney

The kidney can play a major role in the elimination of some molecules (drugs, peptides, proteins). For some molecules, this process begins when the kidney filters the blood at the glomerulus to produce the ultrafiltrate described below. The glomerular filter discriminates not only on the basis of molecular weight but also by acting as a negatively charged selective barrier, promoting retention of anionic compounds. The free fraction of molecules in the plasma (not protein bound) with a molecular weight less than 5 kD and an effective radii less than 15 Å are easily filtered. For larger molecular weight molecules they are filtered on a more restrictive and limited basis, principally by molecular size, structure and net charge. The cutoff point for glomerular filtration lies between albumin (67 kD) which is retained and hemoglobin (68 kD) which is filtered. Albumin, with an effective radius of about 36 Å is filtered less than 1% at the glomerulus.

Once in the glomerulus a molecule travels to the proximal tubule where it is either reabsorbed or it passes on through the loop of Henle to the distal tubule where collecting ducts drain the filtrate into the bladder. Filtered proteins and peptides are typically cleaved by brush border enzymes in the proximal tubule, from where they are efficiently retrieved by sodium/amino cotransporters (scavenging pumps). Otherwise, molecules which are polar, ionized and of large molecular weight will not be reabsorbed. Throughout this process metabolizing enzymes in the renal cortex (proximal tubules) may also degrade the molecule into more polar molecules, thereby increasing the probability for excretion into the urine. Many peptide hormones (for example, amylin, calcitonins) are degraded by passage through the renal circulation, presumably by vascular ectoenzymes accessible to the plasma, independently of the process of glomerular filtration. In those examples, rates of peptide clearance from the plasma are similar to the rate of renal plasma flow, which is ~3-fold greater than the rate of glomerular filtration.

Studies performed to identify plasma circulating metabolites of exendin-4 yielded very little evidence of proteolytic degradation; following large intravenous doses in animals, HPLC analysis of plasma showed only the presence of intact exendin, and negligible appearance of "daughter" peaks indicative of the buildup of degradation products. This is in contrast to other peptides studied (for example amylin and GLP-1) where the disappearance of the "parent" HPLC peak was associated with the appearance of "daughter" HPLC peaks, subsequently identified as subpeptide degradants. The absence of plasma degradants of exendin indicates little or no proteolysis at any site, including the renal circulation. Any clearance by the kidney, then, is via non-proteolytic means, namely filtration or active excretion (as occurs with para-amino hippurate).

Figure 6:
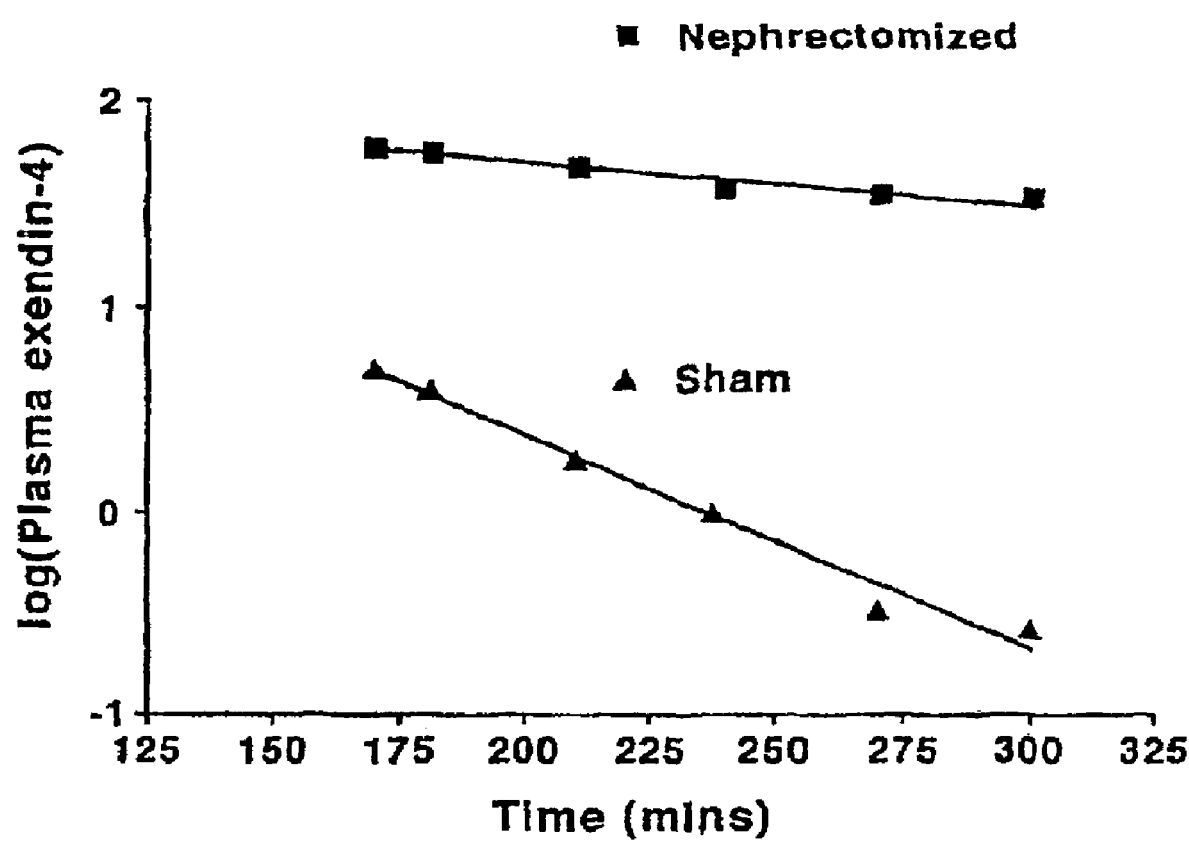
FIG. 6 is a graph showing the terminal decay of exendin-4 plasma levels in nephrectomized and sham subjects. In the nephrectomized subjects, the slope=−0.00212 and T1/2=−326.4 minutes. In the sham subjects, the slope=−0.01037 and T1/2=−66.9 minutes.

Initial measurements of exendin clearance in man (120-130 mL/min), monkeys (~9 mL/min) and rats (3.2-4.4 mL/min) matched reported glomerular filtration rates in those species. To test whether renal filtration could be the principal mode of exendin elimination, studies were performed in overnight fasted nephrectomized male rats infused with exendin at a constant rate. Steady-state plasma levels of exendin-4 were greatly increased in nephrectomized rats compared to rats with their kidneys intact. This data indicated that the kidney was responsible for at least 80% of the clearance of exendin 4 (see FIGS. 5 and 6). Exendin clearance rates in intact rats were, again, similar to glomerular filtration rates expected in those rats (4.2 mL/min). Taken together these results indicate that very little metabolism occurs systemically and that most of the clearance of exendin 4 is through the kidney via filtration (but not by renal intravascular proteolysis). The low amounts of immunoreactive full-length exendin in the urine are consistent with it being cleaved by brush border enzymes in the proximal tubule after filtration.

Example 4

Exendin-4 Decreases Glucagon Secretion During Hyperglycemic Clamps in Diabetic Fatty Zucker Rats Absolute or relative hyperglucagonemia is often a feature of, for example, type 1 and type 2 diabetes mellitus, and the suppression of excessive glucagon secretion in these and other conditions described or referred to herein is a potential benefit of therapy using glucagonostatic agents. In this Example, the effect of exendin-4 on glucagon secretion in male anaesthetized Diabetic Fatty Zucker (ZDF) rats was examined. Using an hyperinsulinemic hyperglycemic clamp protocol, factors tending to influence glucagon secretion were held constant. Plasma glucose was clamped at ~34 mM 60 min before beginning intravenous infusions of saline (n=7) or exendin-4 (0.21 µg+2.1 µg/mL/h; n=7). Plasma glucagon concentration measured prior to these infusions were similar in both groups (306±30 pM versus 252±32 pM, respectively; n.s.).

Mean plasma glucagon concentration in exendin-4 infused rats was nearly half of that in saline-infused rats in the final 60 minutes of the clamp (165±18 pM versus 298±26 pM, respectively; P<0.002). The hyperglycemic clamp protocol also enabled measurement of insulin sensitivity. Glucose infusion rate during the clamp was increased by 111±7% in exendin-4-treated versus control rats (P<0.001). In other words, exendin-4 exhibited a glucagonostatic effect in ZDF rats during hyperglycemic clamp studies, an effect that will be of therapeutic benefit in diabetic humans.

Example 5

Metabolic Effects of Exendin-4 on Glucagon Secretion in People with Type 2 Diabetes In this Example, the safety, tolerability, and efficacy of synthetic exendin-4 was evaluated in 8 male non-insulin using patients with type 2 diabetes who had discontinued other antidiabetic therapy for a minimum of 7 days. Each patient received subcutaneous (SC) injections of placebo (PBO) and 0.1, 0.2, and 0.3 µg/kg exendin-4 48 hours apart in a single-blind, dose-rising, placebo controlled crossover design. Five patients also received a 0.4 µg/kg dose. Plasma glucose, insulin and glucagon concentrations were assessed fasting and in response to a 7 Kcal/kg Sustacal® challenge administered at the time of exendin-4/PBO injection. Gastric emptying was evaluated by measuring serum acetaminophen concentrations following a 20 mg/kg oral dose of liquid acetaminophen administered with the Sustacal®. No safety issues were identified based upon reported adverse events, EKG and safety lab monitoring. Doses of 0.3 and 0.4 µg/kg elicited a dose-dependent increase in nausea; vomiting occurred at the highest dose.

Plasma glucose concentrations were reduced in all doses of exendin-4 compared to PBO although insulin concentrations were not significantly different. The 8 hour mean±SE changes in plasma glucose AUC from baseline were +391±187, −263±108, −247±64, −336±139, and −328±70 mg*hr/dL for the PBO, 0.1, 0.2, 0.3, and 0.4 µg/kg doses respectively. The 3 hr changes in plasma glucagon were +128.0±19.2, −5.6±10.5, −29.4±18.6, −40.5±24.5, and +6.9±38.6 pg*hr/mL respectively. The gastric emptying rate was slowed in all doses and the mean total absorbed acetaminophen over 6 hours was reduced by 51%, 50%, 57% and 79% compared to PBO for 0.1, 0.2, 0.3, and 0.4 µg/kg doses respectively. In summary, SC injection of exendin-4 to patients identified no safety issues, was tolerated at doses ≦0.3 µg/kg, reduced plasma glucose and glucagon and slowed the rate of gastric emptying. These observations support the use of exendin for the treatment of conditions that would benefit from reduced glucagon levels and/or suppression of glucagon, including but not limited to type 1 and type 2 diabetes.

Example 6

PEG Modified Exendin-4

In the case of exendin 4, a 39 amino acid peptide with a molecular weight of 4187, modifications that increase its size and/or increase its anionic nature will decrease its ability to be filtered by the kidney. Because clearance of exendin 4 is largely by the kidney this will effectively increase its half life. Other properties of PEGylation (increased plasma half-life due to evasion of such renal and/or cellular clearance mechanisms that may exist; reduced immunogenicity and antigenicity; increased solubility; resistance to proteolysis; reduced toxicity (avoid dose spike); improved thermal and mechanical stability; improved permeability of the mucus or epithelial layer; and selective control over a specific biological function) are also of potential benefit for exendin 4 and exendin agonists.

In particular, because we have observed multiple pharmacologies (likely representing multiple receptor subtypes), different spectra of biological activities of exendin 4 may be selected by putting a PEG group at appropriate positions. Loss or alteration of bioactivity has been reported for PEGylated proteins which may be due to the presence of the PEG chains themselves, the particular site occupied by the PEG chain, or the coupling conditions having an adverse effect on the protein.

Primary considerations for PEG modification in terms of filtration at the kidney of exendin and exendin agonists are size and charge. Unmodified, exendin 4 has a molecular weight of approximately 4.2 kD and is anionic in nature with an overall net charge of approximately −2 at physiological pH. One, two or three PEG constituents may be covalently linked to exendin 4 or an analog of exendin 4, for example, with one PEG constituent being preferred. The size of the PEG can vary from a molecular weight of 500 to 20,000, preferably between 5,000 and 12,000.

Many of the methods for covalent attachment of PEG take advantage of the epsilon-amino group on lysine. Exendin 4 has two lysines that can be modified by attachment of PEG. An alanine scan of AC3177 (Leu$^{14}$, Phe$^{25}$1-28 exendin-4 (SEQ ID NO:9)), a shortened analog of exendin 4, revealed positions that are sensitive to substitution by alanine. The two lysines at positions 12 and 27 were moderately affected by this substitution suggesting that loss of the lysine specific R group side chain (methylene chain plus epsilon-amino group) is tolerated. With regard to the full-length peptide, exendin 4, the two lysine positions are appropriate for PEG attachment (see compounds 1 and 2). In addition, depending on the chemistry used to conjugate the PEG, the epsilon-amino groups at these positions may be masked thereby increasing the anionic nature of the peptide.

(201)                                            (SEQ ID NO: 223)
HGEGTFTSDLSK(PEG)QMEEEAVRLFIEWLKNGGPSSGAPPPS-NH$_2$ (202)                                            (SEQ ID NO: 224)
HGEGTFTSDLSKQMEEEAVRLFIEWLK(PEG)NGGPSSGAPPPS-NH$_2$

Based on the results of the alanine scan, other likely positions that may be modified by insertion of a Lys-PEG or equivalent, for example, are:

(203)                                            (SEQ ID NO: 225)
HK(PEG)EGTFTSDLSKQMEEEAVRLFIEWLKNGGPSSGAPPPS-NH$_2$ (204)                                            (SEQ ID NO: 226)
HGEGK(PEG)FTSDLSKQMEEEAVRLFIEWLKNGGPSSGAPPPS-NH$_2$ (205)                                            (SEQ ID NO: 227)
HGEGTFTK(PEG)DLSKQMEEEAVRLFIEWLKNGGPSSGAPPPS-NH$_2$ (206)                                            (SEQ ID NO: 228)
HGEGTFTSDK(PEG)SKQMEEEAVRLFIEWLKNGGPSSGAPPPS-NH$_2$ (207)                                            (SEQ ID NO: 229)
HGEGTFTSDLK(PEG)KQMEEEAVRLFIEWLKNGGPSSGAPPPS-NH$_2$ (208)                                            (SEQ ID NO: 230)
HGEGTFTSDLSKK(PEG)MEEEAVRLFIEWLKNGGPSSGAPPPS-NH$_2$ (209)*                                           (SEQ ID NO: 231)
HGEGTFTSDLSKQMEK(PEG)EAVRLFIEWLKNGGPSSGAPPPS-NH$_2$ (210)*                                           (SEQ ID NO: 232)
HGEGTFTSDLSKQMEEK(PEG)AVRLFIEWLKNGGPSSGAPPPS-NH$_2$ (211)                                            (SEQ ID NO: 233)
HGEGTFTSDLSKQMEEEAK(PEG)RLFIEWLKNGGPSSGAPPPS-NH$_2$ (212)                                            (SEQ ID NO: 234)
HGEGTFTSDLSKQMEEEAVRK(PEG)FIEWLKNGGPSSGAPPPS-NH$_2$ (213)*                                           (SEQ ID NO: 235)
HGEGTFTSDLSKQMEEEAVRLFIK(PEG)WLKNGGPSSGAPPPS-NH$_2$ (214)                                            (SEQ ID NO: 236)
HGEGTFTSDLSKQMEEEAVRLFIEK(PEG)LKNGGPSSGAPPPS-NH$_2$ (215)                                            (SEQ ID NO: 237)
HGEGTFTSDLSKQMEEEAVRLFIEWLKK(PEG)GGPSSGAPPPS-NH$_2$

The three positions* above normally containing a glutamic acid that were indicated for modification with K(PEG) can also be modified by conjugation to the glutamic side chain carboxyl group, E(PEG).

Another analog in which the Lys-PEG can be added is at the supposed GlyGly turn:

(216)                                            (SEQ ID NO: 238)
HGEGTFTSDLSKQMEEEAVRLFIEWLKNK(PEG)GPSSGAPPPS-NH$_2$ (217)                                            (SEQ ID NO: 239)
HGEGTFTSDLSKQMEEEAVRLFIEWLKNGK(PEG)PSSGAPPPS-NH$_2$

Positions 29-39 of exendin-4 may not be critical for the glucose lowering activity as evidenced by AC3177 having nearly equipotent activity to exendin 4, and any of them, alone or in combination, can be substituted for K(PEG) or an equivalent.

Example 7

Exendin-4 is a Circulating, Meal-Related Peptide in the Gila Monster

This experiment investigated whether exendin-4 has a metabolic role in the Gila monster lizard itself. To investigate whether exendin-4 appeared in the blood of the Gila monster in response to feeding, blood was sampled from one animal fasted for 7 weeks, before and 30 min after ingestion of a small rat. Plasma was assayed for full-length exendin-4 using an immunoradiometric assay with monoclonal antibody pairs directed to epitopes at N- and C-termini of exendin-4. Fasting plasma exendin-4 concentration was 76 pg/mL, near the lower limit of quantitation. After eating, this value rose 300-fold to 23,120 pg/mL.

In a second experiment, serial samples were taken from two animals fasted five weeks before and after ingestion of one or two small rats (47-49 g). Plasma exendin-4 concentration rose 23- to 36-fold (to 4860, 8340 pg/mL) immediately after eating, consistent with a direct passage of exendin-4 from the salivary gland to blood. After eating a second rat (t=30 min), plasma exendin-4 concentration in one Gila rose further to 27,209 pg/mL. Plasma exendin-4 concentration decayed with a t½ of 5.00 and 5.33 hours, respectively. In conclusion, exendin-4, known to originate from the salivary gland of the Gila monster, appears in high concentration in the blood immediately after eating. This may represent a meal-related signal to inhibit further eating and promote nutrient storage.

Example 8

Exendin-4 Decreases Glucagon Secretion During Hyperglycemic Clamps in Diabetic Fatty Zucker Rats Absolute or relative hyperglucagonemia is often a feature of type 1 and type 2 diabetes mellitus, and the suppression of excessive glucagon secretion is a potential benefit of therapy using glucagonostatic agents. In this Example, the effect of exendin-4 on glucagon secretion in male anaesthetized Diabetic Fatty Zucker (ZDF) rats was examined. Using an hyperinsulinemic hyperglycemic clamp protocol, factors tending to influence glucagon secretion were held constant. Plasma glucose was clamped at ~34 mM 60 min before beginning intravenous infusions of saline (n=7) or exendin-4 (0.21 µg+2.1 µg/mL/h; n=7). Plasma glucagon concentration measured before these infusions were similar in both groups (306±30 pM versus 252±32 pM, respectively; n.s.).

Mean plasma glucagon concentration in exendin-4 infused rats was nearly half of that in saline-infused rats in the final 60 minutes of the clamp (165±18 pM versus 298±26 pM, respectively; P<0.002). The hyperglycemic clamp protocol also enabled measurement of insulin sensitivity. Glucose infusion rate during the clamp was increased by 111±7% in exendin-4-treated versus control rats (P<0.001). In other words, exendin-4 exhibited a glucagonostatic effect in ZDF rats during hyperglycemic clamp studies, an effect that will be of therapeutic benefit in diabetic humans.

Example 9

Pharmacokinetics of Exendin-4 in the Rat Following Intravenous, Subcutaneous and Intraperitoneal Administration This Example describes work to define the plasma pharmacokinetics of exendin-4 in rats (~350 g body weight each) following 2.1, 21, 210 µg/rat i.v. bolus, s.c. and i.p. administration and 2.1, 21, 210 µg/hr/rat i.v. infusion (3 hr). Serial samples of plasma (~120 µL) were assayed using a validated immunoradiometric assay (IRMA). This sandwich-type assay uses mouse-based monoclonal antibodies that react with exendin-4 but do not react with GLP-1 or tested metabolites of exendin-4 or GLP-1. The lower limit of quantitation was 15 pM (63 pg/mL). The estimated $t_{1/2}$ for exendin-4 was 18-41 min for i.v. bolus, 28-49 for i.v. continuous, 90-216 min for s.c. and 125-174 min for i.p. injection. Bioavailability was 65-76% for s.c. and i.p. injection. Clearance determined from the i.v. infusion was 4-8 mL/min. Both $C_{max}$ and AUC values within each route of administration were proportional to dose. Volume of distribution was 457-867 mL. Clearance and bioavailability were not dose dependent. $C_{max}$ (or steady-state plasma concentration; $C_{ss}$) is shown in the table below

| | Cmax or Css (nM) | | | |
|---|---|---|---|---|
| | Route | | | |
| Dose | IV bolus | IV infusion | Subcutaneous | IP |
| 2.1 µg | 2.9 ± 0.4 | 1.1 ± 0.1 | 0.56 ± 0.12 | 0.26 ± 0.04 |
| 21 µg | 70 ± 3 | 19 ± 1.9 | 4.1 ± 1.5 | 3.9 ± 1 |
| 210 µg | 645 ± 12 | 262 ± 60 | 28 ± 4 | 35 ± 6 |

Example 10

Comparison of the Insulinotropic Actions of Exendin-4 and GLP-1 During an Intravenous Glucose Challenge in Rats This experiment compares the insulinotropic actions of synthetic exendin-4 and GLP-1 in vivo following an intravenous (i.v.) glucose challenge in rats. Sprague-Dawley rats (~400 g) were anesthetized with halothane and cannulated via the femoral artery and saphenous vein. Following a 90-min recovery period, saline or peptide (30 µmol/kg/min each) was administered i.v. (1 ml/h for 2 hours; n=4-5 for each group). Thirty min after infusion commenced, D-glucose (5.7 mmol/kg, 0.8 ml) was injected i.v. In saline-treated, exendin-4-treated and GLP-1-treated rats, plasma glucose concentrations were similar before injection (9.3±0.3, 9.7±0.3, 10.3±0.4 mM), increased by similar amounts after glucose injection (21.7, 21.3, 23.7 mM), and resulted in a similar 60-min glucose AUC (987±39, 907±30, 1096±68 mM·min, respectively). That is, the glycemic stimulus was similar in each treatment group. Plasma insulin concentration in saline-treated rats increased 3.3-fold with the glucose challenge (230±53 to a peak of 765±188 µM). With exendin-4 infusion, the increase in plasma insulin concentration was 6.8-fold (363±60 to 2486±365 µM). With GLP-1 the increase in plasma insulin concentration was 2.9-fold (391±27 to 1145±169 µM), which was similar to that obtained in saline-treated rats. The 60-min insulin AUC in saline-treated rats was 24±6 nM·min, was increased 2.8-fold in exendin-treated rats (67±8 nM·min; P<0.003 versus saline; P<0.02 versus GLP-1) and by 20% in GLP-1-treated rats (n.s. versus saline). Amplification of glucose-stimulated insulin release by exendin-4 was also tested at infusion rates of 3 and 300 pmol/kg/min and shown to be dose-dependent. Thus, exendin-4 is more potent and/or effective than GLP-1 in amplifying glucose-stimulated insulin release in intact rats.

Example 11

Development and Validation of an Immunoradiometric Assay (IRMA) for the quantitation of Exendin-4 in Plasma and its Application to Preclinical Toxicity and Phase I Clinical Evaluations A sensitive and specific sandwich-type immunoradio-metric (IRMA) assay was developed for quantitation of plasma exendin-4 concentration using synthetic exendin-4 as the immunogen. One mouse-derived monoclonal antibody recognizes a C-terminal epitope on exendin-4 (capture antibody) but does not cross-react with GLP-1. The second antibody (detector antibody labeled with $^{125}$I) recognizes an N-terminal epitope on exendin-4 and GLP-1, and requires a terminal histidine for binding. Thus, the assay as a whole does not detect GLP-1 (7-36)NH$_2$, GLP-1 (7-36)COOH or exendin(3-39). Assay validation in rat, monkey, dog, rabbit and human plasmas showed inter- and intra-assay coefficients of variation <20% and <10%, respectively, accuracy of ±15% with target low, mid and high controls, and lower and upper limits of quantitation of 62.8 and 2512 pg/mL, respectively. Plasma samples from 28-day subcutaneous toxicity evaluations of exendin-4 in rats and monkeys and a Phase I clinical study in normal subjects were evaluated using the IRMA. The $C_{max}$ values in the animals studies are shown in the table below. Human samples from subcutaneous administration of 0.05, 0.1, 0.2 and 0.3 µg/kg yielded $C_{max}$ values of 90, 224, 370 and 587 pg/mL.

| | Cmax (pg/mL) | | |
|---|---|---|---|
| | Dose (µg/kg) | | |
| | 10 | 100 | 1000 |
| Rat | 7,000 | 127,000 | 1,180,000 |
| Monkey | 20,000 | 170,000 | 1,890,000 |

Example 12

Comparison of GLP-1 Receptor Binding/Activating and Glucose-Lowering Effects of GLP-1 and Exendin-4

Exendin-4 was synthesized by solid phase peptide synthesis techniques and compared to synthetic GLP-1 in terms of in vitro binding to, and activation of, GLP-1 receptors, and in vivo in terms of lowering plasma glucose in diabetic db/db mice. In a plasma membrane preparation of a rat insulinoma cell line (RINm5f) that expresses the GLP-1 receptor, the peptides were assayed for their ability to bind and displace radiolabeled GLP-1 and for their ability to stimulate the production of cAMP. The relative order of binding potency was found to be GLP-1>exendin-4. The relative order of cyclase activation was GLP-1=exendin-4. Affinities, as shown in the table below, differ over a 4- to 5-fold range. In contrast, in vivo glucose lowering potency differed over a 3430-fold range. Exendin-4 was 3430-fold more potent than GLP-1. The in vivo potency of exendin-4 does not match potency at the GLP-1 receptor, and is likely the culmination of an aggregate of properties.

|  | Binding IC50 (nM) | Cyclase EC50 (nM) | Glucose-lowering ED50 (μg) |
|---|---|---|---|
| GLP-1 | 0.15 | 0.28 | 20.6 |
| Exendin-4 | 0.66 | 0.30 | 0.006 |

Example 13

Comparison of Glycemic Indices and Insulin Sensitivity in Pair-Fed and Exendin-4 Treated Diabetic Fatty Zucker Rats This Example tests whether the beneficial effects of exendin-4 in ZDF rats were secondary to changes in food intake. It compares effects obtained with exendin-4 to effects observed in saline-treated matched animals who consumed the same amount of food as was eaten by ZDF rats injected subcutaneously twice daily with 10 μg exendin-4. Plasma glucose and HbA1c were measured weekly for 6 weeks. One day after the last treatment, animals were anesthetized with halothane and subjected to an hyperinsulinemic (50 mU/kg/min) euglycemic clamp. Changes in HbA1c over 6 weeks differed between treatment groups ($P<0.001$ ANOVA), increasing in ad lib fed (n=5) and pair fed (n=5) rats, but decreasing in exendin-4-treated rats (n=5). Similarly, changes in plasma glucose differed between treatment groups ($P<0.002$ ANOVA), increasing in ad lib fed and pair fed ZDF rats, and decreasing in ZDF rats treated with exendin-4. In the final hour of a 3-hour clamp protocol, glucose infusion rate in exendin-4-treated rats tended to be higher than in pair fed (+105%) and ad lib fed (+20%) controls, respectively (10.14±1.43 n=5, 8.46±0.87 n=4, 4.93±2.02 mg/kg/min n=3; n.s. P=0.09 ANOVA). Another index of insulin sensitivity, plasma lactate concentration, differed significantly between treatment groups ($P<0.02$ ANOVA) and was lowest in exendin-4-treated rats. Thus, exendin-4 treatment is associated with improvement in glycemic indices and in insulin sensitivity that is partly, but not fully, matched in controls fed the same amount of food, indicating that improvements in metabolic control with exendin-4 in ZDF rats are at least partly due to mechanisms beyond caloric restriction.

Example 14

Clinical Studies and the Stimulation of Endogenous Insulin Secretion by Subcutaneous Synthetic Exendin-4 in Healthy Overnight Fasted Volunteers In a double blind, placebo-controlled single ascending dose clinical trial to explore safety and tolerability and pharmacokinetics of synthetic exendin-4, exendin-4 formulated for subcutaneous injection was evaluated in healthy male volunteers while assessing effects upon plasma glucose and insulin concentrations. Five single subcutaneous doses of exendin-4 (0.01, 0.05, 0.1, 0.2 or 0.3 μg/kg) were studied in 40 healthy male volunteers in the fasting state. Maximum plasma exendin-4 concentrations were achieved between 1 and 2 hours post-dose with little difference among the doses examined. Examination of the data indicated a dose dependent increase for $C_{max}$. There were no serious adverse events reported in this study and in the healthy male volunteers that participated in this study, exendin-4 was well tolerated at subcutaneous doses up to and including 0.1 μg/kg. A decrease in plasma glucose concentration was also observed at this dose. At doses of 0.2 μg/kg and higher, the most commonly observed adverse events were headache, nausea, vomiting, dizziness, and postural hypotension. There was a transient fall in plasma glucose concentration following administration of doses of 0.05 μg/kg and above.

Forty healthy, lean (mean BMI (±SE) 22.7±1.2) subjects aged 18-40 years were randomly assigned to 5 groups. Within each group of 8 subjects, 6 were assigned to exendin-4 and 2 to placebo (PBO). Exendin-4 (0.01, 0.05, 0.1, 0.2 or 0.3 μg/kg) or placebo was administered following an overnight fast and plasma exendin-4, glucose and insulin concentrations monitored along with safety and tolerability. No safety issues were observed. Doses ≦0.1 μg/kg were tolerated as well as PBO whereas 0.2 and 0.3 μg/kg elicited a dose-dependent increase in nausea and vomiting. Peak plasma exendin-4 concentrations rose dose-dependently and following 0.1 μg/kg, exendin-4 immunoreactivity persisted for 360 min. Plasma glucose decreased following all doses, except 0.01 μg/kg, reached a nadir by 30 min and returned back to baseline within 180 min. Subjects receiving 0.3 μg/kg received a caloric beverage 30 minutes after dosing, precluding comparison of their data. Mean change in plasma glucose (0-180 min): 0.03±0.07, −0.07±0.08, −0.38±0.14, −0.85±0.13 and −0.83±0.23 mmol/L for PBO, 0.01, 0.05, 0.1, and 0.2 μg/kg respectively; $P<0.02$ versus PBO. The lowest plasma glucose recorded was 3.4 mmol/L. Corresponding mean changes in plasma insulin (0-120 min) were 0.43±0.59, 2.37±0.58, 2.28±0.66, 4.91±1.23, and 14.00±3.34 μU/mL; $P<0.01$ versus PBO for the 0.1 and 0.2 μg/kg groups. Thus, in healthy, overnight fasted volunteers, subcutaneous injection of exendin-4 (1) presented no safety issues, (2) was well-tolerated at doses ≦0.1 μg/kg, (3) led to exendin-4 immunoreactivity in plasma for up to 6 hrs, (4) increased plasma insulin and lowered plasma glucose in a dose-dependent manner without inducing hypoglycemia.

Example 15

Effectiveness of Alternative Delivery of Exendin-4 in Rodents

This Example tested the delivery of exendin-4 by means alternative to injection, and examined its ability to traverse mucosal surfaces in sufficient quantities to exert biological effect. Changes in concentration of plasma glucose and of intact synthetic exendin-4 (measured by a 2-site immunoradiometric assay) were observed in db/db mice administered a saline solution containing differing doses of synthetic exendin-4 via the trachea, via an aerosol mist (pulmonary), via gavage (oral), and under the tongue (sublingual). The same routes of administration, as well as intraduodenally and nasally, were tested in rats, and bioavailability was calculated, for example, for sublingual and intra-tracheal routes. Exendin-4 administered via each of the above routes in mice resulted in significant glucose-lowering activity 1 to 4 hours after administration (db/db mice intra-tracheal P<0.02; ob/ob mice intra-tracheal P<0.0002; db/db mice aerosol P<0.0001; gavage P<0.002; sublingual P<0.02). Dose-dependent increases in plasma exendin-4 concentration were up to 777±365 pg/mL (db/db mice intra-tracheal); 170±67 pg/mL (db/db mice aerosol); 4520±1846 pg/mL (db/db mice sublingual). Similarly, in rats, exendin-4 concentrations were observed up to 68,682±38,661 pg/mL (intra-tracheal); 1900 pg/mL (pulmonary); 6757 pg/mL (nasal); 3,862±2,844 pg/mL (sublingual); but no apparent absorption or biological activity when delivered intraduodenally. Bioavailability of exendin-4 in saline was ~7.3% at lower doses when delivered via the trachea, where 61-74% of Cmax was observed within 5 min. Kinetics thereafter were similar to those observed after subcutaneous administration. Bioavailability of exendin-4 in saline delivered under the tongue was 3.1-9.6% at lower doses. These studies support the delivery of exendin-4 and peptide agonist analogs thereof in biologically effective quantities via convenient non-injectable routes.

Examples 16 to 20

Reagents Used

GLP-1[7-36]NH$_2$ (GLP-1) was purchased from Bachem (Torrance, Calif.). All other peptides were prepared using synthesis methods such as those described therein. All chemicals were of the highest commercial grade. The cAMP SPA immunoassay was purchased from Amersham. The radioligands were purchased from New England Nuclear (Boston, Mass.). RINm5f cells (American Type Tissue Collection, Rockville, Md.) were grown in DME/F12 medium containing 10% fetal bovine serum and 2 mM L-glutamine. Cells were grown at 37° C. and 5% $CO_2$/95% humidified air and medium was replaced every 2 to 3 days. Cells were grown to confluence then harvested and homogenized using on a Polytron homogenizer. Cell homogenates were stored frozen at −70° C. until used.

Example 16

GLP-1 Receptor Binding Studies

Receptor binding was assessed by measuring displacement of [$^{125}$I]GLP-1 or [$^{125}$I]exendin(9-39) from RINm5f membranes. Assay buffer contained 5 µg/ml bestatin, 1 µg/ml phosphoramidon, 1 mg/ml bovine serum albumin (fraction V), 1 mg/ml bacitracin, and 1 mM $MgCl_2$ in 20 mM HEPES, pH 7.4. To measure binding, 30 µg membrane protein (Bradford protein assay) was resuspended in 200 µl assay buffer and incubated with 60 µM [$^{125}$I]GLP-1 or [$^{125}$I]exendin(9-39) and unlabeled peptides for 120 minutes at 23° C. in 96 well plates (Nagle Nunc, Rochester, N.Y.). Incubations were terminated by rapid filtration with cold phosphate buffered saline, pH 7.4, through polyethyleneimine-treated GF/B glass fiber filters (Wallac Inc., Gaithersburg, Md.) using a Tomtec Mach II plate harvester (Wallac Inc., Gaithersburg, Md.). Filters were dried, combined with scintillant, and radioactivity determined in a Betaplate liquid scintillant counter (Wallac Inc.).

Peptide samples were run in the assay as duplicate points at 6 dilutions over a concentration range of $10^{-6}$M to $10^{-12}$M to generate response curves. The biological activity of a sample is expressed as an $IC_{50}$ value, calculated from the raw data using an iterative curve-fitting program using a 4-parameter logistic equation (Prizm, GraphPAD Software).

Example 17

Cyclase Activation Study

Assay buffer contained 10 µM GTP, 0.75 mM ATP, 2.5 mM $MgCl_2$, 0.5 mM phosphocreatine, 12.5 U/ml creatine kinase, 0.4 mg/ml aprotinin, 1 µM IBMX in 50 mM HEPES, pH 7.4. Membranes and peptides were combined in 100 ml of assay buffer in 96 well filter-bottom plates (Millipore Corp., Bedford, Mass.). After 20 minutes incubation at 37° C., the assay was terminated by transfer of supernatant by filtration into a fresh 96 well plate using a Millipore vacuum manifold. Supernatant cAMP contents were quantitated by SPA immunoassay. Peptide samples were run in the assay as triplicate points at 7 dilutions over a concentration range of $10^{-6}$M to $10^{-12}$M to generate response curves. The biological activity of a particular sample was expressed as an $EC_{50}$ value, calculated as described above.

Example 18

Determination of Blood Glucose Levels in db/db Mice

C57BLKS/J-m-db mice at least 3 months of age were utilized for the study. The mice were obtained from The Jackson Laboratory and allowed to acclimate for at least one week before use. Mice were housed in groups of ten at 22° C.±1° C. with a 12:12 light:dark cycle, with lights on at 6 a.m. All animals were deprived of food for 2 hours before taking baseline blood samples. Approximately 70 µl of blood was drawn from each mouse via eye puncture, after a light anesthesia with metophane. After collecting baseline blood samples, to measure plasma glucose concentrations, all animals receive subcutaneous injections of either vehicle (10.9% NaCl), exendin-4 or test compound (1 µg) in vehicle. Blood samples were drawn again, using the same procedure, after exactly one hour from the injections, and plasma glucose concentrations were measured. For each animal, the % change in plasma value, from baseline value, was calculated.

Example 19

Dose Response Determination of Blood Glucose Levels in db/db Mice

C57BLKS/J-m-db/db mice, at least 3 months of age were utilized for the study. The mice were obtained from The Jackson Laboratory and allowed to acclimate for at least one week before use. Mice were housed in groups of ten at 22° C.±1° C. with a 12:12 light:dark cycle, with lights on at 6 a.m. All animals were deprived of food for 2 hours before taking baseline blood samples. Approximately 70 µl of blood was drawn from each mouse via eye puncture, after a light anesthesia with metophane. After collecting baseline blood samples, to measure plasma glucose concentrations, all animals receive subcutaneous injections of either vehicle, exendin-4 or test compound in concentrations indicated. Blood samples were drawn again, using the same procedure, after exactly one hour from the injections, and plasma glucose concentrations were measured. For each animal, the % change in plasma value, from baseline value, was calculated and a dose dependent relationship was evaluated using Graphpad Prizm™ software.

Example 20

Gastric Emptying

The following study was and may be carried out to examine the effects of exendin-4 and/or an exendin agonist compound on gastric emptying in rats. This experiment followed a modification of the method of Scarpignato, et al., *Arch. Int. Pharmacodyn. Ther.* 246:286-94, 1980. Male Harlan Sprague Dawley (HSD) rats were used. All animals were housed at 22.7±0.8 C in a 12:12 hour light:dark cycle (experiments being performed during the light cycle) and were fed and watered ad libitum (Diet LM-485, Teklad, Madison, Wis.). Exendin-4 was synthesized according to standard peptide synthesis methods. The preparation of exendin-4 is described in Example 2. The determination of gastric emptying by the method described below was performed after a fast of 20 hours to ensure that the stomach contained no chyme that would interfere with spectrophotometric absorbance measurements.

Conscious rats received by gavage, 1.5 ml of an acaloric gel containing 1.5% methyl cellulose (M-0262, Sigma Chemical Co, St Louis, Mo.) and 0.05% phenol red indicator. Twenty minutes after gavage, rats were anesthetized using 5% halothane, the stomach exposed and clamped at the pyloric and lower esophageal sphincters using artery forceps, removed and opened into an alkaline solution which was made up to a fixed volume. Stomach content was derived from the intensity of the phenol red in the alkaline solution, measured by absorbance at a wavelength of 560 nm. In separate experiments on 7 rats, the stomach and small intestine were both excised and opened into an alkaline solution. The quantity of phenol red that could be recovered from the upper gastrointestinal tract within 20 minutes of gavage was 89±4%; dye which appeared to bind irrecoverably to the gut luminal surface may have accounted for the balance. To account for a maximal dye recovery of less than 100%, percent of stomach contents remaining after 20 min were expressed as a fraction of the gastric contents recovered from control rats sacrificed immediately after gavage in the same experiment. Percent gastric contents remaining=(absorbance at 20 min)/(absorbance at 0 mm)×100.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims.

What is claimed is:

1. A lyophilized formulation comprising about 0.005% (w/v) to about 0.4% (w/v) exendin-4 and about 1.0% (w/v) to about 10% (w/v) mannitol.

2. A lyophilized formulation comprising about 0.005% (w/v) to about 0.4% (w/v) of exendin-4 or an exendin agonist analog thereof and about 1.0% (w/v) to about 10% (w/v) of one or more compounds selected from the group consisting of mannose, ribose, trehalose, maltose, glycerol, inositol, glucose, lactose, galactose, arabinose, sorbitol, mannitol, glycerol, xylitol, a polypropylene/ethylene glycol copolymer, and a polyethylene glycol.

3. The lyophilized formulation of claim 2, wherein the formulation comprises exendin-4.

4. The lyophilized formulation of claim 2, wherein the exendin or the exendin agonist analog is present in an amount of about 0.005% (w/v) to about 0.02% (w/v).

5. The lyophilized formulation of claim 2, wherein the formulation comprises exendin-4.

6. A lyophilized formulation comprising about 0.005% (w/v) to about 0.4% (w/v) of exendin-4 or an exendin agonist analog thereof and about 1.0% (w/v) to about 10% (w/v) of a bulking agent.

7. The lyophilized formulation of claim 6, wherein the bulking agent is a carbohydrate, a polyhydric alcohol, or a combination thereof.

8. The lyophilized formulation of claim 7, wherein the carbohydrate is mannose, ribose, trehalose, maltose, glycerol, inositol, glucose, lactose, galactose, or arabinose.

9. The lyophilized formulation of claim 7, wherein the polyhydric alcohol is sorbitol, mannitol, glycerol, xylitol, a polypropylene/ethylene glycol copolymer, or a polyethylene glycol.

10. The lyophilized formulation of claim 6, wherein the bulking agent is mannitol.

11. The lyophilized formulation of claim 6, further comprising about 0.1% (w/v) to about 1.0% (w/v) of a surfactant.

12. The lyophilized formulation of claim 6, further comprising about 0.02% (w/v) to about 0.5% (w/v) of a buffer.

13. The lyophilized formulation of claim 12, wherein the buffer is an acetate buffer, a phosphate buffer, a citrate buffer, a glutamate buffer, or a combination of two or more thereof.

14. The lyophilized formulation of claim 6, further comprising about 0.005% (w/v) to about 1.0% (w/v) of an anti-microbial preservative.

15. The lyophilized formulation of claim 14, wherein the anti-microbial preservative is m-cresol, benzyl alcohol, methyl paraben, ethyl paraben, propyl paraben, butyl paraben, or phenol.

16. The lyophilized formulation of claim 6, comprising about 0.005% (w/v) to about 0.02% (w/v) of the exendin or the exendin agonist analog.

17. The lyophilized formulation of claim 6, comprising about 0.005% (w/v) to about 0.05% (w/v) of the exendin or the exendin agonist analog.

18. The lyophilized formulation of claim 6, wherein the lyophilized formulation is a unit dosage formulation or a multi-unit dosage formulation.

19. The lyophilized formulation of claim 6, wherein the exendin or the exendin agonist analog comprises the amino acid sequence of any one of SEQ ID NOs: 4-239.

20. The lyophilized formulation of claim 6, wherein the formulation comprises exendin-4.

* * * * *

UNITED STATES PATENT AND TRADEMARK OFFICE
CERTIFICATE OF CORRECTION

| | | |
|---|---|---|
| PATENT NO. | : 7,906,146 B2 | Page 1 of 1 |
| APPLICATION NO. | : 12/389509 | |
| DATED | : March 15, 2011 | |
| INVENTOR(S) | : Orville Kolterman et al. | |

It is certified that error appears in the above-identified patent and that said Letters Patent is hereby corrected as shown below:

In Column 223, Claim 3, line 55, replace --"formulation comprises exendin-4."-- with --formulation comprises exendin-3 or exendin-4,--.

Signed and Sealed this
Third Day of May, 2011

David J. Kappos
*Director of the United States Patent and Trademark Office*